US010604488B2

(12) United States Patent
Trawick et al.

(10) Patent No.: US 10,604,488 B2
(45) Date of Patent: *Mar. 31, 2020

(54) (+)-MORPHINANS AS ANTAGONISTS OF TOLL-LIKE RECEPTOR 9 AND THERAPEUTIC USES THEREOF

(71) Applicant: Mallinckrodt LLC, Hazelwood, MO (US)

(72) Inventors: Bobby N. Trawick, Florissant, MO (US); David W. Berberich, St. Peters, MO (US); Christopher W. Grote, Webster Groves, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 46 days.

This patent is subject to a terminal disclaimer.

(21) Appl. No.: 15/255,979

(22) Filed: Sep. 2, 2016

(65) Prior Publication Data

US 2017/0029432 A1 Feb. 2, 2017

Related U.S. Application Data

(63) Continuation of application No. 12/975,407, filed on Dec. 22, 2010, now Pat. No. 9,562,014, which is a continuation-in-part of application No. 12/837,545, filed on Jul. 16, 2010, now abandoned.

(60) Provisional application No. 61/226,015, filed on Jul. 16, 2009, provisional application No. 61/286,877, filed on Dec. 16, 2009.

(51) Int. Cl.
| | |
|---|---|
| *A61K 31/167* | (2006.01) |
| *A61K 31/472* | (2006.01) |
| *A61K 31/485* | (2006.01) |
| *C07D 217/20* | (2006.01) |
| *C07D 221/28* | (2006.01) |
| *C07D 489/00* | (2006.01) |
| *C07D 489/02* | (2006.01) |
| *C07D 489/10* | (2006.01) |
| *C07D 489/08* | (2006.01) |

(52) U.S. Cl.
CPC .......... *C07D 217/20* (2013.01); *A61K 31/167* (2013.01); *A61K 31/472* (2013.01); *A61K 31/485* (2013.01); *C07D 221/28* (2013.01); *C07D 489/00* (2013.01); *C07D 489/02* (2013.01); *C07D 489/08* (2013.01); *C07D 489/10* (2013.01)

(58) Field of Classification Search
CPC .. C07D 217/20; C07D 221/28; C07D 489/00; C07D 489/02; C07D 489/08; C07D 489/10; A61K 31/167; A61K 31/472; A61K 31/485
See application file for complete search history.

(56) References Cited

U.S. PATENT DOCUMENTS

| | | | |
|---|---|---|---|
| 4,521,601 A | 6/1985 | Rice | |
| 5,668,285 A | 9/1997 | Rice et al. | |
| 5,919,826 A | 7/1999 | Caruso | |
| 6,277,859 B1 * | 8/2001 | Nagase | ............... C07D 405/12 514/282 |
| 8,080,661 B2 | 12/2011 | Wang et al. | |
| 8,168,790 B2 | 5/2012 | Bao et al. | |
| 8,252,929 B2 | 8/2012 | Wentland | |
| 8,519,133 B2 | 8/2013 | Grote et al. | |
| 8,778,958 B2 | 7/2014 | Cashman | |
| 8,946,419 B2 | 2/2015 | Grote et al. | |
| 2009/0156817 A1 | 6/2009 | Wang et al. | |
| 2009/0156818 A1 | 6/2009 | Wang et al. | |
| 2009/0312552 A1 | 12/2009 | Bao et al. | |
| 2010/0069639 A1 | 3/2010 | Wang et al. | |
| 2010/0081819 A1 | 4/2010 | Wang et al. | |
| 2010/0197921 A1 | 8/2010 | Grote et al. | |
| 2011/0136845 A1 | 6/2011 | Trawick et al. | |
| 2011/0251229 A1 * | 10/2011 | Watkins | ............... A61K 31/485 514/289 |

FOREIGN PATENT DOCUMENTS

| | | |
|---|---|---|
| CN | 101 066 948 A | 11/2007 |
| CN | 101 265 266 A | 9/2008 |
| EP | 0418591 A2 | 3/1991 |
| EP | 1810973 A1 | 7/2007 |
| WO | 98/17268 A2 | 4/1998 |
| WO | 02/080918 A1 | 10/2002 |
| WO | 03/070191 A1 | 8/2003 |
| WO | 2004/022564 A2 | 3/2004 |
| WO | 2007/127624 A1 | 11/2007 |
| WO | 2009/012005 A1 | 1/2009 |
| WO | 2009/023819 A2 | 2/2009 |
| WO | 2009/051824 A2 | 4/2009 |
| WO | WO 2009/059048 * 5/2009 ........... A61K 31/485 |

(Continued)

OTHER PUBLICATIONS

Imaeda et al. (J. Clin. Invest. 119:305-314 (2009)).*
Bi et al., "Rifampicin inhibits microglial inflammation and improves neuron survival against inflammation," Brain Research, 2011, pp. 12-20, vol. 1395.
Lujia et al., "Ceftriaxone pretreatment protects rats against cerebral ischemic injury by attenuating microglial activation-induced IL-1β expression," International Journal of Neuroscience, 2014, pp. 657-665, vol. 124, No. 9.
Sweitzer et al., "Propentofylline: Glial Modulation, Neuroprotection, and Alleviation of Chronic Pain," Handbook of Experimental Pharmacology, 2011, pp. 235-250, vol. 200.
Ratchford et al., "Decreased microglial activation in MS patients treated with glatiramer acetate," J. Neurology, 2012, pp. 1199-1205, vol. 259, No. 6.

(Continued)

*Primary Examiner* — Robert H Havlin

(57) ABSTRACT

The present invention provides (+)-morphinans comprising Toll-like receptor 9 (TLR9) antagonist activity, as well as methods for using the (+)-morphinans to treat pain. Also provided are pharmaceutical combination compositions comprising a (+)-morphinan and an opioid agonist/monoamine reuptake inhibitor, as well as methods for using the combination compositions to treat pain.

10 Claims, 26 Drawing Sheets

(56) References Cited

FOREIGN PATENT DOCUMENTS

| WO | 2010/039209 A2 | 4/2010 |
|---|---|---|
| WO | 2010/096045 A1 | 8/2010 |
| WO | 2010/096790 A1 | 8/2010 |
| WO | 2010/096791 A1 | 8/2010 |
| WO | 2010/144641 A1 | 12/2010 |
| WO | 2011/009015 A1 | 1/2011 |
| WO | 2012/008984 A1 | 1/2012 |

OTHER PUBLICATIONS

Kiebala et al., "Ibudilast, a Pharmacologic Phosphodiesterase Inhibitor, Prevents Human Immunodeficiency Virus-1 Tat-Mediated Activation of Microglial Cells," PLoS One, 2011, e18633, pp. 1-13, vol. 6, No. 4.
Huang et al., "Anti-Neuroinflammatory Effects of the Calcium Channel Blocker Nicardipine on Microglial Cells: Implications for Neuroprotection," PLoS One, 2014, e91167, pp. 1-10, vol. 9, No. 3.
Ding et al., "Antiviral drug ganciclovir is a potent inhibitor of microglial proliferation and neuroinflammation," J. Exp. Med., 2014, pp. 189-198, vol. 211, No. 2.
Martin-Moreno et al. "Cannabidiol and Other Cannabinoids Reduce Microglial Activation in Vitro and in Vivo: Relevance to Alzheimer's Disease," Molecular Pharmacology, 2011, pp. 964-973, vol. 79, No. 6.
Ajmone-Cat et al., "Non-Steroidal Anti-Inflammatory Drugs and Brain Inflammation: Effects on Microglial Functions," Pharmaceuticals, 2010, pp. 1949-1965, vol. 3.
Dello Russo et al., "Inhibition of microglial inflammatory responses by norepinephrine: effects on nitric oxide and interleukin-1β production," Journal of Neuroinflammation, 2004, pp. 1-15, vol. 1, No. 9.
Lu et al., "Resveratrol differentially modulates inflammatory responses of microglia and astrocytes," Journal of Neuroinflammation, 2010, 14 pgs., vol. 7, No. 46.
Chen et al., "Berberine Protects against Neuronal Damage via Suppression of Glia-Mediated Inflammation in Traumatic Brain Injury," PLoS One, 2014, e115694, pp. 1-30, vol. 9, No. 12.
Office Action from related EP Application No. 10736929.0, dated Apr. 6, 2017; 4 pgs.
Office Action from related Canadian Application No. 2,768,199, dated May 18, 2017; 4 pgs.
Office Action from related Canadian Application No. 2,768,236, dated Dec. 7, 2016; 3 pgs.
Patent Examination Report No. 1 from related Australian Application No. 2010273253, dated Jan. 31, 2014; 5 pgs.
Office Action from related Canadian Application No. 2,768,236, dated Jul. 11, 2017; 3 pgs.
Office Action from related U.S. Appl. No. 14/814,580, dated Mar. 8, 2018; 20 pgs.
Office Action from related U.S. Appl. No. 14/814,580, dated Aug. 10, 2017; 15 pgs.
Office Action from related U.S. Appl. No. 14/814,580, dated Jan. 27, 2017; 29 pgs.
McCormack et al., "Liver surgery in the presence of cirrhosis and steatosis: Is morbidity increased?," Patient Safety in Surgery, 2008, 9 pgs., vol. 2, No. 8.
Smith et al., "Doxycycline Suppression of Ischemia-Reperfusion-Induced Hepatic Injury," Inflammation, 1994, pp. 193-201, vol. 18, No. 2.
Yrjanheikki et al., "Tetracyclines inhibit microglial activation and are neuroprotective in global brain ischemia," PNAS, 1998, pp. 15769-15774, vol. 95.
Schafer et al., "Failure is an option: learning from unsuccessful proof-of-concept trials," Drug Discovery Today, 2008, pp. 913-916, vol. 13, Nos. 21-22.
Horig et al., "From bench to clinic and back: Perspective on the 1st IQPC Translational Research conference," Journal of Translational Medicine, 2004, 8 pgs., vol. 2, No. 44.
Shaker et al., "The novel TLR9 antagonist COV08-0064 protects from ischemia/reperfusion injury in non-steatotic and steatotic mice livers," Biochemical Pharmacology, 2016, pp. 90-101, vol. 112.
Kotzampassi et al., "Naloxone: a potent protective agent in ischemia—reperfusion—induced liver injury," Annals of Gastroenterology, 2005, pp. 420-426, vol. 18. No. 4.
Ebrahimkhani et al., "Naltrexone, an opioid receptor antagonist, attenuates liver fibrosis in bile duct ligated rats," Gut, 2006, pp. 1606-1616, vol. 55.
Office Action from related EP Application No. 10805351.3, dated Feb. 13, 2018; 7 pgs.
Gilbert et al., "Pharmacological characterization of dihydromorphine, 6-acetyldihydromorphine and dihydroheroin analgesia and their differentiation from morphine," European Journal of Pharmacology, 2004, pp. 123-130, vol. 492, Nos. 2-3.
Kawai et al., "Design, synthesis, and structure-activity relationship of novel opioid k-agonists," Bioorganic & Medicinal Chemistry, 2008, pp. 9188-9201, vol. 16, No. 20.
Fuerst et al., "The Pharmacological Significance of the Spatial Orientation of C-6-OH Group in Ring C of Morphine," Regulatory Peptides, 1994, pp. 99-100, vol. 54, No. 1.
Olsen et al., "Conjugate Addition Ligands of Opioid Antagonists. Methacrylate Esters and Ethers of 6α- and 6β-Naltrexol," Journal of Medicinal Chemistry, 1990, pp. 737-741, vol. 33, No. 2.
Maurer et al., "Screening Procedure for the Detection of Opioids, other Potent Analgesics and their Metabolites in Urine using a Computerized Gas Chromatographic-Mass Spectrometric Technique," Fresenius' Zeitschrift fuer Analytische Chemie, 1984, pp. 42-52, vol. 317, No. 1.
Simon et al., "Stereoselective Synthesis of β-Naltrexol, β-Naloxol, β-Naloxamine, β-Naltrexamine and Related Compounds by the Application of the Mitsunobu Reaction," Tetrahedron, 1994, pp. 9757-9768, vol. 50, No. 32.
Mykkanen et al., "GCD Quantitation of Opiates as Propionate Derivatives in Blood," Journal of Analytical Toxicology, 2000, pp. 122-126, vol. 24, No. 2.
Aceto et al., "Stereoselective μ- and σ-opioid receptor-related antinociception and binding with (+)-thebaine," European Journal of Pharmacology, 1999, pp. 143-147, vol. 365.
Iijima et al., "Studies in the (+)-Morphinan Series. 4. A Markedly Improved Synthesis of (+)-Morphine," Journal of Organic Chemistry, 1978, pp. 1462-1463, vol. 43, No. 7.
Mahmood et al., "56 Aacetaminophen Hepatotoxicity Is Dependent on TLR9 and Can Be Reduced by a TLR9 Antagonist," Gastroenterology, 2008, p. A-752, vol. 134, No. 4.
Patent Examination Report No. 1 from related Australian Application No. 2010357625, dated Mar. 21, 2014; 7 pgs.
STN International, Morphinan-3, 6, 14-triol, 17-(cyclopropylmethyl)-4,5-epoxy-, (5b,9a,13a,14a)-, File Registry [online], Jul. 6, 2009 [retrieved on Feb. 24, 2015], CAS Registry No. 1160816-11-4, 2 pgs.
Office action from related Japanese Application No. 2012-520805, dated Mar. 19, 2015; 15 pgs.
Office action from related Japanese Application No. 2012-520805, dated Jun. 25, 2014; 13 pgs.
Office action from related Japanese Application No. 2013-519642, dated Jun. 30, 2015; 5 pgs.
Examination report from related European Application No. 10736929.0, dated Sep. 30, 2014; 11 pgs.
Examination report from related European Application No. 10805351.3, dated Sep. 26, 2014; 10 pgs.
International Search Report and Written Opinion from related International Application No. PCT/US2010/042210, dated Nov. 5, 2010; 17 pgs.
International Search Report and Written Opinion from related International Application No. PCT/US2010/061699, dated Aug. 17, 2011; 14 pgs.
Zhao et al. "Antinociceptive and free radical scavenging activities of alkaloids isolated from Lindera angustifolia Chen," Journal of Ethnopharmacology, 2006, pp. 408-413, vol. 106, No. 3.

(56) References Cited

OTHER PUBLICATIONS

Watkins et al., "The "Toll" of Opioid-Induced Glial Activation: Improving the Clinical Efficacy of Opioids by Targeting Glia," Trends in Pharmacological Sciences, 2009, pp. 581-591, vol. 30, No. 11.

Hellewell et al., "A sigma-like binding site in rat pheochromocytoma (PC12) cells: decreased affinity for (+)-benzomorphans and lower molecular weight suggest a different sigma receptor form from that of guinea pig brain," Brain Research, 1990, pp. 244-253, vol. 527, No. 2.

Ye et al., "Synthesis and anti-inflammatory analgesic activities of sinomenine derivatives," Yao Hsueh Hsueh Pao—Acta Pharmaceutica Sinca, Yaoxue Xuebao, CN, 2004, pp. 180-183, vol. 39, No. 3. (Abstract Only).

Iijima et al., "Studies in the (+)-Morphinan Series. 5. Synthesis and Biological Properties of (+)-Naloxone," Journal of Medicinal Chemistry, 1978, pp. 398-400, vol. 21, No. 4.

Kitamura et al., "General Asymmetric Synthesis of Isoquinoline Alkaloids, Enantioselective Hydrogenation of Enamides Catalyzed by BINAP-Ruthenium(II) Complexes," Journal of Organic Chemistry, 1994, pp. 297-310, vol. 59, No. 2.

Liu et al., "Inhibition of (S)-armepavine from Nelumbo nucifera on autoimmune disease of MRL/MpJ-Ipr/Ipr mice," European Journal of Pharmacology, 2006, pp. 270-279, vol. 531.

Fialip et al., "Study of the Antinociceptive Effect of Tetrahydro-Papaveroline Derivatives: Interactions With Opioids," Life Sciences, 1996, pp. PL133-PL139, vol. 59, No. 11.

Thummel and Shen, Appendix II, "Design and Optimization of Dosage Regimens: Pharmacokinetic Data," Goodman & Gilman's the Pharmacological Basis of Therapeutics, Tenth Edition, 2001, pp. 1917-2023.

Goodman & Gilman's The Pharmacological Basis of Therapeutics, Tenth Edition, 2001, Index and Chapters 19 and 20, "Drugs and the Treatment of Psychiatric Disorders," pp. 475-493.

Hutchinson et al., "Non-stereoselective reversal of neuropathic pain by naloxone and naltrexone: involvement of toll-like receptor 4 (TLR4)," European Journal of Neuroscience, 2008, pp. 20-29, vol. 28.

Hutchinson et al., "Opioid-Induced Glial Activation: Mechanisms of Activation and Implications for Opioid Analgesia, Dependence, and Reward," The Scientific World Journal, 2007, pp. 98-111, vol. 7(S2).

Iliev et al., "Neuronal injury mediated via stimulation of microglial toll-like receptor-9 (TLR9)," The FASEB Journal, 2004, pp. 412-414, vol. 18.

Kielian, "Toll-Like Receptors in Central Nervous System Glial Inflammation and Homeostasis," Journal of Neuroscience Research, 2006, pp. 711-730, vol. 83.

Liu et al., "Naloxone Protects Rat Dopaminergic Neurons against Inflammatory Damage through Inhibition of Microglia Activation and Superoxide Generation," The Journal of Pharmacology and Experimental Therapeutics, 2000, pp. 607-617, vol. 293, No. 2.

Liu et al., "Role of Microglia in Inflammation-Mediated Neurodegenerative Diseases: Mechanisms and Strategies for Therapeutic Intervention," The Journal of Pharmacology and Experimental Therapeutics, 2003, pp. 1-7, vol. 304, No. 1.

Song et al., "The involvement of glial cells in the development of morphine tolerance," Neuroscience Research, 2001, pp. 281-286, vol. 39.

Watkins et al., "Glia as the "bad guys": Implications for improving clinical pain control and the clinical utility of opioids," Brain, Behavior, and Immunity, 2007, pp. 131-146, vol. 21.

Wu et al., "Antianalgesia: Stereoselective Action of dextro-Morphine over levo-Morphine on Glia in the Mouse Spinal Cord," The Journal of Pharmacology and Experimental Therapeutics, 2007, pp. 1101-1108, vol. 314, No. 3.

Office action from related Canadian Application No. 2,768,236, dated Apr. 25, 2016; 4 pgs.

Office action from related EP Application No. 10 736 929.0, dated Jul. 12, 2016; 9 pgs.

Office action from related EP Application No. 10 805 351.3, dated Jul. 13, 2016; 8 pgs.

Office action from related Canadian Application No. 2,768,199, dated Sep. 14, 2016; 4 pgs.

Office action from related Japanese Application No. 2013-519642, dated Nov. 7, 2014; 20 pgs.

Final Office action dated Sep. 27, 2018 from related U.S. Appl. No. 14/814,580, 15 pp.

Bockaert, Molecular tinkering of G protein-coupled receptors: an evolutionary success, The EMBO Journal, 1999, vol. 18, No. 7, pp. 1723-1729.

Rothstein, Marshak-Rothstein AToll-like receptors in systemic autoimmune disease, Nat Rev Immunol, Dec. 2006, vol. 6, pp. 823-835.

Sigma-Aldrich, β-Naltrexamine dihydrochloride Product Description, downloaded from https://www.sigmaaldrich.com/catalog/product/sigma/sml1397?lang=en&region=US, Aug. 15, 2019, 3 pp.

Wang et al., "Inverse agonists and neutral antagonists at µ opioid receptor (MOR): possible role of basal receptor signaling in narcotic dependence," J. Neurochem., 2001, 77:1590-1600.

\* cited by examiner

| Two-way ANOVA | |
|---|---|
| Interaction | P = 0.9642 |
| Drug Factor | P < 0.0001 |
| Time Factor | P < 0.0001 |
| S v M @ 51hrs P < 0.05 | |
| S v H @ 3hrs P < 0.01 | |

| Two-way ANOVA | |
|---|---|
| Interaction | P = 0.0087 |
| Drug Factor | P < 0.0001 |
| Time Factor | P < 0.0001 |
| S v H @ 3hrs | P < 0.001 |
| S v H @ 51hrs | P < 0.001 |

| Two-way ANOVA | |
|---|---|
| Interaction | P = 0.9996 |
| Drug Factor | P = 0.0086 |
| Time Factor | P = 0.0614 |
| No post hoc significance | |

FIG. 8A   *P < 0.05

(+)-MORPHINANS AS ANTAGONISTS OF TOLL-LIKE RECEPTOR 9 AND THERAPEUTIC USES THEREOF

CROSS REFERENCE TO RELATED APPLICATIONS

This application is a continuation of U.S. patent application Ser. No. 12/975,407, filed Dec. 22, 2010, which is a continuation-in-part of U.S. patent application Ser. No. 12/837,545, filed Jul. 16, 2010, which claims the benefit of U.S. Provisional Application No. 61/226,015, filed Jul. 16, 2009, and U.S. Provisional Application No. 61/286,877, filed Dec. 16, 2009, each of which is hereby incorporated by reference in its entirety.

FIELD OF THE INVENTION

The present invention generally relates to compounds and methods for treating pain, inflammation, and other disorders. In particular, the invention relates to (+)-morphinan compounds comprising Toll-like receptor 9 (TLR9) antagonist activity and methods of using the compounds to treat conditions associated with pain and inflammation.

BACKGROUND OF THE INVENTION

Activated glial cells contribute to the development and maintenance of several disease states. Of particular interest is the negative impact of activated glial cells in the areas of chronic and acute pain, inflammatory disorders, autoimmune disorders, neurodegenerative disorders, and cancer. Glial cells have been shown to express numerous Toll-like receptors (TLRs), which are a family of highly conserved transmembrane proteins of high functional importance in the innate immune system. TLRs are activated by pathogen-associated molecular patterns (PAMPs) such as lipopolysaccharide (LPS) from bacterial cell walls, unmethylated CpG-containing DNA of viruses, and a wide variety of additional microbial components. Activation of TLRs in the central nervous system is known to initiate protective pro-inflammatory signaling cascades as part of the first line of defense against invading pathogens. Additionally, it has been reported that chronic administration of morphine or other opioid-receptor agonists activates glial cells, causing the release of pro-inflammatory factors that counter the pain-relieving effects of the opioid. Activated glial cells have also been shown to play a role in driving chronic pain states such as neuropathic pain. Given these newly identified roles for glial cells in pain, there is a need for the development of clinically useful agents that target glial cell activation as a means of pain control.

SUMMARY OF THE INVENTION

The present invention provides (+)-morphinan compounds that inhibit the activation of Toll-like receptor 9 (TLR9), and consequently block glial cell activation. The compounds of the invention, therefore, may be used to treat conditions such as traumatic pain, neuropathic pain, inflammatory disorders, acetaminophen toxicity, autoimmune disorders, neurodegenerative disorders, and cancer.

One aspect of the invention encompasses a compound comprising Formula (IIa) or a pharmaceutically acceptable salt thereof:

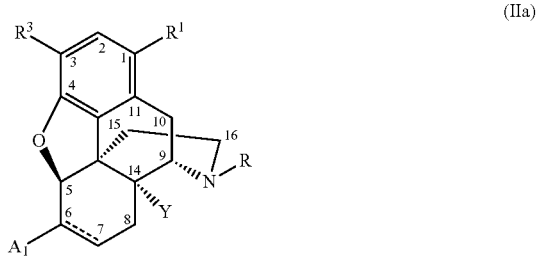

(IIa)

wherein:
R is chosen from hydrogen, alkyl, alkenyl, and methylcycloalkyl;
$R^1$ is chosen from hydrogen, aryl, and heteroaryl;
$R^3$ is chosen from hydroxy, alkoxy, and aryloxy;
$A_1$ is chosen from hydroxy, keto, $C_2$-$C_6$ alkoxy, acyloxy, aryloxy, amino, alkylamine, hydroxyalkylamine, carboxylalkylamine, alkylcarboxylalkylamine, and arylamine; provided, however, that when $A_1$ is keto, $R^1$ is other than hydrogen; when $A_1$ is hydroxy, R is other than methyl or allyl; when $A_1$ is hydroxy, Y is other than hydroxy; or when $A_1$ is an amine, Y is other than hydroxy;
Y is chosen from hydrogen and hydroxy; and
the dashed line represents an optional double bond.

Another aspect of the invention provides a compound comprising Formula (IIIa) or a pharmaceutically acceptable salt thereof:

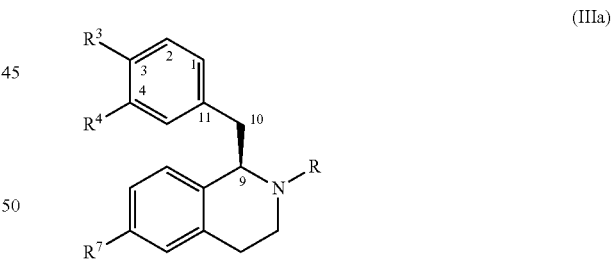

(IIIa)

wherein:
R is chosen from $C_2$-$C_6$ alkyl, alkenyl, methylcycloalkyl, methylaryl, acylalkyl, acylcycloalkyl, acylaryl, acyloxy, acyloxyalkyl, acyloxyaryl, alkoxy, and alkoxyalkyl; and
$R^3$, $R^4$, and $R^7$ are independently chosen from hydroxy, alkoxy, aryloxy, and acyloxy.

Still another aspect of the invention provides method for treating a pain condition in a subject in need thereof. The method comprises administering to the subject a compound comprising Formula (IIa) or a pharmaceutically acceptable salt thereof:

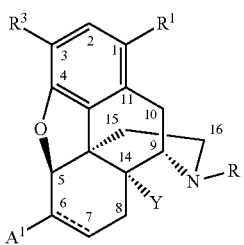

(IIa)

wherein:
R is chosen from hydrogen, methyl, alkyl, alkenyl, allyl, methylcycloalkyl, methylcyclopropyl, methylcyclobutyl, methylaryl, methylphenyl, acyl, acylalkyl, acylcycloalkyl, acylcyclopropyl, acylcyclobutyl, acylaryl, acylphenyl, acyloxy, acyloxyalkyl, acyloxyaryl, acyloxyphenyl, alkoxy, and alkoxyalkyl;

$R^1$ is chosen from hydrogen, halo, hydroxy, alkoxy, alkoxyalkyl, alkoxyalkenyl, aryloxy, alkyl, alkenyl, aryl, heteroaryl, and amine;

$R^3$ is chosen from hydroxy, alkoxy, aryloxy, acyl, acyloxy, and protected hydroxy;

$A_1$ is chosen from hydrogen, hydroxy, keto, alkoxy, acyl, acyloxy, amino, amide, alkylamine, hydroxyalkylamine, carboxylalkylamine, alkylcarboxylalkylamine, arylamine, alkyl, alkenyl, aryl, substituted alkyl, substituted alkenyl, and substituted aryl; provided, however, that when $A_1$ is keto, $R^1$ is other than hydrogen;

Y is chosen from hydrogen, hydroxy, alkoxy, and protected hydroxy; and the dashed line represents an optional double bond.

A further aspect of the present invention encompasses a method for treating a pain condition in a subject in need thereof. The method comprises administering to the subject a compound comprising Formula (IIIa) or a pharmaceutically acceptable salt thereof:

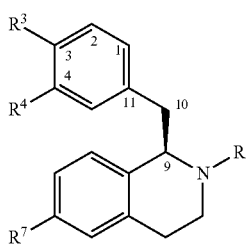

(IIIa)

wherein:
R is chosen from hydrogen, methyl, alkyl, alkenyl, allyl, methylcycloalkyl, methylcyclopropyl, methylcyclobutyl, methylaryl, methylphenyl, acyl, acylalkyl, acylcycloalkyl, acylcyclopropyl, acylcyclobutyl, acylaryl, acylphenyl, acyloxy, acyloxyalkyl, acyloxyaryl, acyloxyphenyl, alkoxy, and alkoxyalkyl; and $R^3$, $R^4$, and $R^7$ are independently chosen from hydrogen, hydroxy, alkoxy, aryloxy, acyloxy, amine, halo, and protected hydroxy.

Yet another aspect of the invention provides a pharmaceutical composition comprising a compound comprising Formula (IV) or a pharmaceutically acceptable salt thereof and a (+)-morphinan or a pharmaceutically acceptable salt thereof, provided that the (+)-morphinan is other than dextrorphan or a derivative thereof. The compound comprising Formula (IV) has the following structure:

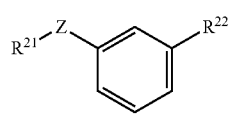

(IV)

wherein:
$R^{21}$ is chosen from hydrogen, hydrocarbyl, and substituted hydrocarbyl;
$R^{22}$ is chosen from hydrocarbylamine and substituted hydrocarbylamine; and
Z is chosen from oxygen and sulfur.

Another embodiment encompasses a method for treating a pain condition in a subject in need thereof. The method comprises administering to the subject a compound comprising Formula (IV) or a pharmaceutically acceptable salt thereof and a (+)-morphinan or a pharmaceutically acceptable salt thereof, provided that the (+)-morphinan is other than dextrorphan or a derivative thereof. The compound comprising Formula (IV) has the following structure:

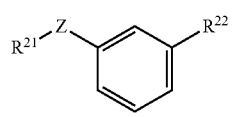

(IV)

wherein:
$R^{21}$ is chosen from hydrogen, hydrocarbyl, and substituted hydrocarbyl;
$R^{22}$ is chosen from hydrocarbylamine and substituted hydrocarbylamine; and
Z is chosen from oxygen and sulfur.

Other aspects and features of the invention are detailed below.

DESCRIPTION OF THE FIGURES

FIG. 1A presents TLR2 antagonist screening in which TLR2 was stimulated with HKLM at $10^8$ cell/ml. FIG. 1B presents TLR3 antagonist screening in which TLR3 was stimulated with poly(I:C) at 1 μg/ml. FIG. 1C presents TLR4 antagonist screening in which TLR4 was stimulated with LPS at 100 ng/ml. FIG. 1D presents TLR5 antagonist screening in which TLR5 was stimulated with Flagellin at 100 ng/ml. FIG. 1E presents TLR7 antagonist screening in which TLR7 was stimulated with CL097 at 1 μg/ml. FIG. 1F presents TLR8 antagonist screening in which TLR8 was stimulated with CL075 at 1 μg/ml. FIG. 1G presents TLR9 antagonist screening in which TLR9 was stimulated with CpG ODN 2006 at 100 ng/ml.

FIG. 1A presents data for the left (affected) paw. FIG. 2B presents data for the right (unaffected) paw. *p<0.05, p<0.01, *p<0.001 vs. vehicle.

FIG. 3A shows the von Frey score on days 1, 4 and 14 for ipsilateral paws in each treatment group. FIG. 3B presents the von Frey score on days 1, 4 and 14 for contralateral paws in each treatment group.

FIG. 4A presents responses to an ultra low dose of compound II-25 in ipsilateral paws. FIG. 4B presents responses to a low dose of compound II-25 in ipsilateral paws. FIG. 4C presents responses to a medium dose of compound II-25 in ipsilateral paws. FIG. 4D presents responses to a high dose of compound II-25 in ipsilateral paws. FIG. 4E presents responses to an ultra low dose of compound II-25 in contralateral paws. FIG. 4F presents responses to a low dose of compound II-25 in contralateral paws. FIG. 4G presents responses to a medium dose of compound II-25 in contralateral paws. FIG. 4H presents responses to a high dose of compound II-25 in contralateral paws.

FIG. 5A presents AUC data from ipsilateral paws. FIG. 5B presents AUC data from contralateral paws.

FIG. 6A presents responses to an ultra low dose of compound II-93 in ipsilateral paws. FIG. 6B presents responses to a low dose of compound II-93 in ipsilateral paws. FIG. 6C presents responses to a medium dose of compound II-93 in ipsilateral paws. FIG. 6D presents responses to a high dose of compound II-93 in ipsilateral paws. FIG. 6E presents responses to an ultra low dose of compound II-93 in contralateral paws. FIG. 6F presents responses to a low dose of compound II-93 in contralateral paws. FIG. 6G presents responses to a medium dose of compound II-93 in contralateral paws. FIG. 6H presents responses to a high dose of compound II-93 in contralateral paws.

FIG. 7A presents AUC data from ipsilateral paws. FIG. 7B presents AUC data from contralateral paws.

FIGS. 8A-8B illustrate that (+)-naloxone (i.e., COV008-0001) did not affect acetaminophen-induced hepatotoxicity. FIG. 8A presents liver histology scores in control and treated groups. FIG. 8B presents alanine transaminase (ALT) activity in control and treated groups.

FIG. 9A presents liver histology scores in control and treated groups. FIG. 9B presents alanine transaminase (ALT) activity in control and treated groups.

DETAILED DESCRIPTION OF THE INVENTION

Figure 1A:
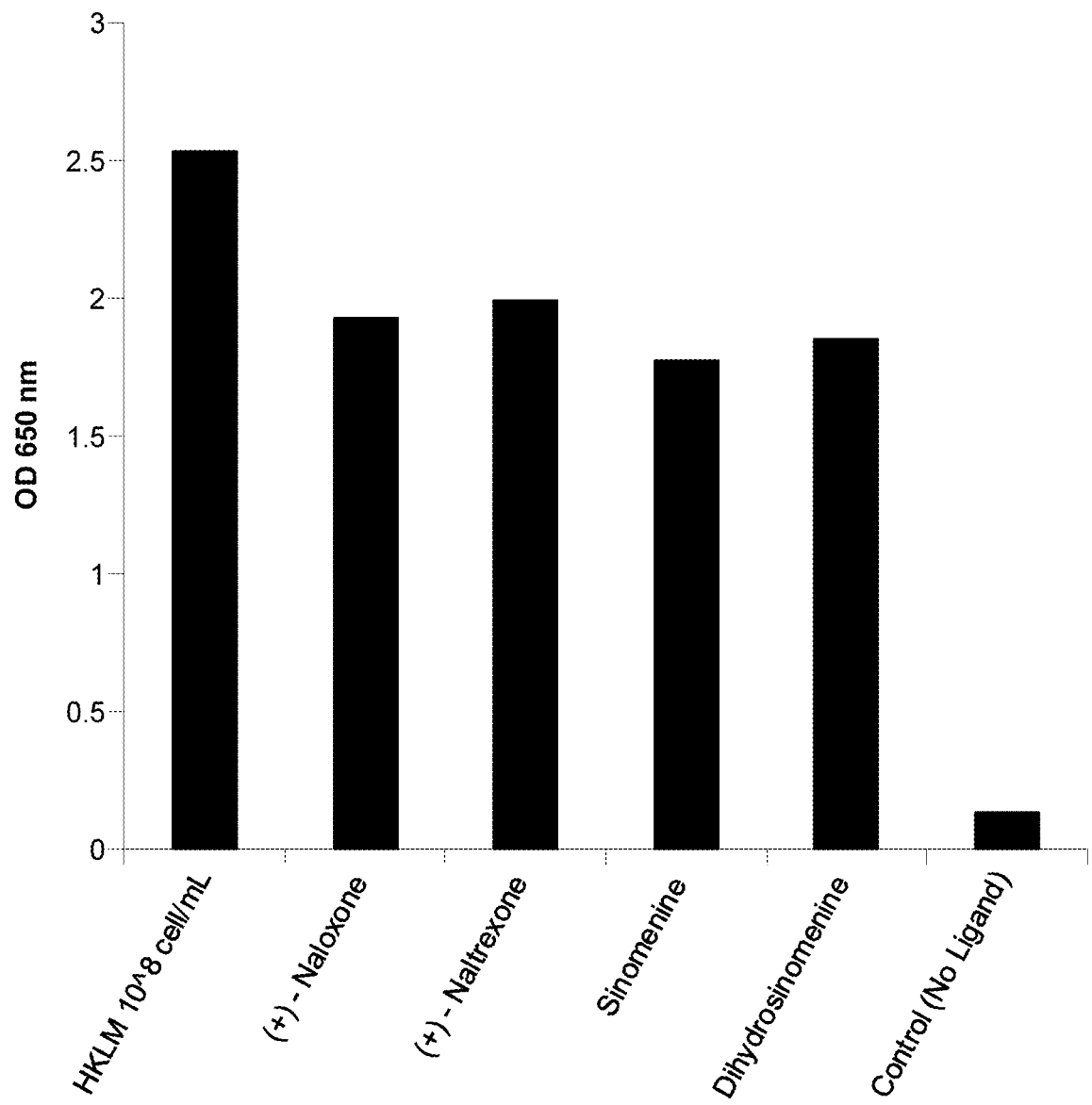
FIGS. 1A-1G present Toll-like receptor (TLR) antagonist screenings. Each figure presents the results for a particular TLR. Plotted is the activity of a secreted alkaline phosphatase reporter system in optical density (OD) at 650 nm for each treatment condition, which was tested in duplicate. All agents were tested at 10 μM.
Figure 1B:
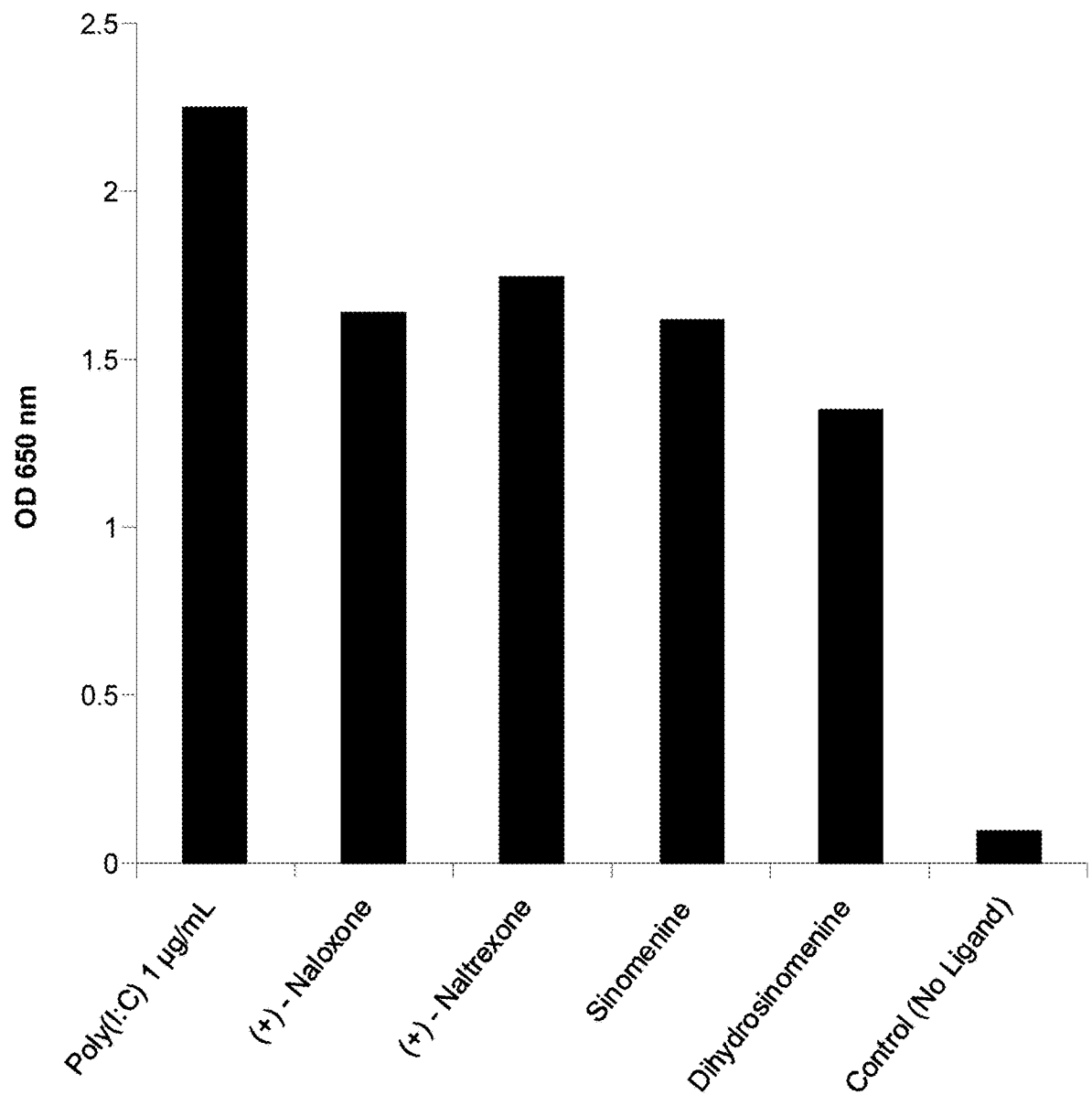
Figure 1C:
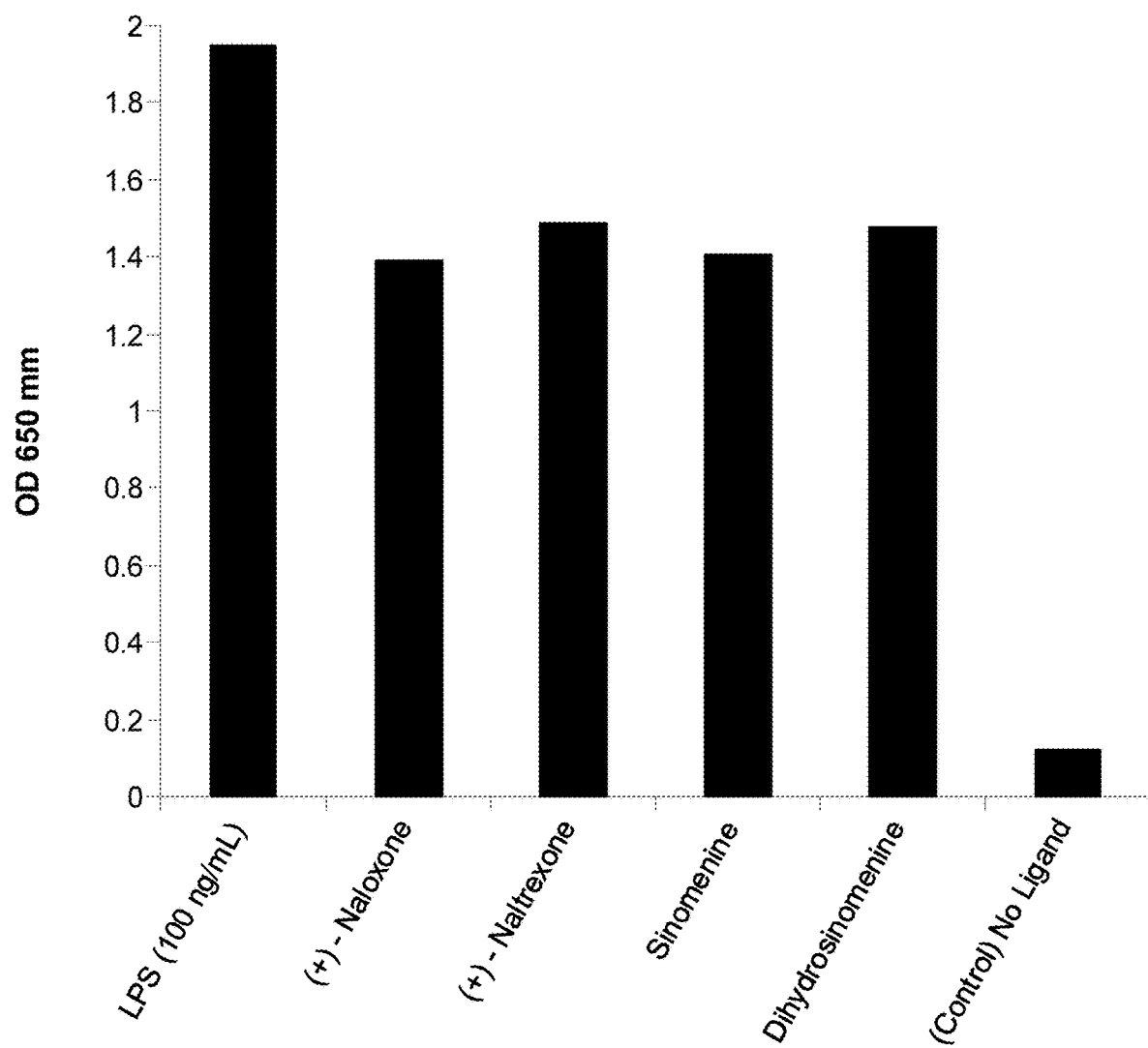
Figure 1D:
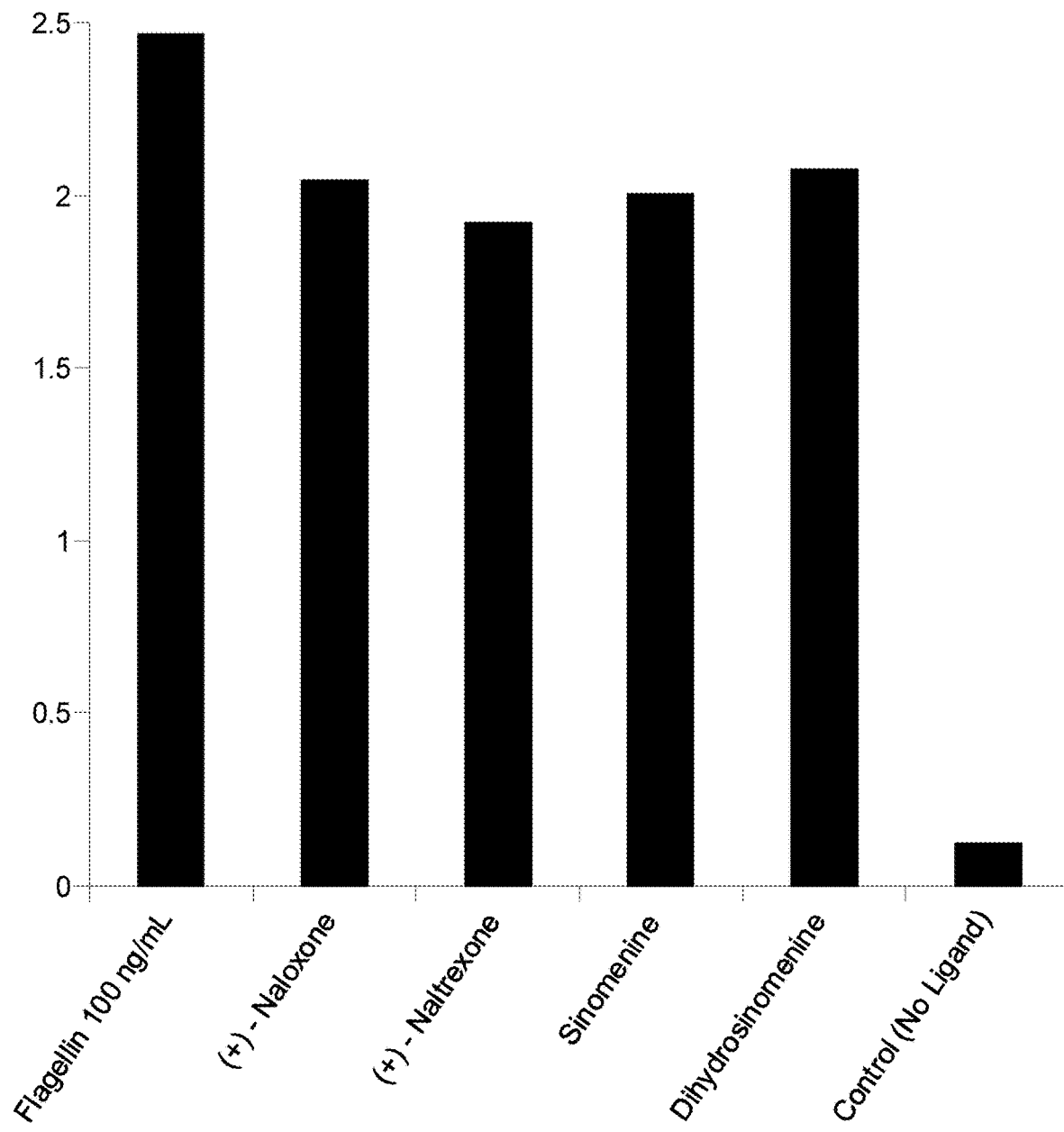
Figure 1E:
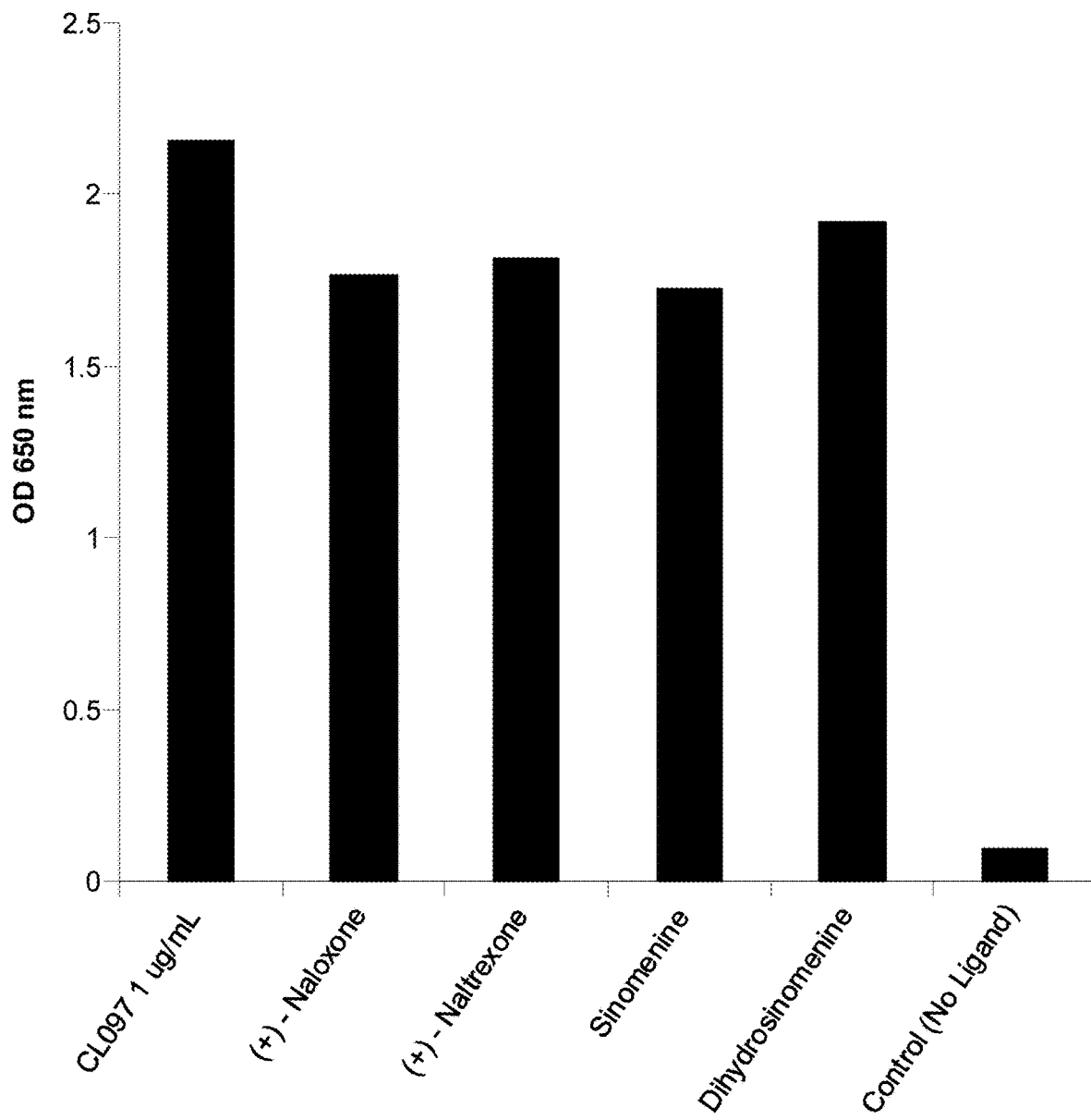
Figure 1F:
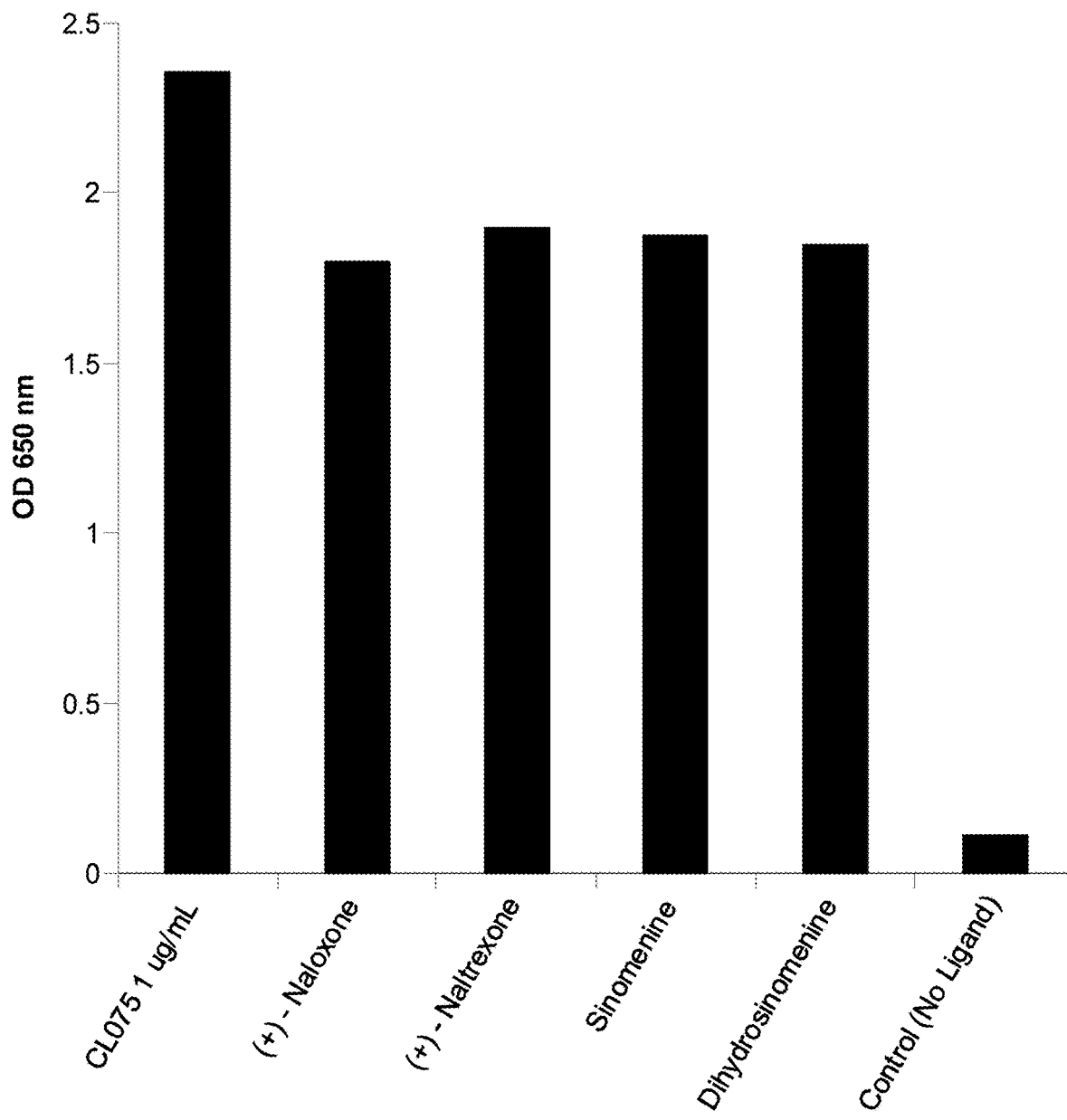

It has been discovered that certain (+)-morphinans block the activation of TLR9 and, consequently, the activation of glial cells. Thus, (+)-morphinans comprising TLR9 antagonist activity may be used to treat pain, as well as other conditions associated with pain and inflammation. It has also been discovered that the inhibition of TLR9 activation may be used as a screening tool to identify (+)-morphinans that may be therapeutically effective in treating conditions such as traumatic pain, neuropathic pain, inflammatory disorders, acetaminophen toxicity, autoimmune disorders, neurodegenerative disorders, and cancer. Accordingly, the present invention provides (+)-morphinans comprising TLR9 antagonist activity, methods for inhibiting the activation of TLR9, screening methods for identifying therapeutically effective (+)-morphinans, and methods of using the (+)-morphinans comprising TLR9 antagonist activity to treat conditions such as traumatic pain, neuropathic pain, inflammatory disorders, acetaminophen toxicity, autoimmune disorders, neurodegenerative disorders, and cancer.

(I) (+)-Morphinans Comprising TLR9 Antagonist Activity (a) Compounds Comprising Formula (I)

One aspect of the present invention is the provision of (+)-morphinans comprising TLR9 antagonist activity. In one embodiment, the (+)-morphinan may be a compound comprising Formula (I) or a pharmaceutically acceptable salt thereof:

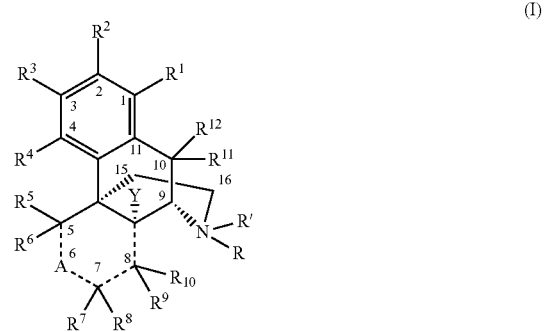

wherein:

A is chosen from {-}C(=O){-}, {-}C(S){-}, {-}C(=CH$_2$){-}, {-}CH(A$_1$){-}, and {-}C(A$_1$)(A$_2$){-};

A$_1$ and A$_2$ are independently chosen from hydrogen, alkyl, alkenyl, alkoxy, acyloxy, aryl, heteroaryl, hydroxy, hydroxyalkyl, polyhydroxyalkyl, amine, and amide, wherein when both A$_1$ and A$_2$ are present, together they may form a carbocyclic ring or heterocyclic ring;

R and R' are independently chosen from hydrogen, hydroxy, amine, hydrocarbyl, and substituted hydrocarbyl, wherein R' is optional, as represented by the dashed line;

R$^1$, R$^2$, R$^3$, R$^4$, R$^5$, R$^6$, R$^7$, R$^8$, R$^9$, R$^{10}$, R$^{11}$, and R$^{12}$ are independently chosen from hydrogen, hydroxy, amine, halo, hydrocarbyl, and substituted hydrocarbyl, wherein R$^7$ and A$_1$ may together form a ring or a ring system chosen from carbocyclic, heterocyclic, aryl, heteroaryl, and combinations thereof;

Y is chosen from hydrogen, hydroxy, alkoxy, acyloxy, amine, and amide; and the dashed lines between the carbons atoms at positions 5 and 6, 6 and 7, 7 and 8, and 8 and 14 represent carbon-carbon single bonds, carbon-carbon double bonds, or combinations thereof, provided that if there is a double bond between the carbons at positions 5 and 6 then only one of $R^5$ or $R^6$ is present, if there is a double bond between the carbons at 6 and 7 then only one of $R^7$ or $R^8$ is present, if there is a double bond between the carbons at 7 and 8 then only one of $R^7$ or $R^8$ is present and only one of $R^9$ or $R^{10}$ is present, and if there is a double bond between the carbons at 8 and 14 then only one of $R^9$ or $R^{10}$ is present and Y is not present.

In one iteration of this embodiment, R, $R^1$, $R^2$, $R^3$, $R^4$, $R^5$, $R^6$, $R^7$, $R^8$, $R^9$, $R^{10}$, $R^{11}$, and $R^{12}$ are independently chosen from hydrogen, hydroxy, alkyl, alkenyl, alkynyl, aminoalkyl, alkoxyalkyl, aralkyl, cycloalkyl, hydroxyalkyl, acyloxy, alkoxy, haloalkoxyl, aryl, amine, amide, and halo.

In another iteration, $R^2$, $R^6$, $R^8$, $R^9$, $R^{10}$, $R^{11}$, and $R^{12}$ are hydrogen; R is chosen from hydrogen, methyl, alkyl, alkenyl, allyl, methylcycloalkyl, methylcyclopropyl, methylcyclobutyl, methylaryl, methylphenyl, acyl, acylalkyl, acylcycloalkyl, acylcyclopropyl, acylcyclobutyl, acylaryl, acylphenyl, acyloxy, acyloxyalkyl, acyloxyaryl, acyloxyphenyl, alkoxy, and alkoxyalkyl; $R^1$ is chosen from hydrogen, halo, alkyl, alkenyl, alkoxyalkyl, alkoxyalkenyl, aryl, heteroaryl, and furanyl; $R^3$ and $R^4$ are independently chosen from hydroxy, alkoxy, methoxy, acyloxy, and protected hydroxy; $R^7$ is chosen from hydroxy, alkoxy, methoxy, acyloxy, protected hydroxy, hydrocarbyl, and substituted hydrocarbyl, wherein $R^7$ and $A^1$ may together form an indolyl ring; and Y is hydrogen or hydroxy.

(b) Compounds Comprising Formula (II)

In another embodiment, the (+)-morphinan may be a compound comprising Formula (II) or a pharmaceutically acceptable salt thereof:

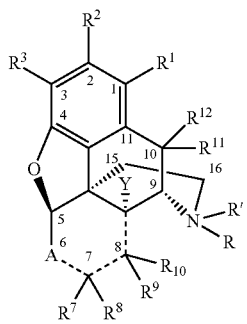

(II)

wherein:
A is chosen from $\{-\}C(=O)\{-\}$, $\{-\}C(S)\{-\}$, $\{-\}C(=CH_2)\{-\}$, $\{-\}CH(A_1)\{-\}$, and $\{-\}C(A_1)(A_2)\{-\}$;

$A_1$ and $A_2$ are independently chosen from hydrogen, alkyl, alkenyl, alkoxy, acyloxy, aryl, heteroaryl, hydroxy, hydroxyalkyl, polyhydroxyalkyl, amine, and amide, wherein when both $A_1$ and $A_2$ are present, together they may form a carbocyclic ring or heterocyclic ring;

R and R' are independently chosen from hydrogen, hydroxy, amine, hydrocarbyl, and substituted hydrocarbyl, wherein R' is optional, as represented by the dashed line;

$R^1$, $R^2$, $R^3$, $R^7$, $R^8$, $R^9$, $R^{10}$, $R^{11}$, and $R^{12}$ are independently chosen from hydrogen, hydroxy, amine, halo, hydrocarbyl, and substituted hydrocarbyl, wherein $R^7$ and $A^1$ may together form a ring or a ring system chosen from carbocyclic, heterocyclic, aryl, heteroaryl, and combinations thereof;

Y is chosen from hydrogen, hydroxy, alkoxy, acyloxy, amine, and amide;

the dashed lines between the carbons atoms at positions 6 and 7, 7 and 8, and 8 and 14 represent carbon-carbon single bonds, carbon-carbon double bonds, or combinations thereof, provided that if there is a double bond between the carbons at 6 and 7 then only one of $R^7$ or $R^8$ is present, if there is a double bond between the carbons at 7 and 8 then only one of $R^7$ or $R^8$ is present and only one of $R^9$ or $R^{10}$ is present, and if there is a double bond between the carbons at 8 and 14 then only one of $R^9$ or $R^{10}$ is present and Y is not present; and the carbons at positions 6 and 14 may be linked by a moiety chosen from ether, alkyl, alkenyl, substituted alkyl, and substituted alkenyl.

In one iteration of this embodiment, R, $R^1$, $R^2$, $R^3$, $R^7$, $R^8$, $R^9$, $R^{10}$, $R^{11}$, and $R^{12}$ are independently chosen from hydrogen, hydroxy, alkyl, alkenyl, alkynyl, aminoalkyl, alkoxyalkyl, aralkyl, cycloalkyl, hydroxyalkyl, acyloxy, alkoxy, haloalkoxyl, aryl, amine, amide, and halo.

In another iteration, $R^2$, $R^8$, $R^9$, $R^{10}$, $R^{11}$, and $R^{12}$ are hydrogen; R is chosen from hydrogen, methyl, alkyl, alkenyl, allyl, methylcycloalkyl, methylcyclopropyl, methylcyclobutyl, methylaryl, methylphenyl, acyl, acylalkyl, acylcycloalkyl, acylcyclopropyl, acylcyclobutyl, acylaryl, acylphenyl, acyloxy, acyloxyalkyl, acyloxyaryl, acyloxyphenyl, alkoxy, and alkoxyalkyl; $R^1$ is chosen from hydrogen, halo, alkyl, alkenyl, alkoxyalkyl, alkoxyalkenyl, aryl, heteroaryl, and furanyl; $R^3$ is chosen from hydroxy, alkoxy, methoxy, acyloxy, and protected hydroxy; $R^7$ is chosen from hydroxy, alkoxy, methoxy, acyloxy, protected hydroxy, hydrocarbyl, and substituted hydrocarbyl, wherein $R^7$ and $A_1$ may together form an indolyl ring; and Y is hydrogen or hydroxy.

In preferred embodiments, the (+)-morphinan may be a compound comprising Formula (IIa) or a pharmaceutically acceptable salt thereof:

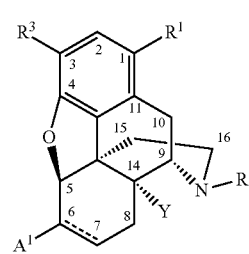

(IIa)

wherein:
R is chosen from hydrogen, alkyl, alkenyl, and methylcycloalkyl;
$R^1$ is chosen from hydrogen, aryl, and heteroaryl;
$R^3$ is chosen from hydroxy, alkoxy, and aryloxy;
$A_1$ is chosen from hydroxy, keto, $C_2$-$C_6$ alkoxy, acyloxy, aryloxy, amino, alkylamine, hydroxyalkylamine, carboxylalkylamine, alkylcarboxylalkylamine, and arylamine; provided, however, that when $A_1$ is keto, $R^1$ is other than hydrogen; when $A_1$ is hydroxy, R is other than methyl or allyl; when $A_1$ is hydroxy, Y is other than hydroxy; or when $A_1$ is an amine, Y is other than hydroxy;
Y is chosen from hydrogen and hydroxy; and
the dashed line represents an optional double bond.

In one exemplary embodiment, the (+)-morphinan may be a compound comprising Formula (IIb) or a pharmaceutically acceptable salt thereof:

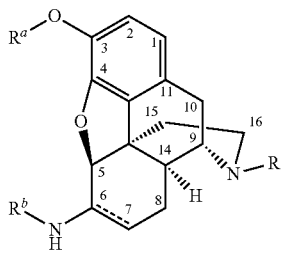

(IIb)

wherein:
R is chosen from hydrogen, methyl, allyl, methylcyclopropyl, and methylcyclobutyl;
$R^a$ is chosen from hydrogen, methyl, ethyl, phenyl, and benzyl;
$R^b$ is chosen from hydrogen, methyl, alkyl, alkylalcohol, and alkylcarboxylalkylester; and
Y is hydrogen.

In one iteration, R is methyl, $R^a$ is methyl, $R^b$ is methylacetylmethylester; and Y is hydrogen. In this iteration, therefore, the (+)-morphinan is compound II-92 in Table 2. In another iteration, R is allyl, $R^a$ is methyl, $R^b$ is propyl; and Y is hydrogen. That is, the (+)-morphinan is compound II-93 in Table 2. In a further iteration, R is allyl, $R^a$ is methyl, $R^b$ is ethylalcohol; and Y is hydrogen. Thus, the (+)-morphinan is compound II-21 in Table 2.

In another exemplary embodiment, the (+)-morphinan may be a compound comprising Formula (IIc) or a pharmaceutically acceptable salt thereof:

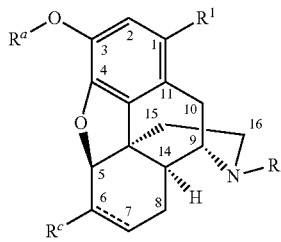

(IIc)

wherein:
R is chosen from hydrogen, methyl, allyl, methylcyclopropyl, and methylcyclobutyl;
$R^1$ is chosen from hydrogen, aryl, heteroaryl, and furanyl;
$R^a$ is chosen from hydrogen, methyl, ethyl, phenyl, and benzyl;
$R^c$ is chosen from hydroxy, $C_2$-$C_6$ alkoxy, and keto; provided, however, that when $R^c$ is keto, $R^1$ is other than hydrogen; when $R^c$ is hydroxy, R is other than methyl or allyl; or when $R^c$ is hydroxy, Y is other than hydroxy;
Y is chosen from hydrogen and hydroxy; and
the dashed line represents an optional double bond.

In one iteration of this embodiment, R is methylcyclopropyl, $R^1$ is hydrogen, $R^a$ is methyl, $R^c$ is hydroxy; and Y is hydrogen. That is, the (+)-morphinan is compound II-25 in Table 2. In yet another iteration, R is allyl, $R^1$ is furanyl, $R^a$ is methyl, $R^c$ is keto; and Y is hydrogen. Thus, the (+)-morphinan is compound II-2 in Table 2.

(c) Compounds Comprising Formula (III)

In still another embodiment, the (+)-morphinan having TLR9 antagonist activity may be a compound comprising Formula (III) or a pharmaceutically acceptable salt thereof:

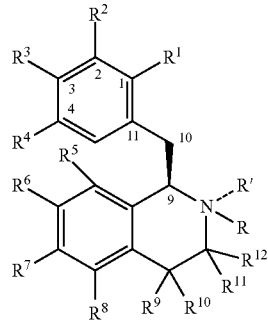

(III)

wherein:
R and R' are independently chosen from hydrogen, hydroxy, amine, hydrocarbyl, and substituted hydrocarbyl, wherein R' is optional, as represented by the dashed line; and
$R^1$, $R^2$, $R^3$, $R^4$, $R^5$, $R^6$, $R^7$, $R^8$, $R^9$, $R^{10}$, $R^{11}$, and $R^{12}$ are independently chosen from hydrogen, hydroxy, amine, halo, hydrocarbyl, and substituted hydrocarbyl.

In one iteration of this embodiment, R, $R^1$, $R^2$, $R^3$, $R^4$, $R^5$, $R^6$, $R^7$, $R^8$, $R^9$, $R^{10}$, $R^{11}$, and $R^{12}$ are independently chosen from hydrogen, hydroxy, alkyl, alkenyl, alkynyl, aminoalkyl, alkoxyalkyl, aralkyl, cycloalkyl, hydroxyalkyl, acyloxy, alkoxy, haloalkoxyl, aryl, amine, amide, and halo.

In another iteration, $R^1$, $R^2$, $R^5$, $R^6$, $R^8$, $R^9$, $R^{10}$, $R^{11}$, and $R^{12}$ are hydrogen; R is chosen from hydrogen, methyl, alkyl, alkenyl, allyl, methylcycloalkyl, methylcyclopropyl, methylcyclobutyl, methylaryl, methylphenyl, acyl, acylalkyl, acylcycloalkyl, acylcyclopropyl, acylcyclobutyl, acylaryl, acylphenyl, acyloxy, acyloxyalkyl, acyloxyaryl, acyloxyphenyl, alkoxy, and alkoxyalkyl; and $R^3$, $R^4$, and $R^7$ are independently chosen from hydroxy, alkoxy, methoxy, acyloxy, and protected hydroxy.

In an exemplary embodiment, the (+)-morphinan may be a compound comprising Formula (IIIa) or a pharmaceutically acceptable salt thereof:

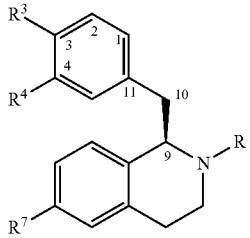

(IIIa)

wherein:
R is chosen from $C_2$-$C_6$ alkyl, alkenyl, methylcycloalkyl, methylaryl, acylalkyl, acylcycloalkyl, acylaryl, acyloxy, acyloxyalkyl, acyloxyaryl, alkoxy, and alkoxyalkyl; and R³, R⁴, and R⁷ are independently chosen from hydroxy, alkoxy, aryloxy, and acyloxy.

In one iteration of this embodiment, R is allyl, R³ is methoxy, R⁴ is hydroxy, and R⁷ is methoxy. That is, the (+)-morphinan is compound III-2 in Table 2.

(d) Pharmaceutically Acceptable Salts

Any of the compounds detailed above in sections (I)(a), (I)(b), and (I)(c) may be provided as a pharmaceutically acceptable salt. The term "pharmaceutically acceptable salt" refers to a salt commonly used to form an alkali metal salt or addition salt of a free acid or a free base. The nature of the salt may vary, provided that it is pharmaceutically acceptable. Suitable pharmaceutically acceptable acid addition salts of compounds of the present invention may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of the present invention include metallic salts made from aluminum, calcium, lithium, magnesium, potassium, sodium and zinc or organic salts made from N, N'-dibenzylethylenediamine, chloroprocaine, choline, diethanolamine, ethylenediamine, meglumine (i.e., N-methylglucamine), and procaine. All of these salts may be prepared by conventional means from the corresponding compound by reacting, for example, the appropriate acid or base with the any of the compounds of the invention.

(e) Stereochemistry

Each of the compounds detailed above in sections (I)(a), (I)(b), and (I)(c) has a (+) orientation with respect to the rotation of polarized light. More specifically, each chiral carbon has an R or an S configuration. As will be appreciated by a skilled artisan, the R or S configuration for a given carbon may change depending on the particular structure of the compound and the compound's substitution pattern.

(II) Pharmaceutical Compositions Comprising a (+)-Morphinan and a Compound Comprising Formula (IV)

Still another aspect of the present invention provides a pharmaceutical composition comprising a (+)-morphinan or a pharmaceutically acceptable salt thereof and a compound comprising Formula (IV) or a pharmaceutically acceptable salt thereof, provided that the (+)-morphinan is other than dextrorphan or a derivative thereof.

(a) Compounds Comprising Formula (IV)

The pharmaceutical composition of the invention comprises a compound comprising Formula (IV) or a pharmaceutically acceptable salt thereof. In general, the compound comprising Formula (IV) may have weak p-opioid receptor agonist activity and/or monoamine reuptake inhibitor activity. The compound comprising Formula (IV) has the following structure:

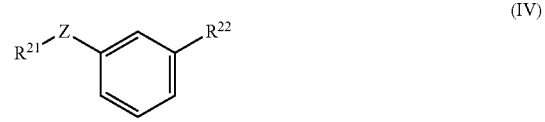

wherein:
R²¹ is chosen from hydrogen, hydrocarbyl, and substituted hydrocarbyl;
R²² is chosen from hydrocarbylamine and substituted hydrocarbylamine; and
Z is chosen from oxygen and sulfur.

In preferred embodiments, R²¹ is chosen from hydrogen, alkyl, and substituted alkyl; R²² is chosen from dialkylaminoalkyl and substituted dialkylaminoalkyl; and Z is oxygen. In one preferred embodiment, R²¹ is chosen from hydrogen and methyl; and R²² is chosen from dimethylamino-ethylmethylpropyl and dimethylamino cyclohexanol. In one preferred embodiment, R²¹ is hydrogen, R²² is dimethylamino-ethyl-methylpropyl, and Z is oxygen (i.e., the compound is tapentadol). In another preferred embodiment, R²¹ is methyl, R²² is dimethylamino cyclohexanol, and Z is oxygen (i.e., the compound is tramadol).

The compound comprising Formula (IV) may be provided as a pharmaceutically acceptable salt. The pharmaceutically acceptable salt may be an acid addition salt or a base addition salt. Acids commonly employed to form acid addition salts include inorganic acids, such as for example, hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutylate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutylate, citrate, lactate, g-hydroxybutylate, glycolate, tartrate, methanesulfonate, propanesulfonate, naphthalene-1-sulfonate, naphthalene-2-sulfonate, mandelate and the like. Base addition salts include those derived from inorganic bases, such as for example, ammonium or alkali or alkaline earth metal hydroxides, carbonates, bicarbonates, and the like. Such bases include sodium hydroxide, potassium hydroxide, ammonium hydroxide, potassium carbonate, sodium carbonate, sodium bicarbonate, potassium bicarbonate, calcium hydroxide, and calcium carbonate.

The compound comprising Formula (IV) may be a (+) enantiomer, a (−) enantiomer, or a combination thereof. Thus, each chiral carbon may have an R or an S configuration.

(b) (+)-Morphinan Compound

The pharmaceutical composition of the invention also comprises a (+)-morphinan or a pharmaceutically acceptable salt thereof.

(i) Compounds Comprising Formula (I)

In one embodiment, the (+)-morphinan may be a compound comprising Formula (I) or a pharmaceutically acceptable salt thereof, as detailed above in section (I)(a); provided however that when $A_1$ is present, it is other than hydrogen, or when both $A_1$ and $A_2$ are present, each is other than hydrogen. Stated another way, the compound comprising Formula (I) is other than dextrorphan or a derivative thereof.

(ii) Compounds Comprising Formula (II)

In another embodiment, the (+)-morphinan may be a compound comprising Formula (II) or a pharmaceutically acceptable salt thereof, as detailed above in section (I)(b).

In preferred embodiments, the (+)-morphinan may be a compound comprising Formula (IIa) or a pharmaceutically acceptable salt thereof:

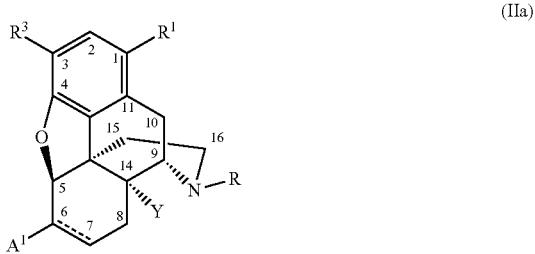

(IIa)

wherein;

R is chosen from hydrogen, methyl, alkyl, alkenyl, allyl, methylcycloalkyl, methylcyclopropyl, methylcyclobutyl, methylaryl, methylphenyl, acyl, acylalkyl, acylcycloalkyl, acylcyclopropyl, acylcyclobutyl, acylaryl, acylphenyl, acyloxy, acyloxyalkyl, acyloxyaryl, acyloxyphenyl, alkoxy, and alkoxyalkyl;

$R^1$ is chosen from hydrogen, halo, hydroxy, alkoxy, alkoxyalkyl, alkoxyalkenyl, aryloxy, alkyl, alkenyl, aryl, heteroaryl, and amine;

$R^3$ is chosen from hydroxy, alkoxy, aryloxy, acyl, acyloxy, and protected hydroxy;

$A_1$ is chosen from hydrogen, hydroxy, keto, alkoxy, acyl, acyloxy, amino, amide, alkylamine, hydroxyalkylamine, carboxylalkylamine, alkylcarboxylalkylamine, arylamine, alkyl, alkenyl, aryl, substituted alkyl, substituted alkenyl, and substituted aryl;

Y is chosen from hydrogen, hydroxy, alkoxy, and protected hydroxy; and the dashed line represents an optional double bond.

In one exemplary embodiment, the (+)-morphinan may be a compound comprising Formula (IIb) or a pharmaceutically acceptable salt thereof:

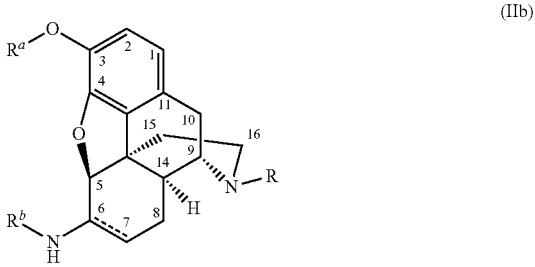

(IIb)

wherein:

R is chosen from hydrogen, alkyl, methyl, allyl, methylcyclopropyl, and methylcyclobutyl;

$R^a$ is chosen from hydrogen, methyl, alkyl, phenyl, and benzyl;

$R^b$ is chosen from hydrogen, methyl, alkyl, alkylalcohol, alkylcarboxyl, alkylcarboxylalkylester, acyl, acylalkyl, acylaryl, acyloxy, acyloxyalkyl, acyloxyaryl; and Y is chosen from hydrogen and hydroxy.

In one iteration of this embodiment, R is methylcyclopropyl, $R^a$ is hydrogen, $R^b$ is methyl, and Y is hydroxy. In another iteration, R is methyl, $R^a$ is methyl, $R^b$ is methylacetylmethylester; and Y is hydrogen. In yet another iteration, R is allyl, $R^a$ is methyl, $R^b$ is propyl; and Y is hydrogen. In a further iteration, R is allyl, $R^a$ is methyl, $R^b$ is ethylalcohol; and Y is hydrogen.

In another exemplary embodiment, the (+)-morphinan may be a compound comprising Formula (IIc) or a pharmaceutically acceptable salt thereof:

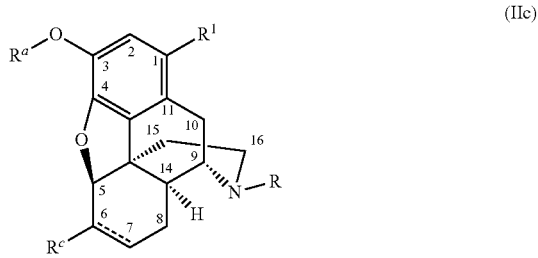

(IIc)

wherein:

R is chosen from hydrogen, methyl, alkyl, allyl, methylcyclopropyl, and methylcyclobutyl;

$R^1$ is chosen from hydrogen, halo, hydroxy, alkoxy, amine, aryl, heteroaryl, and furanyl;

$R^a$ is chosen from hydrogen, methyl, alkyl, phenyl, and benzyl;

$R^c$ is chosen from hydroxy, methoxy, alkoxy, keto, and acyl;

Y is chosen from hydrogen and hydroxy; and the dashed line represents an optional double bond.

In one iteration of this embodiment, R is methylcyclopropyl, $R^1$ is hydrogen, $R^a$ is methyl, $R^c$ is hydroxy; and Y is hydrogen. In another iteration, R is methylcyclopropyl, $R^1$ is hydrogen, $R^a$ is methoxy, $R^c$ is methyl, Y is hydrogen, and the optional double bond is present. In a further iteration, R is allyl, $R^1$ is furanyl, $R^a$ is methyl, $R^c$ is keto, and Y is hydrogen. In still another iteration, R is hydrogen, $R^1$ is hydrogen, $R^a$ is methyl, $R^c$ is methoxy, Y is hydrogen, and the optional double bond is present.

(iii) Compounds Comprising Formula (III)

In another embodiment, the (+)-morphinan may be a compound comprising Formula (III) or a pharmaceutically acceptable salt thereof, as detailed above in section (I)(c).

In an exemplary embodiment, the (+)-morphinan may be a compound comprising Formula (IIIa) or a pharmaceutically acceptable salt thereof:

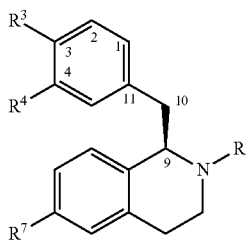

(IIIa)

wherein:
R is chosen from hydrogen, methyl, alkyl, alkenyl, allyl, methylcycloalkyl, methylcyclopropyl, methylcyclobutyl, methylaryl, methylphenyl, acyl, acylalkyl, acylcycloalkyl, acylcyclopropyl, acylcyclobutyl, acylaryl, acylphenyl, acyloxy, acyloxyalkyl, acyloxyaryl, acyloxyphenyl, alkoxy, and alkoxyalkyl; and $R^3$, $R^4$, and $R^7$ are independently chosen from hydrogen, hydroxy, alkoxy, aryloxy, acyloxy, amine, halo, and protected hydroxy In one iteration of this embodiment, R is allyl, $R^3$ is methoxy, $R^4$ is hydroxy, and $R^7$ is methoxy.

(c) Optional Excipients

The pharmaceutical composition may further comprise at least one pharmaceutically acceptable excipient. Non-limiting examples of suitable excipients include diluents, binders, fillers, buffering agents, pH modifying agents, effervescent disintegrants, non-effervescent disintegrants, dispersing agents, stabilizers, preservatives, compaction agents, lubricants, coloring agents and/or flavoring agents. The amount and types of excipients utilized to form the pharmaceutical composition may be selected according to known principles of pharmaceutical science.

In one embodiment, the excipient may include at least one diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lacitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may comprise a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may include a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Representative examples of suitable buffering agents include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be citric acid, sodium carbonate, or sodium bicarbonate.

In a further embodiment, the excipient may include a non-effervescent disintegrant. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In another embodiment, the excipient may comprise an effervescent disintegrant. By way of non-limiting example, suitable effervescent disintegrants include sodium bicarbonate in combination with citric acid and sodium bicarbonate in combination with tartaric acid.

In another alternate embodiment, the excipient may also include a preservative. Non-limiting examples of suitable preservatives include antioxidants, such as alpha-tocopherol or ascorbate, and antimicrobials, such as parabens, chlorobutanol or phenol.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In a further embodiment, the excipient may include a lubricant. Non-limiting examples of suitable lubricants include minerals such as talc or silica; and fats such as vegetable stearin, magnesium stearate or stearic acid.

In still another embodiment, it may be desirable to provide a coloring agent. Suitable color additives include, but are not limited to, food, drug and cosmetic colors (FD&C), drug and cosmetic colors (D&C), or external drug and cosmetic colors (Ext. D&C).

In a further embodiment, the excipient may include flavoring agents. Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot). In still another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; stevia-derived sweeteners; chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof. In still another embodiment, the excipient may include a taste-masking agent. Taste-masking materials include cellulose hydroxypropyl ethers (HPC); low-substituted hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and combinations thereof.

The weight fraction of the excipient or combination of excipients in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(III) Methods for Treating Conditions Using (+)-Morphinans Comprising TLR9 Antagonist Activity Either Alone or in Combination with Another Therapeutic Agent Another aspect of the present invention encompasses methods for treating a condition in a subject in need thereof. In general, the method comprises administering to the subject at least one (+)-morphinan comprising TLR9 antagonist activity either alone or in combination with at least one additional therapeutic agent. A variety of disorders or disease states may be treated with the compounds of the invention. Suitable disorders and diseases that may be treated include pain conditions, inflammatory disorders, acetaminophen toxicity, autoimmune disorders, neurodegenerative disorders, and cancer.

The subject to be treated may be any subject diagnosed as having one of the indicated conditions. Moreover, the subject to be treated may be in need of treatment for the one of the conditions. That is, the subject has been diagnosed with the condition or is at risk for developing the condition, and consequently, is in need of treatment for the condition. The subject may be diagnosed with the condition using diagnostic or clinical tests that are well known. Furthermore, those of skill in the art appreciate that different diagnostic or clinical tests are used to diagnosis the different conditions or disorders. The diagnostic tools include, without limit, physical examination, patient history, screening tests, laboratory tests, molecular tests, genomic tests, imaging tools, physical tests, mental tests, and the like. Since the perception of pain may be quite subjective, tools such as the McGill Pain Questionnaire may be used to assess the quality of pain (e.g., sharp, stabbing, squeezing, etc.), and the intensity of pain may be quantified using a numerical scale that ranges from 0 to 10. Skilled diagnosticians are familiar with other indicators of pain.

In general, the subject will be a human. Without departing from the scope of the invention, however, other mammalian subjects may be used. Suitable mammalian subjects include; companion animals, such as cats and dogs; livestock animals, such as cows, pigs, horses, sheep, and goats; zoo animals; and research animals, such as non-human primates and rodents.

(a) conditions
  (i) Pain Conditions

In one embodiment, the (+)-morphinan having TLR9 antagonist activity or a pharmaceutically acceptable salt thereof may be used alone or in combination with at least one additional therapeutic agent for the treatment of a pain condition in a subject. In general, the subject to be treated has been diagnosed as having a pain condition. As used herein, the term "pain" refers to the unpleasant sensory and emotional experience associated with actual or perceived tissue damage by a noxious stimulus. The pain may be acute or chronic pain. For example, the pain may be traumatic or inflammatory pain, which results from injury to non-neural tissue. Non-limiting examples of traumatic or inflammatory pain include arachnoiditis, arthritis, back pain, burn pain, central pain syndrome, cancer pain, headaches (including migraines, cluster, and tension headaches); head and facial pain, muscle pain (including fibromyalgia), myofascial pain syndromes; reflex sympathetic dystrophy syndrome, repetitive stress injuries, sciatica, shingles and other skin disorders, sports injuries, spinal stenosis, surgical pain, temporomandibular disorders, trauma, and/or vascular disease or injury.

Alternatively, the pain may be neuropathic pain, which results from injury to or inflammation of the central or peripheral nervous system. Neuropathic pain may occur in any part of the body and is frequently described as a hot, burning sensation, which can be devastating to the affected individual. Neuropathic pain may be acute or chronic; it may result from diseases that affect nerves (such as diabetes), from trauma, surgical procedures, arthritis, AIDS, burn injuries, cerebral or lumbar spine disease, fibromyalgia, post-eschemic pain, tumors, viral neuralgias, or, because chemotherapy drugs can affect nerves, it may be a consequence of cancer treatment. Among the many neuropathic pain conditions are diabetic neuropathy (which results from nerve damage secondary to vascular problems that occur with diabetes); reflex sympathetic dystrophy syndrome, which may follow injury; phantom limb and post-amputation pain, which may result from the surgical removal of a limb; post-herpetic neuralgia, which may occur after an outbreak of shingles; and complex regional pain syndrome or central pain syndrome, which may result from trauma to the brain or spinal cord.

Characteristic symptoms of neuropathic pain include hyperesthesia (i.e., enhanced sensitivity to a natural stimulus); allodynia (i.e., widespread tenderness or hypersensitivity to tactile stimuli); hyperalgesia (i.e., abnormal sensitivity to pain); spontaneous burning pain; and/or phantom pain (i.e., perception of pain that is non-existent). Hyperesthesia involves an unusual increased or altered sensitivity to sensory stimuli, including for example, acoustic, cerebral, gustatory, muscular, olfactory, onelric, optic, or tactile. As an example, a painful sensation from a normally painless touch stimulus. Allodynia involves an intensified, unpleasant, and painful perception of stimuli triggered by heat or by contact, which is based on a lowering of the pain threshold for these stimuli, including, for example, a non-noxious stimulus to normal skin. Hyperalgesia involves the excessive perception of a variety of stimuli, again based on a lowering of the pain threshold and thus an abnormally increased pain sense, including for example, auditory or muscular stimuli. Phantom pain involves a perception of pain in a limb that is non-existent, such as perceived pain in a limb that has been amputated, i.e. phantom limb syndrome.

(ii) Inflammatory Disorders

In another embodiment, the (+)-morphinan having TLR9 antagonist activity or a pharmaceutically acceptable salt thereof may be used alone or in combination with at least one additional therapeutic agent for the treatment of inflammation in a subject. For example, the inflammatory disorder may be arthritis including, but not limited to, rheumatoid arthritis, spondyloarthropathies, gouty arthritis, osteoarthritis, systemic lupus erythematosus, or juvenile arthritis. In some embodiments, the inflammation may be associated with asthma, allergic rhinitis, sinus diseases, bronchitis, tuberculosis, acute pancreatitis, sepsis, infectious diseases, menstrual cramps, premature labor, tendinitis, bursitis, skin-related conditions such as psoriasis, eczema, atopic dermatitis, urticaria, dermatitis, contact dermatitis, and burns, or from post-operative inflammation including from ophthalmic surgery such as cataract surgery and refractive surgery. In a further embodiment, the inflammatory disorder may be a gastrointestinal condition such as inflammatory bowel disease, Crohn's disease, gastritis, irritable bowel syndrome, chronic cholecystitis, or ulcerative colitis. In yet another embodiment, the inflammation may be associated with diseases such as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, allergic rhinitis, respiratory distress syndrome, systemic inflammatory response syndrome (SIRS), cancer-associated inflammation, reduction of tumor-associated angiogenesis, endotoxin shock syndrome, atherosclerosis, and the like. In an alternate embodiment, the inflammatory disorder may be associated with an ophthalmic disease, such as retinitis, retinopathies, uveitis, ocular photophobia, or of acute injury to the eye tissue. In still another embodiment, the inflammation may be a pulmonary inflammation, such as that associated with viral infections or cystic fibrosis, chronic obstructive pulmonary disease, or acute respiratory distress syndrome. The inflammatory disorder may also be associated with tissue rejection, graft v. host diseases, delayed-type hypersensitivity, as well as immune-mediated and inflammatory elements of CNS diseases such as Alzheimer's, Parkinson's, multiple sclerosis, and the like.

(iii) Acetaminophen Toxicity

In still another embodiment, the (+)-morphinan having TLR9 antagonist activity or a pharmaceutically acceptable salt thereof may also be alone or in combination with at least one other therapeutic agent to treat acetaminophen toxicity (also known as paracetamol toxicity). High levels of acetaminophen may lead to damage of the liver (i.e., acetaminophen-induced hepatotoxicity) or the kidney (i.e., acetaminophen-induced nephrotoxicity). Acetaminophen toxicity may result from an acute overdose of acetaminophen or a chronic overdose acetaminophen. The amount of ingested acetaminophen at which toxicity occurs may be reduced upon chronic ethanol use, malnourishment, or diminished nutritional status, fasting, or viral illness with dehydration, or use of certain pharmaceutical agents that interact with the enzyme systems that metabolize acetaminophen.

Acetaminophen-induced hepatotoxicity may be manifested by cellular oxidative damage, mitochondrial dysfunction, and a subsequent inflammatory response. Cellular damage may be monitored by elevated levels of serum alanine transaminase (ALT) or serum aspartate transaminase (AST), and the inflammatory response may be monitored by increased levels of pro-interleukin(IL)-1beta transcript levels. Acetaminophen-induced hepatotoxicity also may lead to hepatocellular injury, death, and centrilobular (zone III) liver necrosis. Similar enzymatic reactions occur in the kidney, and may contribute to some degree of extra-hepatic organ dysfunction.

(iv) Autoimmune Disorders

In yet another embodiment, the (+)-morphinan having TLR9 antagonist activity or a pharmaceutically acceptable salt thereof may also be alone or in combination with at least one other therapeutic agent to treat an autoimmune disease or disorder. The autoimmune disorder may be systemic, such as Lupus, wherein many tissues or organs are affected or damaged. Alternatively, the autoimmune disorder may be localized, such as type I diabetes mellitus, wherein a single organ or tissue is damaged or affected. Non-limiting examples of autoimmune disorders include acute disseminated encephalomyelitis (ADEM), Addison's disease, alopecia areata, antiphospholipid antibody syndrome (APS), autoimmune hemolytic anemia, autoimmune hepatitis, autoimmune inner ear disease, bullous pemphigoid, celiac disease, Chagas disease, chronic obstructive pulmonary disease, Crohn's disease, dermatomyositis, diabetes mellitus type 1, endometriosis, Goodpasture's syndrome, Graves' disease, Guillain-Barre syndrome (GBS), Hashimoto's thyroiditis, hidradenitis suppurativa, Kawasaki disease, IgA nephropathy, idiopathic thrombocytopenic purpura, interstitial cystitis, lupus erythematosus (Lupus), mixed connective tissue disease, morphea, multiple sclerosis, myasthenia gravis, narcolepsy, neuromyotonia, pemphigus vulgaris, pernicious anemia, psoriasis, psoriatic arthritis, polymyalgia rheumatica, polymyositis, primary biliary cirrhosis, rheumatoid arthritis and juvenile rheumatoid arthritis, schizophrenia, schleroderma, sclerosing cholangitis, Sjogren's syndrome, stiff person syndrome, temporal arteritis/giant cell arteritis, ulcerative colitis, vasculitis, vitiligo, and Wegener's granulomatosis.

(v) Neurodegenerative Disorders

In an alternate embodiment, the (+)-morphinan having TLR9 antagonist activity or a pharmaceutically acceptable salt thereof may be used alone or in combination with at least one other therapeutic agent to treat a neurodegenerative disorder. Non-limiting examples of neurodegenerative disorders include adrenal leukodystrophy, aging-related disorders and dementias, alcoholism, Alexander's disease, Alper's disease, Alzheimer's disease, amyotrophic lateral sclerosis (Lou Gehrig's Disease), ataxia telangiectasia, Batten disease (also known as Spielmeyer-Vogt-Sjögren-Batten disease), bovine spongiform encephalopathy (BSE), canavan disease, cerebral palsy, Cockayne syndrome, corticobasal degeneration (CBD), Creutzfeldt-Jakob disease, familial fatal insomnia, frontotemporal lobar degeneration, frontal temporal dementias (FTDs), Huntington's disease, HIV-associated dementia, Kennedy's disease, Krabbe's disease, Lewy body disease, neuroborreliosis, Machado-Joseph disease (spinocerebellar ataxia type 3), multiple system atrophy, multiple sclerosis, narcolepsy, Niemann Pick disease, Parkinson disease, Pelizaeus-Merzbacher disease, Pick's disease, primary lateral sclerosis, progressive supranuclear palsy (PSP), psychotic disorders, Refsum's disease, Sandhoff disease, Schilder's disease, schizoaffective disorder, schizophrenia, stroke, subacute combined degeneration of spinal cord secondary to pernicious anemia, spinocerebellar ataxia, spinal muscular atrophy, Steele-Richardson-Olszewski disease, Tabes dorsalis, and toxic encephalopathy.

(vi) Cancers

In still another embodiment, the (+)-morphinan having TLR9 antagonist activity or a pharmaceutically acceptable salt thereof may be used in combination with a chemotherapeutic agent to treat a neoplasm or a cancer. The neoplasm may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood).

(b) Treatment Formulations (i) Formulations Comprising at Least One (+)-Morphinan having TLR9 Antagonist Activity In some embodiments, the method comprises administering to the subject at least one (+)-morphinan compound having TLR9 antagonist activity or a pharmaceutically acceptable salt thereof.

In one embodiment, the (+)-morphinan administered to the subject may be a compound comprising Formula (IIa) or a pharmaceutically acceptable salt thereof:

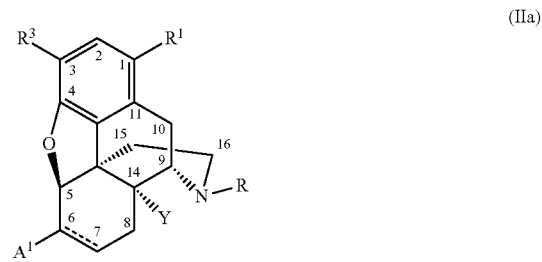

(IIa)

wherein:
R is chosen from hydrogen, methyl, alkyl, alkenyl, allyl, methylcycloalkyl, methylcyclopropyl, methylcyclobutyl, methylaryl, methylphenyl, acyl, acylalkyl, acylcycloalkyl, acylcyclopropyl, acylcyclobutyl, acylaryl, acylphenyl, acyloxy, acyloxyalkyl, acyloxyaryl, acyloxyphenyl, alkoxy, and alkoxyalkyl;

$R^1$ is chosen from hydrogen, halo, hydroxy, alkoxy, alkoxyalkyl, alkoxyalkenyl, aryloxy, alkyl, alkenyl, aryl, heteroaryl, and amine;

$R^3$ is chosen from hydroxy, alkoxy, aryloxy, acyl, acyloxy, and protected hydroxy;

$A_1$ is chosen from hydrogen, hydroxy, keto, alkoxy, acyl, acyloxy, amino, amide, alkylamine, hydroxyalkylamine, carboxylalkylamine, alkylcarboxylalkylamine, arylamine, alkyl, alkenyl, aryl, substituted alkyl, substituted alkenyl, and substituted aryl; provided, however, that when $A_1$ is keto, $R^1$ is other than hydrogen;

Y is chosen from hydrogen, hydroxy, alkoxy, and protected hydroxy; and the dashed line represents an optional double bond In one preferred embodiment, the (+)-morphinan administered to the subject may be a compound comprising Formula (IIb) or a pharmaceutically acceptable salt thereof:

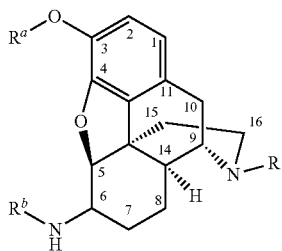

(IIb)

wherein:
R is chosen from hydrogen, alkyl, methyl, allyl, methylcyclopropyl, and methylcyclobutyl;
$R^a$ is chosen from hydrogen, methyl, alkyl, phenyl, and benzyl;
$R^b$ is chosen from hydrogen, methyl, alkyl, alkylalcohol, alkylcarboxyl, alkylcarboxylalkylester, acyl, acylalkyl, acylaryl, acyloxy, acyloxyalkyl, acyloxyaryl; and
Y is chosen from hydrogen and hydroxy.

In an exemplary iteration of this embodiment, R is methylcyclopropyl, $R^a$ is hydrogen, $R^b$ is methyl, and Y is hydroxy. In another iteration, R is methyl, $R^a$ is methyl, $R^b$ is methylacetylmethylester; and Y is hydrogen. In yet another iteration, R is allyl, $R^a$ is methyl, $R^b$ is propyl; and Y is hydrogen. In a further iteration, R is allyl, $R^a$ is methyl, $R^b$ is ethylalcohol; and Y is hydrogen.

In another preferred embodiment, the (+)-morphinan administered to the subject may be a compound comprising Formula (IIc) or a pharmaceutically acceptable salt thereof:

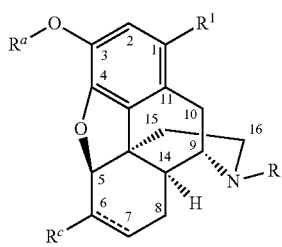

(IIc)

wherein:
R is chosen from hydrogen, methyl, alkyl, allyl, methylcyclopropyl, and methylcyclobutyl;
$R^1$ is chosen from hydrogen, halo, hydroxy, alkoxy, amine, aryl, heteroaryl, and furanyl;
$R^a$ is chosen from hydrogen, methyl, alkyl, phenyl, and benzyl;
$R^c$ is chosen from hydroxy, methoxy, alkoxy, keto, and acyl; provided, however, that when $R^c$ is keto, $R^1$ is not hydrogen;
Y is chosen from hydrogen and hydroxy; and
the dashed line represents an optional double bond.

In one iteration of this embodiment, R is methylcyclopropyl, $R^1$ is hydrogen, $R^a$ is methyl, $R^c$ is hydroxy; and Y is hydrogen. In another iteration, R is methylcyclopropyl, $R^1$ is hydrogen, $R^a$ is methyl, $R^c$ is methoxy, Y is hydrogen, and the optional double bond is present. In a further iteration, R is allyl, $R^1$ is furanyl, $R^a$ is methyl, $R^c$ is keto, and Y is hydrogen. In still another iteration, R is hydrogen, $R^1$ is hydrogen, $R^a$ is methyl, $R^c$ is methoxy, Y is hydrogen, and the optional double bond is present.

In another embodiment, the (+)-morphinan administered to the subject may be a compound comprising Formula (IIIa) or a pharmaceutically acceptable salt thereof:

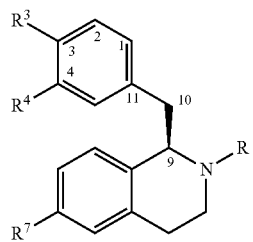

(IIIa)

wherein:
R is chosen from hydrogen, methyl, alkyl, alkenyl, allyl, methylcycloalkyl, methylcyclopropyl, methylcyclobutyl, methylaryl, methylphenyl, acyl, acylalkyl, acylcycloalkyl, acylcyclopropyl, acylcyclobutyl, acylaryl, acylphenyl, acyloxy, acyloxyalkyl, acyloxyaryl, acyloxyphenyl, alkoxy, and alkoxyalkyl; and
$R^3$, $R^4$, and $R^7$ are independently chosen from hydrogen, hydroxy, alkoxy, aryloxy, acyloxy, amine, halo, and protected hydroxy.

In one iteration of this embodiment, R is allyl, $R^3$ is methoxy, $R^4$ is hydroxy, and $R^7$ is methoxy.

(ii) Combination Formulations

In other embodiments, the treatment method comprises administering to the subject a combination formulation comprising at least one (+)-morphinan TLR9 antagonist, as disclosed herein, and at least one other therapeutic agent. It is envisioned that when the combination formulation comprises more than one additional therapeutic agent, the different agents may be drawn from one of the classes listed below, or the different agents may be drawn from different classes listed below.

In one embodiment, the combination formulation may comprise a (+)-morphinan or a pharmaceutically acceptable salt thereof and a compound comprising Formula (IV) or a pharmaceutically acceptable salt thereof, as detailed above in section (II).

In another embodiment, the combination formulation may comprise a (+)-morphinan or a pharmaceutically acceptable salt thereof, as detailed above in sections (I)(a), (I)(b), and (I)(c), and an analgesic agent. The analgesic may be an (−)-opioid analgesic. Alternatively, the analgesic may be a non-opioid analgesic. Non-limiting examples of suitable opioid analgesics include buprenorphine, butorphanol, codeine, dihydrocodeine, dihydromorphine, etorphine, fentanyl, hydrocodone, hydromorphone, levophanol, meperidine, methadone, morphine, nalbuphine, norcodeine, normorphine, oxycodone, oxymorphone, pentazocine, and propoxyphene. In some combinations comprising an opioid analgesic, the concentration or dose of the opioid analgesic in the combination formulation may be sub-analgesic. Examples of suitable non-opioid analgesics include without limit acetylsalicylic acid, acetaminophen (paracetamol), ibuprofen, ketoprofen, indomethacin, diflunisol, naproxen, ketorolac, dichlophenac, tolmetin, sulindac, phenacetin, piroxicam, and mefamanic acid. In further embodiments, the analgesic may comprise a combination of an opiate analgesic and a non-opioid analgesic. For example, acetaminophen may be combined with codeine, hydrocodone, oxycodone, propoxyphene, or another opioid analgesic. In an exemplary embodiment, the combination may comprise a (+)-morphinan comprising Formulas (I), (II), (IIa), (IIb), (IIc), (III), or (IIIa), and acetaminophen. The concentration of acetaminophen in such a combination may be lower than in currently available acetaminophen combination formulations.

In a further embodiment, the combination formulation may comprise a (+)-morphinan or a pharmaceutically acceptable salt thereof, as detailed above in sections (I)(a), (I)(b), and (I)(c), and an anti-inflammatory agent. The anti-inflammatory agent may be a glucocorticoid steroid such as the naturally occurring hydrocortisone (cortisol), or synthetic glucocorticoids such as prednisone, prednisolone, methylprednisolone, dexamethasone, betamethasone, triamcinolone, beclometasone, fludrocortisones, deoxycorticosterone, alclometasone, fluocinonide, aldosterone, and derivatives thereof. Alternatively, the anti-inflammatory agent may be a non-steroidal anti-inflammatory agent (NSAID). Non-limiting examples of suitable NSAIDs include acetylsalicylic acid (aspirin), celecoxib, choline magnesium salicylate, Cox-2 inhibitors, diclofenac, diflunisal, etodolac, fenoprofen, flufenisal, flurbiprofen, ibuprofen, indomethacin, ketoprofen, ketorolac, meclofenamate, mefenamate, nabumetone, naproxen, oxaprozin, phenylbutazone, piroxicam, salsalate, sulindac, tolmetin, valdecoxib, and zomepirac.

In yet another embodiment, the combination formulation may comprise a (+)-morphinan or a pharmaceutically acceptable salt thereof, as detailed above in sections (I)(a), (I)(b), and (I)(c), and an antibiotic agent. Non-limiting examples of suitable antibiotic agents include aminoglycosides such as, e.g., amikacin, gentamicin, kanamycin, neomycin, netilmicin, streptomycin, and tobramycin; a carbecephem such as loracarbef; carbapenems such as, e.g., certapenem, imipenem, and meropenem; cephalosporins such as, e.g., cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone; macrolides such as, e.g., azithromycin, clarithromycin, dirithromycin, erythromycin, and troleandomycin; monobactam; penicillins such as, e.g., amoxicillin, ampicillin, carbenicillin, cloxacillin, dicloxacillin, nafcillin, oxacillin, penicillin G, penicillin V, piperacillin, and ticarcillin; polypeptides such as, e.g., bacitracin, colistin, and polymyxin B; quinolones such as, e.g., ciprofloxacin, enoxacin, gatifloxacin, levofloxacin, lomefloxacin, moxifloxacin, norfloxacin, ofloxacin, and trovafloxacin; sulfonamides such as, e.g., mafenide, sulfacetamide, sulfamethizole, sulfasalazine, sulfisoxazole, and trimethoprim-sulfamethoxazole; tetracyclines such as, e.g., demeclocycline, doxycycline, minocycline, and oxytetracycline); and an antimicrobial agent such as, e.g., ketoconazole, amoxicillin, cephalexin, miconazole, econazole, acyclovir, and nelfinavir.

In another alternate embodiment, the combination formulation may comprise a (+)-morphinan or a pharmaceutically acceptable salt thereof, as detailed above in sections (I)(a), (I)(b), and (I)(c), and an agent used to treat acetaminophen toxicity. Suitable agents include acetylcysteine (also called N-acetylcysteine), glutathione, and activated charcoal.

In still another embodiment, the combination formulation may comprise a (+)-morphinan or a pharmaceutically acceptable salt thereof, as detailed above in sections (I)(a), (I)(b), and (I)(c), and an autoimmune therapeutic agent. Non-limiting examples of suitable autoimmune therapeutic agents include immunosuppressants such as azathioprine, chlorambucil, cyclophosphamide, cyclosporine, mycophenolate, or methotrexate; corticosteroids such as prednisone; the psoriasis treatment agent alefacept; TNF blockers such as etanercept, infliximab, or adalimumab; white blood cell blockers such as abatacept or rituximab; the leprosy drug clofazimine; and chemotherapeutic agents such as vorinostat.

In a further embodiment, the combination formulation may comprise a (+)-morphinan or a pharmaceutically acceptable salt thereof, as detailed above in sections (I)(a), (I)(b), and (I)(c), and a neurodegenerative disorder therapeutic agent. Typically, the neurodegenerative disorder therapeutic agent is tailored to the specific neurodegenerative disorder to be treated. Suitable therapeutic agents for the treatment of Parkinson disease include, without limit, levadopa (i.e., L-DOPA); a decarboxylase inhibitor such as carbidopa; a direct acting dopamine agonist such bromocriptine, pergolide, ropinirole or pramipexole; a dopamine uptake inhibitor such as amantadine; an anticholinergic such as trihexyphenidyl or benztropine mesylate; a monoamine oxidase B inhibitor such as L-deprenyl; a catechol-O-methyltranferase inhibitor such as tolcapone; spheramine; and combinations thereof. Non-limiting examples of suitable therapeutic agents for the treatment of Alzheimer's disease include cholinesterase inhibitors such as donepezil, rivastigmine, galantamine, and the like; NMDA receptor antagonists such as memantine; and Alzheimer's specific agents such as tramiprosate, tarenflubil, phenserine, and the like. Targeted therapeutic agents used to treat Huntington's disease include, without limit, tetrabenazine, xenazine, and so forth. Non-limiting examples of therapeutic agents targeted to treat amyotrophic lateral sclerosis (ALS) include riluzole, mecasermin rinfabate, and the like.

In an alternate embodiment, the combination formulation may comprise a (+)-morphinan or a pharmaceutically acceptable salt thereof, as detailed above in sections (I)(a), (I)(b), and (I)(c), and a chemotherapeutic agent. The chemotherapeutic agent may be a cytotoxic agent that affects rapidly dividing cells in general, or it may be a targeted therapeutic agent that affects the deregulated proteins of cancer cells. For example, the chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, or a combination thereof. Non-limiting examples of alkylating agents include altretamine, benzodopa, busulfan, carboplatin, carboquone, carmustine, chlorambucil, chlornaphazine, cholophosphamide, chlorozotocin, cisplatin, cyclosphosphamide, dacarbazine (DTIC), estramustine, fotemustine, ifosfamide, improsulfan, lomustine, mechlorethamine, mechlorethamine oxide hydrochloride, melphalan, meturedopa, nimustine, novembichin, phenesterine, piposulfan, prednimustine, ranimustine; temozolomide, thiotepa, triethylenemelamine, trietylenephosphoramide, triethylenethiophosphaoramide, trimethylolomelamine, trofosfamide, uracil mustard and uredopa. Suitable anti-metabolites include, but are not limited to aminopterin, ancitabine, azacitidine, 6-azauridine, capecitabine, carmofur, cytarabine or cytosine arabinoside (Ara-C), dideoxyuridine, denopterin, doxifluridine, enocitabine, floxuridine, fludarabine, 5-fluorouracil (5-FU), gemcetabine, leucovorin (folinic acid), 6-mercaptopurine, methotrexate, pemetrexed, pteropterin, thiamiprine, trimetrexate, and thioguanine. Non-limiting examples of suitable anti-tumor antibiotics include aclacinomysin, actinomycin, adriamycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin. Non-limiting examples of suitable anti-cytoskeletal agents include colchicines, docetaxel, macromycin, paclitaxel (taxol), vinblastine, vincristine, vindesine, and vinorelbine. Suitable topoisomerase inhibitors include, but are not limited to, amsacrine, etoposide (VP-16), irinotecan, RFS 2000, teniposide, and topotecan. Non-limiting examples of suitable anti-hormonal agents such as aminoglutethimide, aromatase inhibiting 4(5)-imidazoles, bicalutamide, finasteride, flutamide, goserelin, 4-hydroxytamoxifen, keoxifene, leuprolide, LY117018, mitotane, nilutamide, onapristone, raloxifene, tamoxifen, toremifene, and trilostane. Non-limiting examples of targeted therapeutic agents include a monoclonal antibody such as alemtuzumab, bevacizumab, capecitabine, cetuximab, gemtuzumab, heregulin, rituximab, trastuzumab; a tyrosine kinase inhibitor such as imatinib mesylate; and a growth inhibitory polypeptide such as erythropoietin, interleukins (e.g., IL-1, IL-2, IL-3, IL-6), leukemia inhibitory factor, interferons, thrombopoietin, TNF-α, CD30 ligand, 4-1BB ligand, and Apo-1 ligand.

Those of skill in the art appreciate that pharmaceutically acceptable salts, acids, or derivatives of any of the above listed agents may be included in the combination formulations.

(c) Dosage Forms

The formulations detailed above in section (III)(b) may be administered by a number of different means that will deliver a therapeutically effective dose. For example, the formulations may be administered orally, parenterally, by inhalation spray, rectally, intradermally, intrathecally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. Formulation of therapeutic agents is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980).

Preparations for oral administration generally contain inert pharmaceutically acceptable excipients in addition to the active pharmaceutical ingredient. Oral preparations may be enclosed in gelatin capsules or compressed into tablets. Common excipients used in such preparations include pharmaceutically compatible fillers/diluents such as microcrystalline cellulose, hydroxypropyl methylcellulose, starch, lactose, sucrose, glucose, mannitol, sorbitol, dibasic calcium phosphate, or calcium carbonate; binding agents such as alginic acid, carboxymethylcellulose, microcrystalline cellulose, gelatin, gum tragacanth, or polyvinylpyrrolidone; disintegrating agents such as alginic acid, cellulose, starch, or polyvinylpyrrolidone; lubricants such as calcium stearate, magnesium stearate, talc, silica, or sodium stearyl fumarate; glidants such as colloidal silicon dioxide; sweetening agents such as sucrose or saccharin; flavoring agents such as peppermint, methyl salicylate, or citrus flavoring; coloring agents; and preservatives such as antioxidants (e.g., vitamin A, vitamin C, vitamin E, or retinyl palmitate), citric acid, or sodium citrate. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

The amount of agent that is administered to the subject can and will vary depending upon the type of agent, the subject, the condition being treated, and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

(d) Exemplary Treatment Methods

In exemplary embodiments, the condition to be treated may be a pain condition. The pain condition may be acute pain, traumatic pain, chronic pain, neuropathic pain, or combinations thereof. Generally, the subject to be treated is diagnosed as having a pain condition and is need of treatment for the pain condition. In one iteration of this embodiment, the method comprises administering to the subject in need thereof a formulation comprising at least one (+)-morphinan as detailed above in section (III)(b)(i). In another iteration of this embodiment, the method comprises administering to the subject in need thereof a formulation comprising a (+)-morphinan and a compound comprising Formula (IV) as detailed above in sections (II) and (III)(b)(ii).

(IV) Methods for Inhibiting TLR9 Activation

A further aspect of the present invention provides methods for inhibiting the activation of TLR9. In general, the method comprises contacting a cell expressing TLR9 with a (+)-morphinan detailed above in sections (I)(a)-(c) or a pharmaceutically acceptable salt thereof.

The method of inhibiting the activation of TLR9 may be conducted in vivo or it may be conducted in vitro. Accordingly, the cell expressing TLR9 may be disposed in a subject as detailed above. In preferred embodiments, the cell may be a glial cell, a microglial cell, or an astrocyte. In an exemplary embodiment, the cell may be a glial cell in the central nervous system.

The present invention also provides a method for identifying a (+)-morphinan comprising any of the formulas disclosed herein that may be therapeutically effective for treating conditions associated with pain and inflammation. Suitable conditions include traumatic or neuropathic pain, an inflammatory disorder, acetaminophen toxicity, an autoimmune disorder, a neurodegenerative disorder, and cancer. The method comprises determining whether the compound inhibits TLR9 activation. To determine whether the (+)-morphinan inhibits TLR9 activation, the method comprises contacting a cell expressing TLR9 with an activation ligand and the (+)-morphinan of interest, wherein TLR9 activation is reduced in the presence of the (+)-morphinan as compared to a control condition in which the cell is contacted with only the activation ligand. Typically, the cell expressing TLR9 that is contacted with the (+)-morphinan of interest is in vitro.

Typically, the cell expressing TLR9 will be from a stable cell line. Non-limiting examples of suitable parental cells include HEK293, CHO, BHK, NSO, HDMEC, NHEK, and NHDF cells. In an exemplary embodiment, the cell line may be HEK293. The cells may be engineered to express TLR9 using standard procedures well known to those of skill in the art. TLR9 may be of mammalian origin, preferably of human origin.

The activation ligand used to activate TLR9 may be methylated DNA, unmethylated DNA, a CpG oligodeoxynucleotide, or an oligodeoxynucleotide. In an exemplary embodiment, the activation ligand may be CpG oligodeoxynucleotide (ODN) 2006.

The activation of TLR9 in the cell of the in vitro assay may be monitored by measuring the activity of a reporter, wherein the activity of the reporter is coupled to activation of an adaptor protein or kinase that mediates TLR9 signaling by producing intracellular signaling molecules or inducers such as NF-κB or IRF3. Non-limiting examples of suitable reporters include luciferase, alkaline phosphatase, and GFP or other fluorescent proteins. The activation of the reporter may be monitored via luminescence, fluorescence, absorbance, or optical density. In an exemplary embodiment, the reporter is secreted alkaline phosphatase (SEAP) that is induced by NF-κB, and activation of SEAP is monitored spectrophotometically.

In general, the (+)-morphinan comprising TLR9 antagonist activity may reduce the activation of TLR9 by at least about 10%. In various embodiments, the (+)-morphinan may reduce the activation of TLR9 from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 70%, from about 70% to about 80%, from about 80% to about 90%, or from about 90% to about 99%.

The in vitro screening assay may also be used to determine the optimal inhibitory concentration (or $IC_{50}$) of a (+)-morphinan comprising TLR9 antagonist activity. That is, a dose-response curve may be generated in which the concentration of the (+)-morphinan comprising TLR9 antagonist activity is varied such that the optimal inhibitory concentration may be determined.

Definitions

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like. A "$C_2$-$C_6$ alkyl" refers to an alkyl group containing from two to six carbon atoms in the principal chain.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like. A methylene group is not an alkenyl group.

As used herein, the term "alkoxy" refers to an alkyl group singular bonded to oxygen, i.e., R—O. Alkyloxy groups include methoxy, ethoxy, propoxy, butoxy, and so forth. The term "$C_2$-$C_6$ alkyoxy" describes alkoxy groups having from two to six carbons in the principal chain (i.e., ethoxy, propoxy, butoxy, and the like).

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amide, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amide, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amide, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen atom (and hence, forming a protected hydroxy), wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl(TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amide, acetal, carbamyl, carbocyclo, cyano, ester, ether, halogen, heterocyclo, hydroxy, keto, ketal, phospho, nitro, and thio.

The term "treating," as used herein, refers to inhibiting or alleviating the symptoms of the disease or disorder; reversing, inhibiting, or slowing the progression of the disease or disorder; and/or preventing or delaying the onset of the disease or disorder. The term "treatment", as used herein, unless otherwise indicated, refers to the act of treating as "treating" is defined immediately above.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various embodiments of the invention.

Example 1

Toll-Like Receptor Screening

Stimulation of TLRs 2, 3, 4, 5, 7, 8, and 9 was determined by assessing activation of the transcription factor NF-κB in HEK293 cells that were engineered to express the corresponding receptors. Assessment of TLR stimulation was based on the use of an NF-κB-inducible secreted alkaline phosphatase (SEAP) reporter system in which the SEAP reporter was under the control of a promoter inducible by NF-κB. Thus, the degree of activation of TLRs can be indirectly quantified spectrophotometrically by measuring the amount of the SEAP reporter that is produced.

General procedure. The appropriate TLR-expressing cells were plated in Growth Medium in a 96-well plate (25,000-50,000 cells/well). The cells were stimulated with the appropriate positive control ligand or no ligand was added (negative control). The positive control ligands were: HKLM was used to stimulate TLR2; poly(I:C) was used to stimulate TLR3; LPS was used to stimulate TLR4; Flagellin was used to stimulate TLR5; CL097 was used to stimulate TLR7; CL075 was used to stimulate TLR8; CpG oligodeoxynucleotide (ODN) 2006 was used to stimulate TLR9. To test whether (+)-morphinans could block that activation of the TLR, the cells were pretreated with an antagonist for 30 minutes prior to addition of the positive control ligand. For this, 20 μL of the stock test compound solution (100 μM in $H_2O$) was added to give a total volume of 200 μL. The antagonists tested were (+)-naloxone, (+)-naltrexone, sinomenine, and dihydrosinomenine; the final concentration of each was 10 μM. After a 16-20 hr incubation period at 37° C. in a $CO_2$ incubator, 20 μL of the cell culture supernatant was added to 180 μL of QUANTI-Blue™ Media (Invivo-Gen, San Diego, Calif.), and the resulting solutions were incubated at 37° C. for an additional 1-3 hours according to the manufacturer's instructions. The OD's of the samples were then read at 650 nm on a Beckman Coulter AD 340C Absorbance Detector.

Figure 1G:
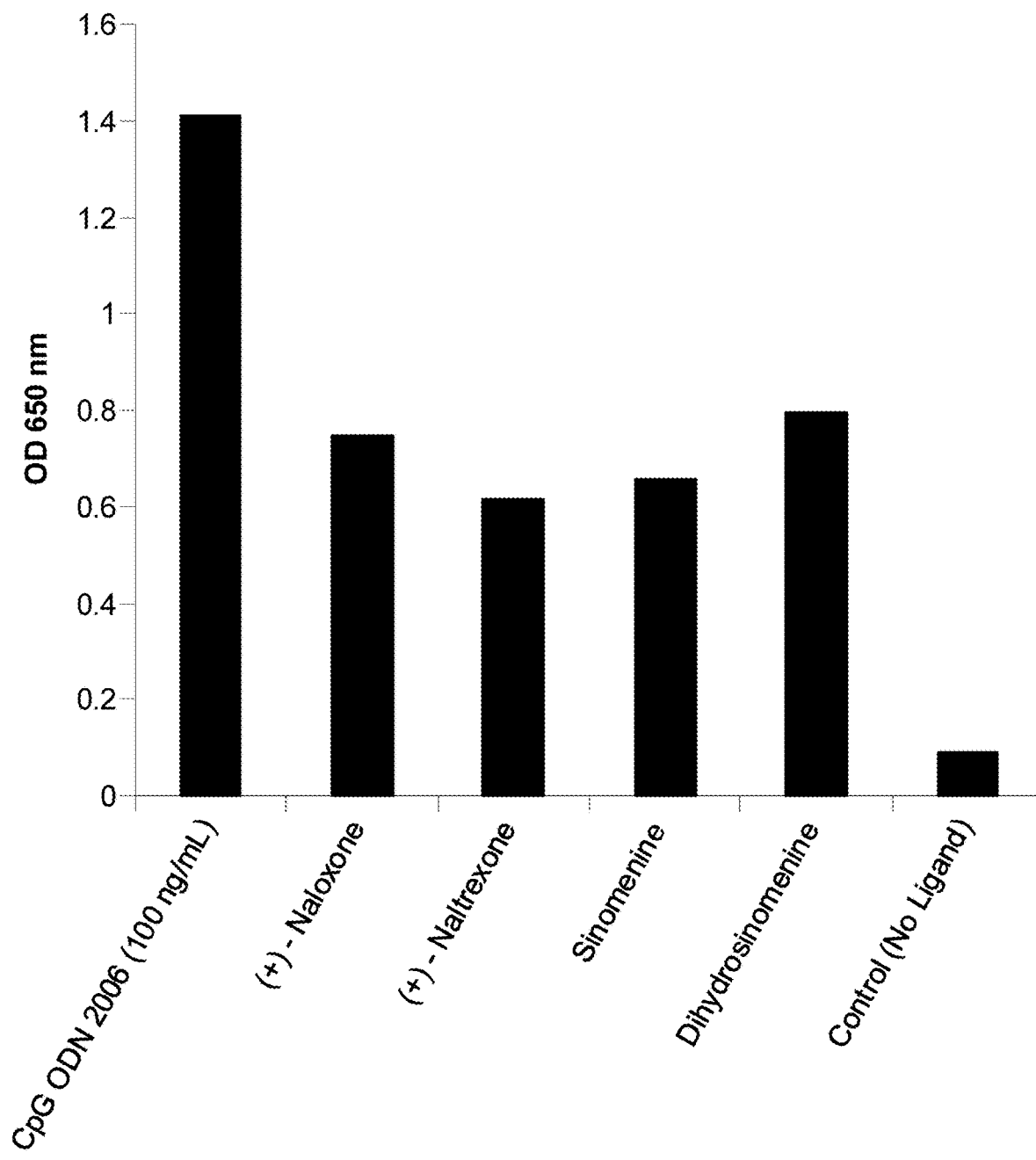

Results. The results of the antagonist screening experiments are presented in Table 1 and FIGS. 1A-1G. Each antagonist inhibited the activity of the TLRs. The greatest inhibition, however, was observed with TLR9 (see FIG. 1G). These data indicate that TLR9 is the primary target of (+)-morphinans.

TABLE 1

Antagonist Screening

Average % Inhibition at Toll-Like Receptors

| Compound | TLR2 | TLR3 | TLR4 | TLR5 | TLR7 | TLR8 | TLR9 |
| --- | --- | --- | --- | --- | --- | --- | --- |
| (+)-Naloxone | 24 | 27 | 25 | 17 | 18 | 24 | 45 |
| (+)-Naltrexone | 21 | 22 | 24 | 22 | 16 | 19 | 51 |
| Sinomenine | 30 | 28 | 24 | 19 | 20 | 20 | 55 |
| Dihydrosinomenine | 27 | 40 | 23 | 16 | 11 | 21 | 42 |

Example 2

TLR9 Screening of (+)-Morphinan Library

The secreted alkaline phosphatase reporter is under the control of a promoter inducible by the transcription factor NF-κB. A library of more than 100 (+)-morphinan compounds was screened for TLR9 antagonist activity by assessing NF-κB activation in the HEK293 cells expressing TLR9. This reporter gene allows the monitoring of signaling through the TLR, based on the activation of NF-κB.

In a 96-well plate (200 μL total volume) containing 50,000 cells/well, 20 μL of each sample compound was added to wells, in triplicate, followed by a 30 minute incubation at 37° C. and 5% $CO_2$. After the 30 minutes of incubation, 20 μL of the activator ODN2006 was added to each well. The media added to the wells was designed for the detection of NF-κB induced SEAP expression. After a 16-20 hr incubation period, the OD at 650 nm was read on a Beckman Coulter AD 340C Absorbance Detector. The results of the experiments are shown in Table 2. All compounds were tested at concentrations of 10 μM and 100 nM.

TABLE 2

TLR9 Inhibition

| Compound ID | Chemical Structure | OD 650 nm (mean ± sd) 10 μM | % Inhibition * (mean) 10 μM | OD 650 nm (mean ± sd) 100 nM | % Inhibition * (mean) 100 nM |
| --- | --- | --- | --- | --- | --- |
| II-64 | 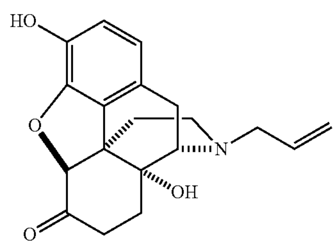 | 0.98 ± 0.01 | 31 | 1.31 ± 0.14 | 8 |
| II-73 | 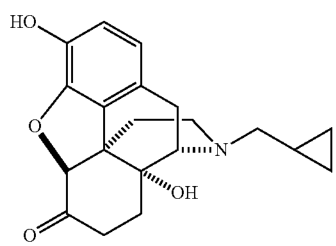 | 0.96 ± 0.08 | 32 | 1.35 ± 0.13 | 5 |
| I-30 | 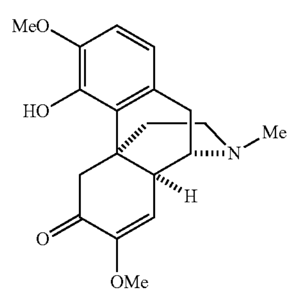 [SMILES: COC1=C[C@@H]2[C@@H]3Cc4ccc(OC)c(O)c4[C@]2(CCN3C)CC1=O] | 0.94 ± 0.05 | 33 | 1.25 ± 0.11 | 12 |

TABLE 2-continued

| | | TLR9 Inhibition | | | |
|---|---|---|---|---|---|
| Compound ID | Chemical Structure | OD 650 nm (mean ± sd) 10 μM | % Inhibition * (mean) | OD 650 nm (mean ± sd) 100 nM | % Inhibition * (mean) |
| I-9 | | 1.03 ± 0.01 | 28 | 1.50 ± 0.10 | −6 |
| I-25 | | 0.52 ± 0.07 | 63 | 1.08 ± 0.05 | 24 |
| I-18 | | 1.01 ± 0.06 | 29 | 1.40 ± 0.14 | 1 |
| II-26 | | 0.12 ± 0.00 | 92 | 1.08 ± 0.06 | 24 |
| II-24 | | 0.09 ± 0.01 | 94 | 0.65 ± 0.04 | 54 |

TABLE 2-continued

TLR9 Inhibition

| Compound ID | Chemical Structure | OD 650 nm (mean ± sd) 10 μM | % Inhibition * (mean) 10 μM | OD 650 nm (mean ± sd) 100 nM | % Inhibition * (mean) 100 nM |
|---|---|---|---|---|---|
| II-25 | 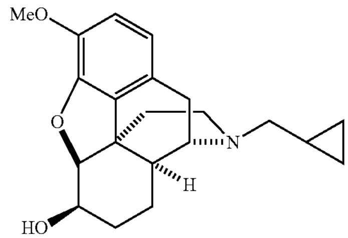 [SMILES: COc1ccc2c3c1O[C@@H]1[C@H](O)CC[C@@H]4[C@H](C2)N(CC2CC2)CC[C@]341] | 0.21 ± 0.06 | 85 | 1.33 ± 0.07 | 6 |
| II-17 | 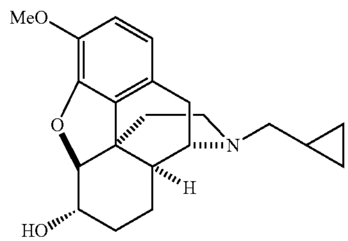 [SMILES: COc1ccc2c3c1O[C@@H]1[C@@H](O)CC[C@@H]4[C@H](C2)N(CC2CC2)CC[C@]341] | 0.39 ± 0.01 | 72 | 1.13 ± 0.10 | 21 |
| II-28 | 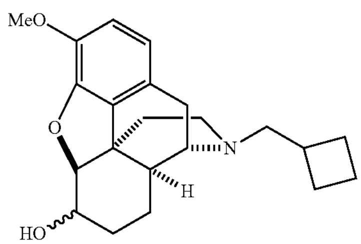 [SMILES: COc1ccc2c3c1O[C@@H]1C(O)CC[C@@H]4[C@H](C2)N(CC2CCC2)CC[C@@]314] | 0.87 ± 0.03 | 39 | 1.32 ± 0.08 | 7 |
| II-29 | 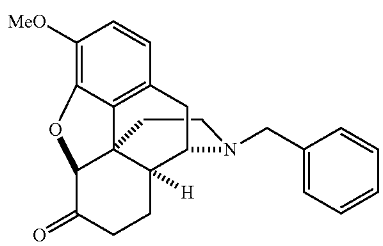 [SMILES: COc1ccc2c3c1O[C@@H]1C(=O)CC[C@@H]4[C@H](C2)N(Cc2ccccc2)CC[C@@]314] | 0.33 ± 0.03 | 77 | 1.36 ± 0.17 | 4 |
| II-31 | 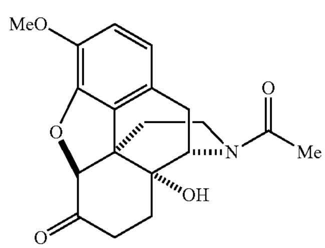 [SMILES: COc1ccc2c3c1O[C@@H]1C(=O)CC[C@]4(O)[C@H](C2)N(C(C)=O)CC[C@@]314] | 1.37 ± 0.11 | 3 | 1.40 ± 0.04 | 2 |
| II-57 | 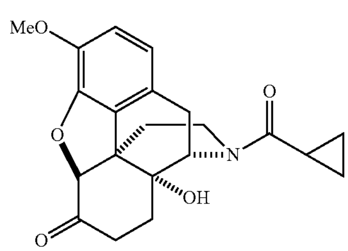 [SMILES: COc1ccc2c3c1O[C@@H]1C(=O)CC[C@]4(O)[C@H](C2)N(C(=O)C2CC2)CC[C@@]314] | 1.15 ± 0.03 | 19 | 0.84 ± 0.02 | 41 |

TABLE 2-continued

TLR9 Inhibition

| Compound ID | Chemical Structure | OD 650 nm (mean ± sd) 10 μM | % Inhibition * (mean) 10 μM | OD 650 nm (mean ± sd) 100 nM | % Inhibition * (mean) 100 nM |
|---|---|---|---|---|---|
| II-59 | 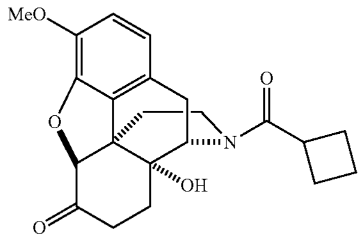 [SMILES: COc1ccc2c3c1O[C@@H]1C(=O)CC[C@]4(O)[C@H](C2)N(C(=O)C2CCC2)CC[C@@]314] | 1.41 ± 0.13 | 1 | 1.19 ± 0.07 | 17 |
| II-60 | 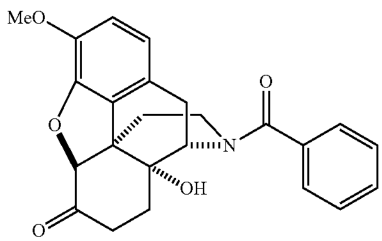 [SMILES: COc1ccc2c3c1O[C@@H]1C(=O)CC[C@]4(O)[C@H](C2)N(C(=O)c2ccccc2)CC[C@@]314] | 0.17 ± 0.03 | 88 | 1.24 ± 0.04 | 13 |
| II-83 | 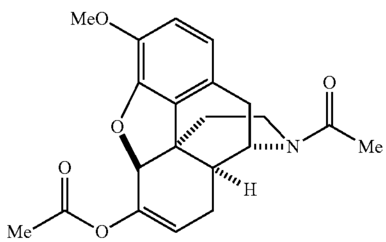 [SMILES: COc1ccc2c3c1O[C@@H]1C(OC(C)=O)=CC[C@@H]4[C@H](C2)N(C(C)=O)CC[C@@]314] | 1.11 ± 0.09 | 22 | 1.40 ± 0.13 | 1 |
| II-84 | 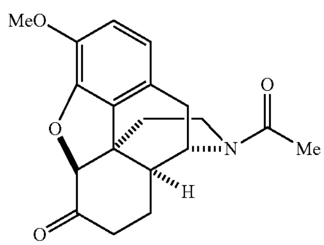 [SMILES: COc1ccc2c3c1O[C@@H]1C(=O)CC[C@@H]4[C@H](C2)N(C(C)=O)CC[C@@]314] | 1.51 ± 0.08 | −6 | 1.44 ± 0.06 | −1 |
| II-85 | 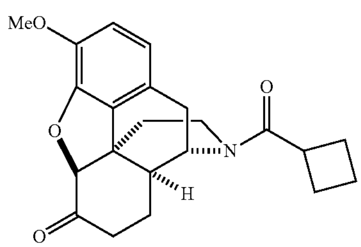 [SMILES: COc1ccc2c3c1O[C@@H]1C(=O)CC[C@@H]4[C@H](C2)N(C(=O)C2CCC2)CC[C@@]314] | 1.45 ± 0.04 | −2 | 1.45 ± 0.04 | −2 |
| II-30 | 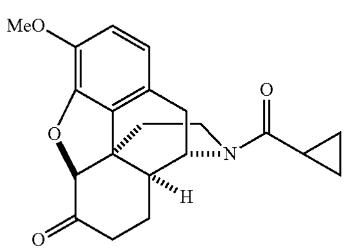 [SMILES: COc1ccc2c3c1O[C@@H]1C(=O)CC[C@@H]4[C@H](C2)N(C(=O)C2CC2)CC[C@@]314] | 1.13 ± 0.06 | 20 | 1.34 ± 0.11 | 5 |

TABLE 2-continued

TLR9 Inhibition

| Compound ID | Chemical Structure | OD 650 nm (mean ± sd) 10 μM | % Inhibition * (mean) | OD 650 nm (mean ± sd) 100 nM | % Inhibition * (mean) |
|---|---|---|---|---|---|
| II-33 | 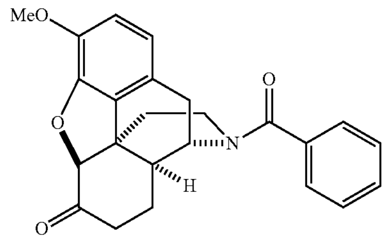 [SMILES: COc1ccc2c3c1O[C@@H]1C(=O)CC[C@@H]4[C@H](C2)N(C(=O)c2ccccc2)CC[C@@]314] | 1.37 ± 0.03 | 3 | 1.35 ± 0.15 | 5 |
| II-86 | 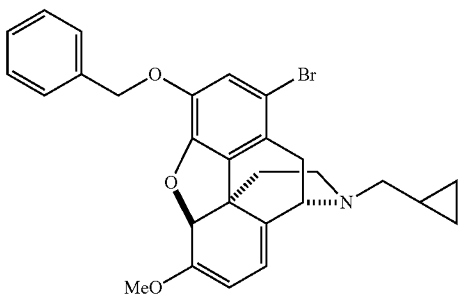 [SMILES: COC1=CC=C2[C@@H]3Cc4c(Br)cc(OCc5ccccc5)c5c4[C@]2(CCN3CC2CC2)[C@@H]1O5] | 0.13 ± 0.03 | 91 | 1.15 ± 0.11 | 19 |
| II-87 | 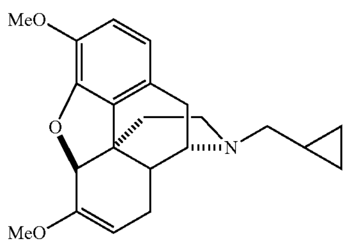 [SMILES: COC1=CCC2[C@@H]3Cc4ccc(OC)c5c4[C@]2(CCN3CC2CC2)[C@@H]1O5] | 0.45 ± 0.01 | 69 | 1.28 ± 0.06 | 10 |
| II-88 | 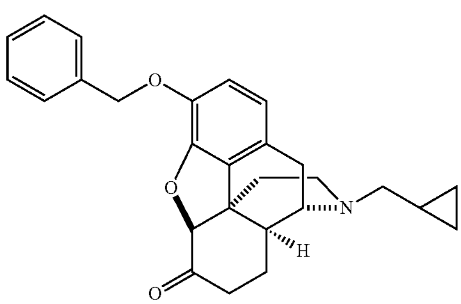 [SMILES: O=C1CC[C@@H]2[C@@H]3Cc4ccc(OCc5ccccc5)c5c4[C@]2(CCN3CC2CC2)[C@@H]1O5] | 0.13 ± 0.01 | 91 | 1.12 ± 0.15 | 21 |
| II-34 | 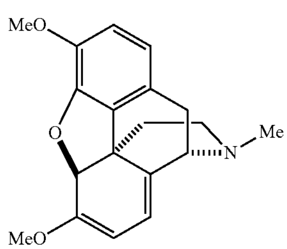 [SMILES: COC1=CC=C2[C@@H]3Cc4ccc(OC)c5c4[C@]2(CCN3C)[C@@H]1O5] | 0.94 ± 0.08 | 34 | 1.39 ± 0.05 | 2 |

TABLE 2-continued

TLR9 Inhibition

| Compound ID | Chemical Structure | OD 650 nm (mean ± sd) 10 μM | % Inhibition * (mean) | OD 650 nm (mean ± sd) 100 nM | % Inhibition * (mean) |
|---|---|---|---|---|---|
| II-22 | 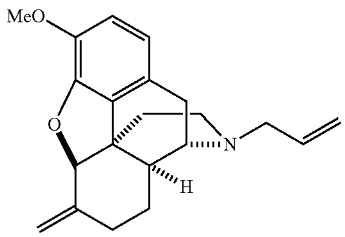 [SMILES: C=CCN1CC[C@@]23c4c5ccc(OC)c4O[C@@H]2C(=C)CC[C@@H]3[C@@H]1C5] | 0.75 ± 0.06 | 47 | 1.31 ± 0.19 | 8 |
| II-89 | 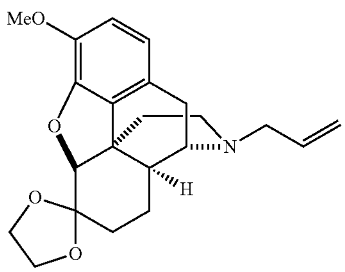 [SMILES: C=CCN1CC[C@@]23c4c5ccc(OC)c4O[C@@H]2C2(CC[C@@H]3[C@@H]1C5)OCCO2] | 1.08 ± 0.02 | 24 | 1.53 ± 0.10 | −8 |
| I-26 | 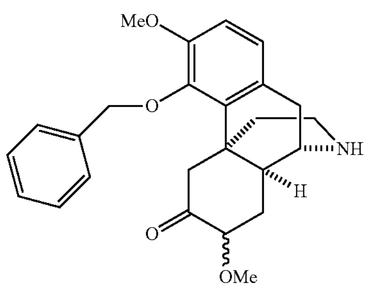 [SMILES: COc1ccc2c(c1OCc1ccccc1)[C@@]13CCN[C@@H](C2)[C@H]1CC(OC)C(=O)C3] | 0.19 ± 0.02 | 87 | 1.15 ± 0.03 | 19 |
| II-70 | 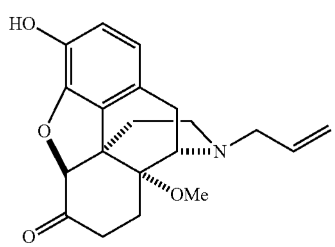 [SMILES: C=CCN1CC[C@@]23c4c5ccc(O)c4O[C@@H]2C(=O)CC[C@]3(OC)[C@@H]1C5] | 0.79 ± 0.03 | 45 | 1.12 ± 0.04 | 21 |
| II-79 | 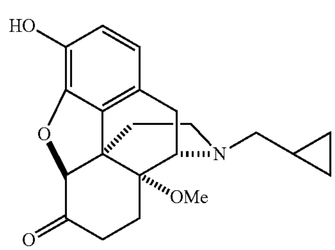 [SMILES: CO[C@]12CCC(=O)[C@H]3Oc4c(O)ccc5c4[C@]31CCN(CC1CC1)[C@H]2C5] | 1.06 ± 0.11 | 25 | 1.07 ± 0.03 | 25 |

TABLE 2-continued

TLR9 Inhibition

| Compound ID | Chemical Structure | OD 650 nm (mean ± sd) 10 μM | % Inhibition * (mean) 10 μM | OD 650 nm (mean ± sd) 100 nM | % Inhibition * (mean) 100 nM |
|---|---|---|---|---|---|
| III-2 | 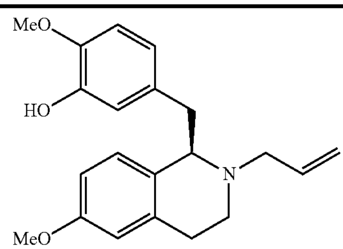 | 0.42 ± 0.04 | 71 | 1.13 ± 0.02 | 21 |
| III-3 | 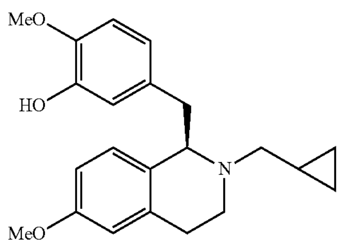 [SMILES: COc1ccc2c(c1)CCN(CC1CC1)[C@@H]2Cc1ccc(OC)c(O)c1] | 0.13 ± 0.01 | 91 | 1.03 ± 0.03 | 27 |
| III-4 | 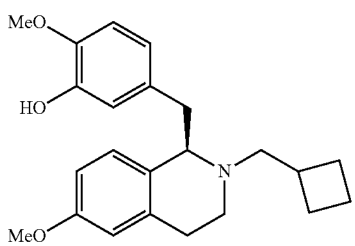 [SMILES: COc1ccc2c(c1)CCN(CC1CCC1)[C@@H]2Cc1ccc(OC)c(O)c1] | 0.11 ± 0.01 | 92 | 1.04 ± 0.04 | 27 |
| III-5 | 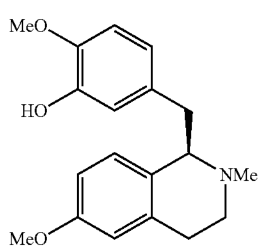 [SMILES: COc1ccc2c(c1)CCN(C)[C@@H]2Cc1ccc(OC)c(O)c1] | 0.29 ± 0.01 | 80 | 1.11 ± 0.02 | 22 |
| II-35 | 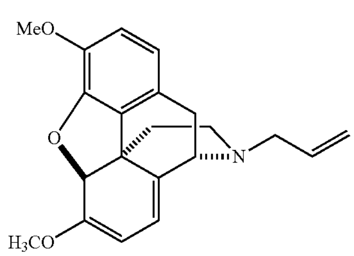 | 0.34 ± 0.03 | 76 | 1.04 ± 0.08 | 27 |
| II-36 | 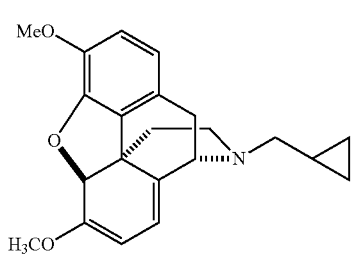 | 0.14 ± 0.01 | 90 | 1.14 ± 0.02 | 20 |

TABLE 2-continued

| | TLR9 Inhibition | | | | |
|---|---|---|---|---|---|
| Compound ID | Chemical Structure | OD 650 nm (mean ± sd) 10 μM | % Inhibition * (mean) | OD 650 nm (mean ± sd) 100 nM | % Inhibition * (mean) |
| II-37 | | 0.18 ± 0.06 | 87 | 1.13 ± 0.07 | 20 |
| II-38 | | 0.12 ± 0.01 | 92 | 0.86 ± 0.01 | 40 |
| I-22 | | 0.10 ± 0.01 | 93 | 0.93 ± 0.15 | 34 |
| II-41 | | 1.02 ± 0.09 | 28 | 1.27 ± 0.03 | 11 |
| II-42 | | 0.14 ± 0.02 | 90 | 1.00 ± 0.03 | 29 |
| II-43 | | 0.09 ± 0.00 | 94 | 0.10 ± 0.01 | 93 |

TABLE 2-continued

TLR9 Inhibition

| Compound ID | Chemical Structure | OD 650 nm (mean ± sd) 10 μM | % Inhibition * (mean) | OD 650 nm (mean ± sd) 100 nM | % Inhibition * (mean) |
|---|---|---|---|---|---|
| II-44 | [structure] | 1.03 ± 0.12 | 27 | 1.18 ± 0.02 | 17 |
| II-75 | [structure] | 0.91 ± 0.11 | 36 | 1.08 ± 0.02 | 24 |
| II-76 | [structure] | 0.10 ± 0.01 | 93 | 0.16 ± 0.01 | 89 |
| II-77 | [structure] | 0.98 ± 0.02 | 37 | 1.24 ± 0.04 | 13 |
| II-71 | [structure] | 0.10 ± 0.00 | 93 | 0.19 ± 0.01 | 87 |

TABLE 2-continued

TLR9 Inhibition

| Compound ID | Chemical Structure | OD 650 nm (mean ± sd) 10 μM | % Inhibition* (mean) | OD 650 nm (mean ± sd) 100 nM | % Inhibition* (mean) |
|---|---|---|---|---|---|
| II-72 | *structure* | 0.49 ± 0.01 | 65 | 1.10 ± 0.02 | 22 |
| II-40 | *structure* | 1.37 ± 0.07 | 4 | 1.41 ± 0.13 | 0 |
| II-46 | *structure* | 1.30 ± 0.02 | 8 | 1.24 ± 0.02 | 13 |
| II-47 | *structure* | 0.78 ± 0.07 | 45 | 1.18 ± 0.13 | 17 |
| II-48 | *structure* | 1.23 ± 0.02 | 13 | 1.43 ± 0.05 | 0 |
| II-48 | *structure* | 1.06 ± 0.02 | 25 | 1.21 ± 0.02 | 15 |

TABLE 2-continued

| | | TLR9 Inhibition | | | |
|---|---|---|---|---|---|
| Compound ID | Chemical Structure | OD 650 nm (mean ± sd) 10 μM | % Inhibition * (mean) | OD 650 nm (mean ± sd) 100 nM | % Inhibition * (mean) |
| II-51 | | 0.84 ± 0.05 | 41 | 1.20 ± 0.04 | 16 |
| II-55 | | 1.17 ± 0.08 | 18 | 1.46 ± 0.08 | −3 |
| II-74 | | 0.12 ± 0.00 | 92 | 0.61 ± 0.03 | 57 |
| II-90 | | 1.17 ± 0.05 | 88 | 1.39 ± 0.03 | 2 |
| II-78 | | 0.11 ± 0.01 | 92 | 0.14 ± 0.02 | 90 |
| II-82 | | 0.49 ± 0.03 | 65 | 1.37 ± 0.02 | 4 |

TABLE 2-continued

TLR9 Inhibition

| Compound ID | Chemical Structure | OD 650 nm (mean ± sd) 10 μM | % Inhibition * (mean) 10 μM | OD 650 nm (mean ± sd) 100 nM | % Inhibition * (mean) 100 nM |
|---|---|---|---|---|---|
| II-62 | 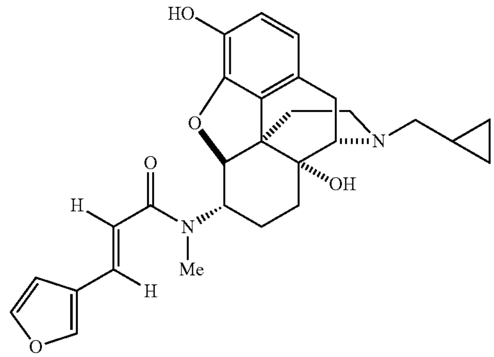 | 0.18 ± 0.01 | 87 | 1.34 ± 0.05 | 6 |
| II-63 | 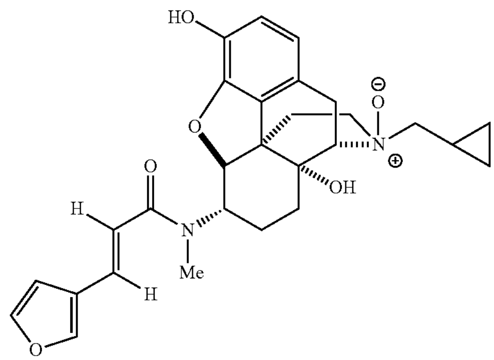 | 0.13 ± 0.01 | 91 | 0.23 ± 0.07 | 84 |
| I-2 | 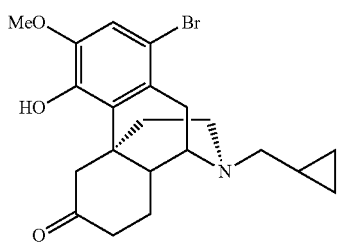 | 0.14 ± 0.02 | 90 | 1.10 ± 0.06 | 22 |
| I-1 | 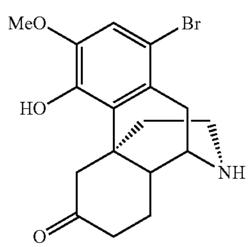 | 0.21 ± 0.01 | 85 | 1.18 ± 0.10 | 17 |
| I-3 | 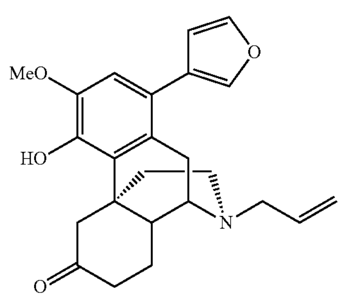 | 0.11 ± 0.00 | 92 | 1.12 ± 0.01 | 21 |

TABLE 2-continued

| | | TLR9 Inhibition | | | |
|---|---|---|---|---|---|
| Compound ID | Chemical Structure | OD 650 nm (mean ± sd) 10 μM | % Inhibition * (mean) | OD 650 nm (mean ± sd) 100 nM | % Inhibition * (mean) |
| I-7 | | 0.16 ± 0.01 | 89 | 1.14 ± 0.03 | 20 |
| II-1 | | 0.19 ± −.02 | 86 | 0.97 ± 0.04 | 32 |
| II-2 | | 0.12 ± 0.01 | 92 | 1.23 ± 0.05 | 13 |
| II-4 | | 0.11 ± 0.01 | 92 | 1.18 ± 0.06 | 17 |
| I-8 | | 0.11 ± 0.01 | 92 | 1.13 ± 0.07 | 20 |

TABLE 2-continued

| | | TLR9 Inhibition | | | |
|---|---|---|---|---|---|
| Compound ID | Chemical Structure | OD 650 nm (mean ± sd) 10 μM | % Inhibition * (mean) | OD 650 nm (mean ± sd) 100 nM | % Inhibition * (mean) |
| I-11 | | 1.98 ± 0.09 | −39 | 1.49 ± 0.04 | −5 |
| I-12 | | 0.13 ± 0.01 | 91 | 1.19 ± 0.07 | 16 |
| I-13 | | 0.13 ± 0.01 | 91 | 1.34 ± 0.12 | 6 |
| I-27 | | 0.10 ± 0.00 | 93 | 1.13 ± 0.04 | 20 |
| II-15 | | 0.23 ± 0.03 | 84 | 1.22 ± 0.06 | 14 |

TABLE 2-continued

TLR9 Inhibition

| Compound ID | Chemical Structure | OD 650 nm (mean ± sd) 10 μM | % Inhibition * (mean) | OD 650 nm (mean ± sd) 100 nM | % Inhibition * (mean) |
|---|---|---|---|---|---|
| II-16 | 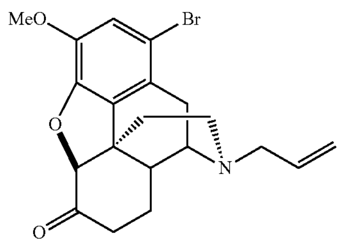 | 1.24 ± 0.11 | 13 | 1.43 ± 0.01 | −1 |
| II-23 | 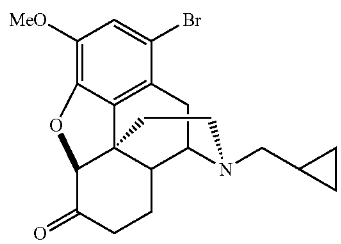 | 0.53 ± 0.05 | 63 | 1.16 ± 0.01 | 18 |
| II-21 | 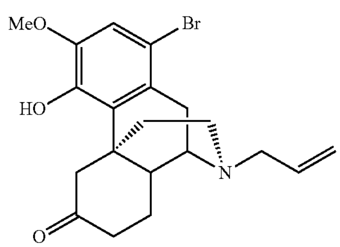 | 0.23 ± 0.01 | 84 | 1.40 ± 0.02 | 2 |
| I-5 | 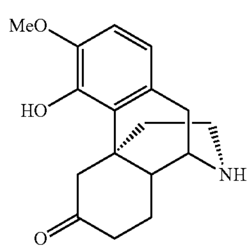 | 0.87 ± 0.04 | 38 | 1.31 ± 0.09 | 8 |
| I-4 | 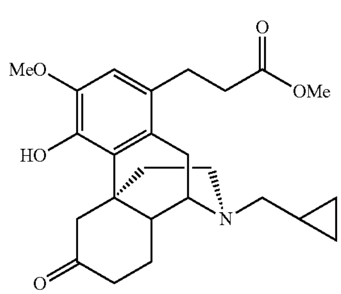 | 0.46 ± 0.05 | 68 | 1.17 ± 0.06 | 18 |

TABLE 2-continued

| | | TLR9 Inhibition | | | |
|---|---|---|---|---|---|
| Compound ID | Chemical Structure | OD 650 nm (mean ± sd) 10 μM | % Inhibition * (mean) | OD 650 nm (mean ± sd) 100 nM | % Inhibition * (mean) |
| I-6 | | 0.12 ± 0.02 | 91 | 1.29 ± 0.07 | 9 |
| II-5 | | 0.14 ± 0.00 | 90 | 1.11 ± 0.03 | 22 |
| II-11 | | 0.44 ± 0.05 | 69 | 1.22 ± 0.10 | 14 |
| II-14 | | 0.13 ± 0.00 | 91 | 1.18 ± 0.05 | 17 |
| II-7 | | 0.13 ± 0.02 | 91 | 1.32 ± 0.08 | 7 |

TABLE 2-continued

TLR9 Inhibition

| Compound ID | Chemical Structure | OD 650 nm (mean ± sd) 10 μM | % Inhibition * (mean) | OD 650 nm (mean ± sd) 100 nM | % Inhibition * (mean) |
|---|---|---|---|---|---|
| II-91 | 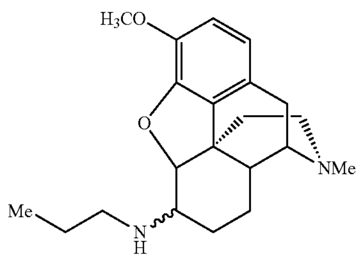 | 0.09 ± 0.01 | 93 | 0.12 ± 0.01 | 92 |
| II-92 | 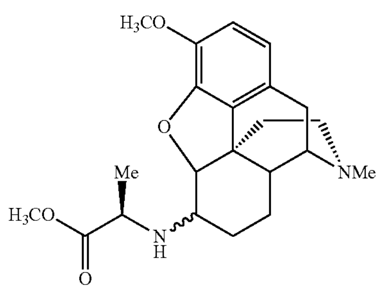 | 0.73 ± 0.06 | 48 | 1.09 ± 0.03 | 23 |
| II-93 | 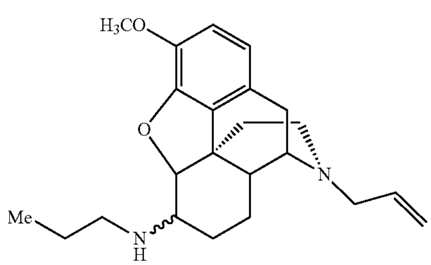 | 0.11 ± 0.01 | 92 | 0.12 ± 0.00 | 91 |
| II-21 | 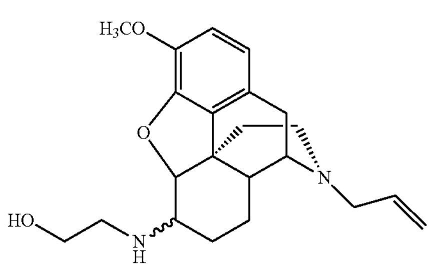 | 0.09 ± 0.01 | 93 | 0.19 ± 0.02 | 87 |
| II-94a | Isomer 1 | 1.16 ± 0.08 | 18 | 1.13 ± 0.04 | 20 |

TABLE 2-continued
| | | TLR9 Inhibition | | | |
|---|---|---|---|---|---|
| Compound ID | Chemical Structure | OD 650 nm (mean ± sd) 10 μM | % Inhibition * (mean) | OD 650 nm (mean ± sd) 100 nM | % Inhibition * (mean) |
| II-94b | 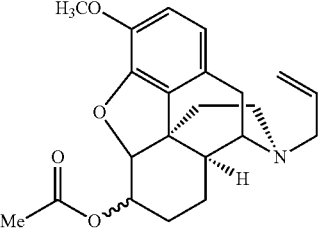 Isomer 2 | 1.30 ± 0.05 | 8 | 1.17 ± 0.03 | 17 |
| II-9 | 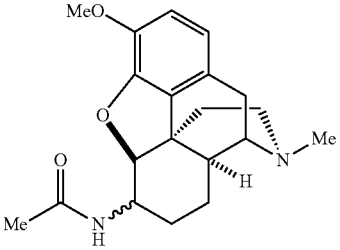 | 1.00 ± 0.02 | 29 | 1.25 ± 0.09 | 12 |
| II-20 | 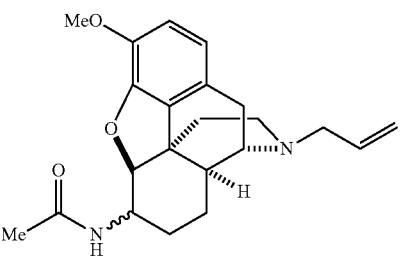 [SMILES: C=CCN1CC[C@@]23c4c5ccc(OC)c4O[C@@H]2C(NC(C)=O)CC[C@@H]3[C@@H]1C5] | 1.07 ± 0.04 | 25 | 1.29 ± 0.02 | 9 |
| II-19 | 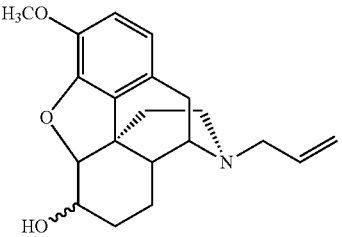 | 0.15 ± 0.01 | 90 | 1.19 ± 0.03 | 16 |
| II-8 | 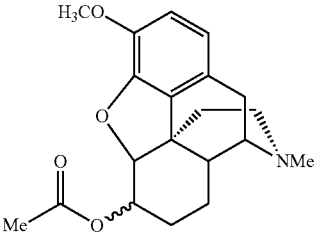 | 1.33 ± 0.06 | 7 | 1.15 ± 0.07 | 19 |

TABLE 2-continued
| | | TLR9 Inhibition | | | |
|---|---|---|---|---|---|
| Compound ID | Chemical Structure | OD 650 nm (mean ± sd) 10 μM | % Inhibition * (mean) | OD 650 nm (mean ± sd) 100 nM | % Inhibition * (mean) |
| II-53a | 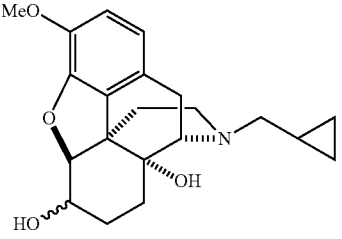 [SMILES: COc1ccc2c3c1O[C@@H]1C(O)CC[C@]4(O)[C@H](C2)N(CC2CC2)CC[C@@]314] Isomer 1 | 1.32 ± 0.13 | 7 | 1.22 ± 0.05 | 14 |
| II-53b | 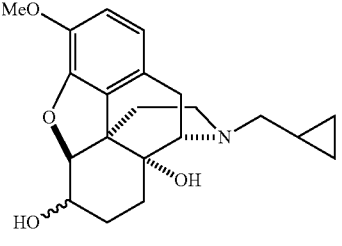 [SMILES: COc1ccc2c3c1O[C@@H]1C(O)CC[C@]4(O)[C@H](C2)N(CC2CC2)CC[C@@]314] Isomer 2 | 1.00 ± 0.03 | 29 | 1.41 ± 0.09 | 1 |
| II-74 | 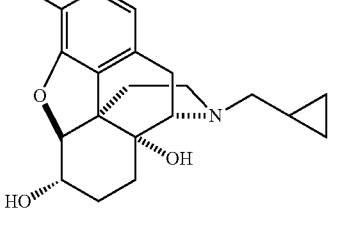 | 1.26 ± 0.06 | 11 | 1.19 ± 0.06 | 16 |
| II-95 | 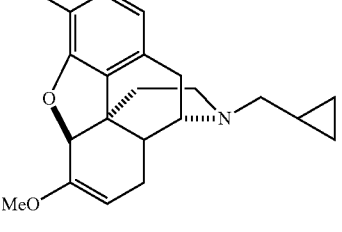 | 0.37 ± 0.03 | 74 | 1.11 ± 0.04 | 22 |
| II-96 | 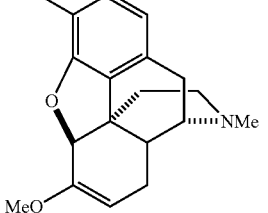 | 0.42 ± 0.02 | 71 | 1.15 ± 0.06 | 19 |

TABLE 2-continued

TLR9 Inhibition

| Compound ID | Chemical Structure | OD 650 nm (mean ± sd) 10 μM | % Inhibition * (mean) | OD 650 nm (mean ± sd) 100 nM | % Inhibition * (mean) |
|---|---|---|---|---|---|
| II-97 | 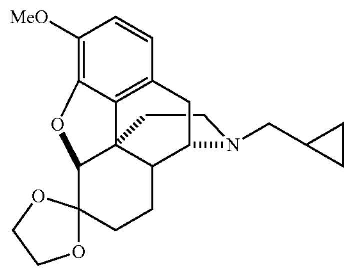 [SMILES: COc1ccc2c3c1O[C@@H]1C4(CCC5[C@H](C2)N(CC2CC2)CC[C@]351)OCCO4] | 1.42 ± 0.07 | 0 | 1.22 ± 0.02 | 14 |
| II-98 | 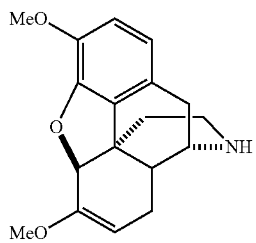 [SMILES: COC1=CCC2[C@@H]3Cc4ccc(OC)c5c4[C@]2(CCN3)[C@@H]1O5] | 0.56 ± 0.03 | 60 | 1.02 ± 0.02 | 28 |
| II-99 | 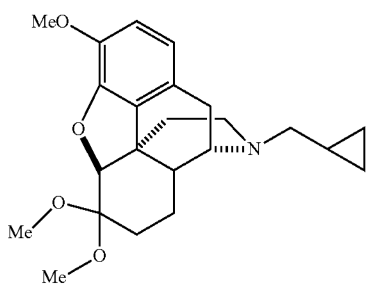 [SMILES: COc1ccc2c3c1O[C@@H]1C(OC)(OC)CCC4[C@H](C2)N(CC2CC2)CC[C@]341] | 0.14 ± 0.01 | 90 | 1.32 ± 0.00 | 7 |
| II-100 | 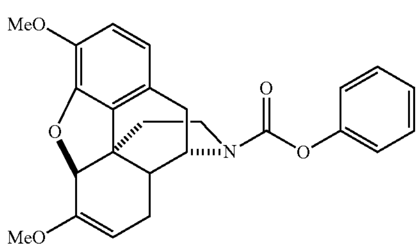 [SMILES: COC1=CCC2[C@@H]3Cc4ccc(OC)c5c4[C@]2(CCN3C(=O)Oc2ccccc2)[C@@H]1O5] | 1.45 ± 0.11 | −2 | 1.16 ± 0.02 | 18 |
| II-12 | 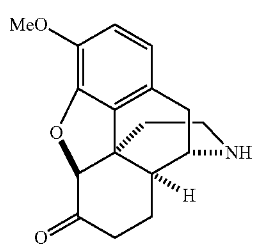 [SMILES: COc1ccc2c3c1O[C@@H]1C(=O)CC[C@@H]4[C@H](C2)NCC[C@@]314] | 0.81 ± 0.03 | 43 | 1.12 ± 0.08 | 21 |

TABLE 2-continued

TLR9 Inhibition

| Compound ID | Chemical Structure | OD 650 nm (mean ± sd) 10 μM | % Inhibition * (mean) 10 μM | OD 650 nm (mean ± sd) 100 nM | % Inhibition * (mean) 100 nM |
|---|---|---|---|---|---|
| II-101 | 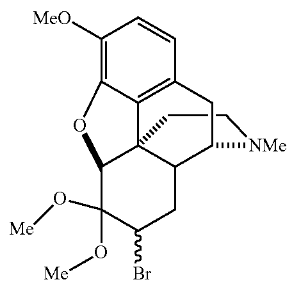 [SMILES: COc1ccc2c3c1O[C@@H]1C(OC)(OC)C(Br)CC4[C@H](C2)N(C)CC[C@]341] | 0.94 ± 0.02 | 34 | 1.35 ± 0.06 | 5 |
| III-1 | 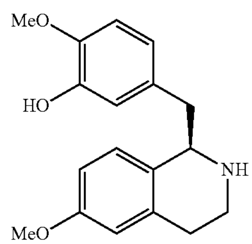 [SMILES: COc1ccc2c(c1)CCN[C@@H]2Cc1ccc(OC)c(O)c1] | 0.67 ± 0.01 | 53 | 1.34 ± 0.06 | 6 |
| II-39 | 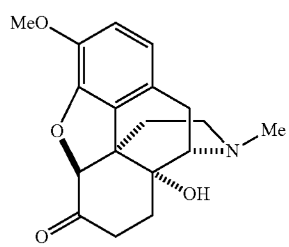 [SMILES: COc1ccc2c3c1O[C@@H]1C(=O)CC[C@]4(O)[C@H](C2)N(C)CC[C@@]314] | 1.06 ± 0.06 | 25 | 1.23 ± 0.03 | 14 |
| II-10 | 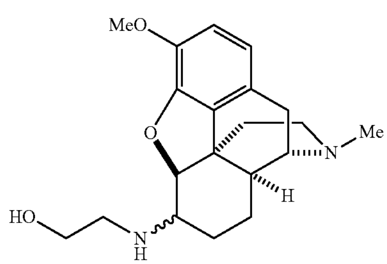 [SMILES: COc1ccc2c3c1O[C@@H]1C(NCCO)CC[C@@H]4[C@H](C2)N(C)CC[C@@]314] | 0.10 ± 0.01 | 93 | 0.24 ± 0.02 | 83 |
| I-16 | 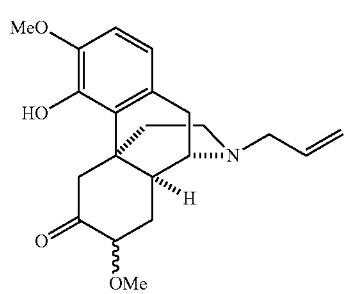 [SMILES: C=CCN1CC[C@@]23CC(=O)C(OC)C[C@@H]2[C@@H]1Cc1ccc(OC)c(O)c13] | 0.91 ± 0.04 | 36 | 1.50 ± 0.01 | −5 |

TABLE 2-continued

TLR9 Inhibition

| Compound ID | Chemical Structure | OD 650 nm (mean ± sd) 10 μM | % Inhibition * (mean) 10 μM | OD 650 nm (mean ± sd) 100 nM | % Inhibition * (mean) 100 nM |
|---|---|---|---|---|---|
| I-28 | (structure) | 0.12 ± 0.01 | 91 | 1.24 ± 0.02 | 13 |
| I-10 | (structure) | 1.04 ± 0.08 | 27 | 1.32 ± 0.04 | 7 |
| I-29 | (structure) | 0.11 ± 0.00 | 92 | 1.06 ± 0.03 | 25 |
| II-61 | (structure) | 1.22 ± 0.07 | 14 | 1.23 ± 0.02 | 13 |

* Control (no activator) = 0.14 OD 650 nm (n = 12); Activator (ODN2006) = 1.42 OD 650 nm (n = 12)

This screening experiment identified those (+)-morphinan compounds comprising the greatest TLR9 antagonist activity. Even at a concentration as low as 100 nM, some compounds inhibited TLR9 in excess of 90%.

Example 3

Analgesic Assessment of (+)-Naloxone on Mechanical Allodynia

Neuropathic pain affects approximately 1% of the U.S. population and is extremely difficult to manage. Usually the pain is chronic, severe, and fails to respond to traditional analgesic drugs. Fortunately, one of the most widely used animal models for neuropathic pain closely mimics the pain endured by patients. In this model, termed the chronic constriction injury (CCI) or Bennett model, four closely spaced ligatures tied loosely around the sciatic nerve of a rat cause demyelination of the nerve, resulting in spontaneous pain, such as prolonged paw elevation and licking of the ligated paw. Induced pain in the nerve-injured limb can be measured using Von Frey filaments, applied to the plantar surface of the paw to test for responses to non-noxious tactile stimulation. The onset of this heightened mechanical allodynia is quite rapid and it persists for 2-3 months.

In this example, the CCI ligation was performed on the left sciatic nerve in three groups of rats. Von Frey testing of mechanical allodynia was performed on both paws on Day 14 to determine the analgesic efficacy of the test agent. The testing was performed pre-dosing, and at 30 and 90 minutes post-dosing.

Animals. A total of thirty-four (34) male Sprague-Dawley rats were ordered from Harlan Sprague-Dawley. The animals were specific pathogen free and weighed approximately 175-200 grams upon arrival. A visual health inspection was performed on each animal to include evaluation of the coat, extremities and abnormal signs in posture or movement. Animals were individually identified with a unique ear tag assigned at receipt. The animals were individually housed in clear polycarbonate plastic cages and received enrichment in the way of Enrich-o-cobs bedding. Cage cards were affixed to their cages that identified study number, animal number, treatment designation, species/strain, and gender. The animals were acclimated for 5 days prior to the commencement of the experimental procedures. The room number in which the animals were housed throughout the study period was detailed in the study records. The temperature was maintained at 18-26° C. (64-79° F.) with a relative humidity of 30-70%. Temperature and humidity were monitored and daily minimums and maximums recorded.

Treatment groups. The animals were allocated to treatment groups based on their baseline Von Frey data, measured prior to surgery. The mechanical allodynia scores for each group were reviewed to ensure that the mean values and standard deviation satisfied the assumption of homogeneity. Table 3 presents the treatment groups. Thirty-one (31) animals were used on the study. Thirty (30) animals were initially allocated to treatment groups, and the remaining four (4) animals were held as spares. One spare was then used to replace an animal that died during surgery. Body weights were taken one day after arrival, prior to surgery and weekly thereafter. On Day 14, after the final behavioral testing, the animals were euthanized by carbon dioxide asphyxiation. No necropsy was performed nor tissues collected.

TABLE 3

Treatment Groups

| Group | Description | Test Article | Route/ Frequency | Dose mg/kg | #/ Group |
|---|---|---|---|---|---|
| 1 | Bennett surgery | Vehicle | S.C. injection | 0 | 10 |
| 2 | Bennett surgery | Gabapentin | I.P. injection | 100 mg/kg | 10 |
| 3 | Bennett surgery | (+)-Naloxone•HCl | S.C. injection | 66.7 mg/kg | 10 |

Surgery. All surgeries were performed under aseptic conditions. Prior to surgery, the rats were sedated using inhaled Isoflurane anesthetic. The left leg was shaved and prepped. The common sciatic nerve was exposed and freed from adherent tissue at mid-thigh by separating the muscle (biceps femoris) by blunt dissection. Proximal to the sciatic nerve's trifurcation; approximately 7 mm of nerve was freed from the adhering tissue. Four ligatures, approximately 1 mm apart, were tied loosely around the nerve using 6.0 chromic catgut. Each of the sutures was tied loosely with a square knot around the sciatic nerve. A brief twitch in the muscle surrounding the exposure was an indicator of the desired degree of constriction. The site was then closed using the appropriate suture material. Post-operative care and observations were carried out until the animal recovered consciousness. Animals were observed for dragging (from inadvertent surgical damage) on Days 1 & 3 post-operatively and daily for signs of ill health and general well being.

Behavioral testing. The animals underwent a series of behavioral testing for neuropathic pain assessment. A Von Frey test of mechanical allodynia was performed on both hind paws prior to surgery to achieve a baseline measurement for randomization and then following surgery on Day 14 (test article efficacy) according to Table 4.

TABLE 4

Behavioral Testing Schedule

| Day | Time point |
|---|---|
| 0 | Baseline (for randomization) |
| 14 | Pre-dose |
| 14 | 30 minutes post-dose |
| 14 | 90 minutes post-dose |

Mechanical allodynia. Twice prior to surgery, the animals were acclimated to the allodynia apparatus. This habituated the rats to the testing devices to familiarize them with the apparatus so they were calm at the time of testing. The test for mechanical allodynia was used to assess the anti-nociceptive properties of analgesic compounds. Animals were first habituated to the testing chamber so that they were calm enough for their pain threshold to be assessed. A technician blind to the treatment groups applied light pressure to both hindpaws of the rat using a series of graded nylon filaments (Von Frey filaments) of increasing diameter. The filaments were pressed perpendicularly against the ventral surface of the paw until they bent and the rat responded by withdrawing its paw when this was considered painful. Threshold allodynia was determined using the Chaplan up-down method which provided the precise force for withdrawal for each rat using a psychophysical scale of testing. Both the left and right hindpaws were tested at each time point. The order of testing was the ipsilateral (affected) limb followed by the contralateral limb. There were approximately 20 minutes in between testing the two limbs.

Dosing. On Day 14, animals in Groups 1 and 3 received an S.C. injection of either vehicle or (+)-naloxone•HCl according to Table 3. They were dosed at 1 mL/kg. On Day 14, animals in Group 2 received an I.P. injection of Gabapentin according to Table 3. They were also dosed at 1 mL/kg.

Statistics. The allodynia data were compared among groups and between paws and time points with a 3×2 ANOVA. When data were significant ($p<0.05$), a Bonferroni post-hoc test was applied to determine individual group differences.

Results. The mechanical allodynia testing was performed prior to surgery (baseline), and at Day 14 post-surgery at pre-dosing, and 30 and 90 min post-dosing. The baseline data are not included in the figures, but all animals achieved the maximal score of 17 g, indicating no sensitivity to the highest force of filament used in this test. At pre-dose testing on Day 14, there were some animals that continued to respond with a score of 17 g. This indicated that the surgery had not been effective at causing neuropathic pain in this subset of animals, and therefore, they were removed from the data set, and excluded from statistical analyses. The final sample sizes and the allodynia data are presented in FIG. 2A for the left paw (affected) and FIG. 2B (unaffected) for the right paw.

Figure 2A:
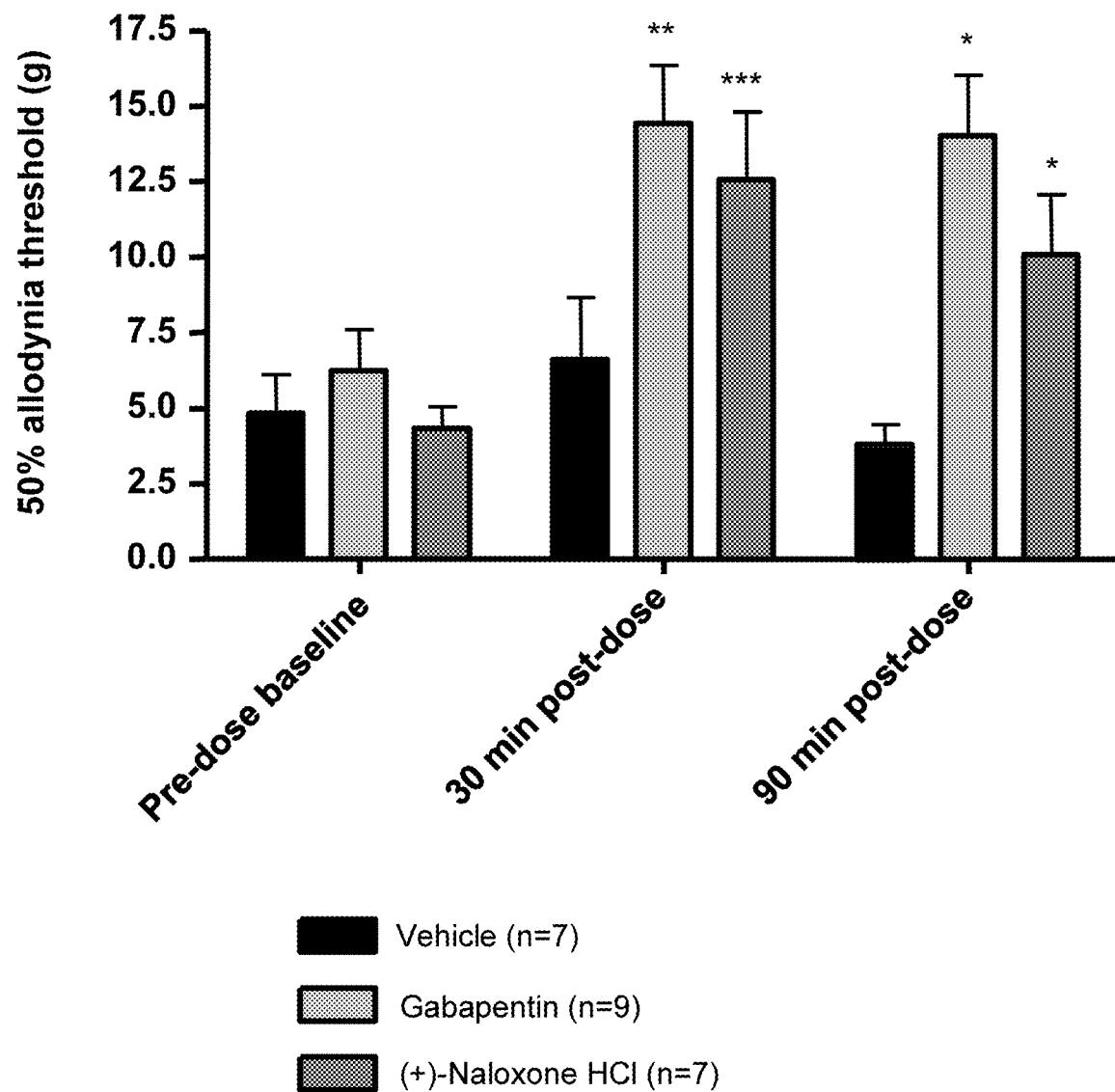
FIGS. 2A-2B illustrate the analgesic effects of (+)-naloxone on mechanical allodynia in rats. Plotted is 50% allodynia threshold at three timepoints for each treatment group on Day 14. Bars represent mean +/−SEM.
Figure 2B:
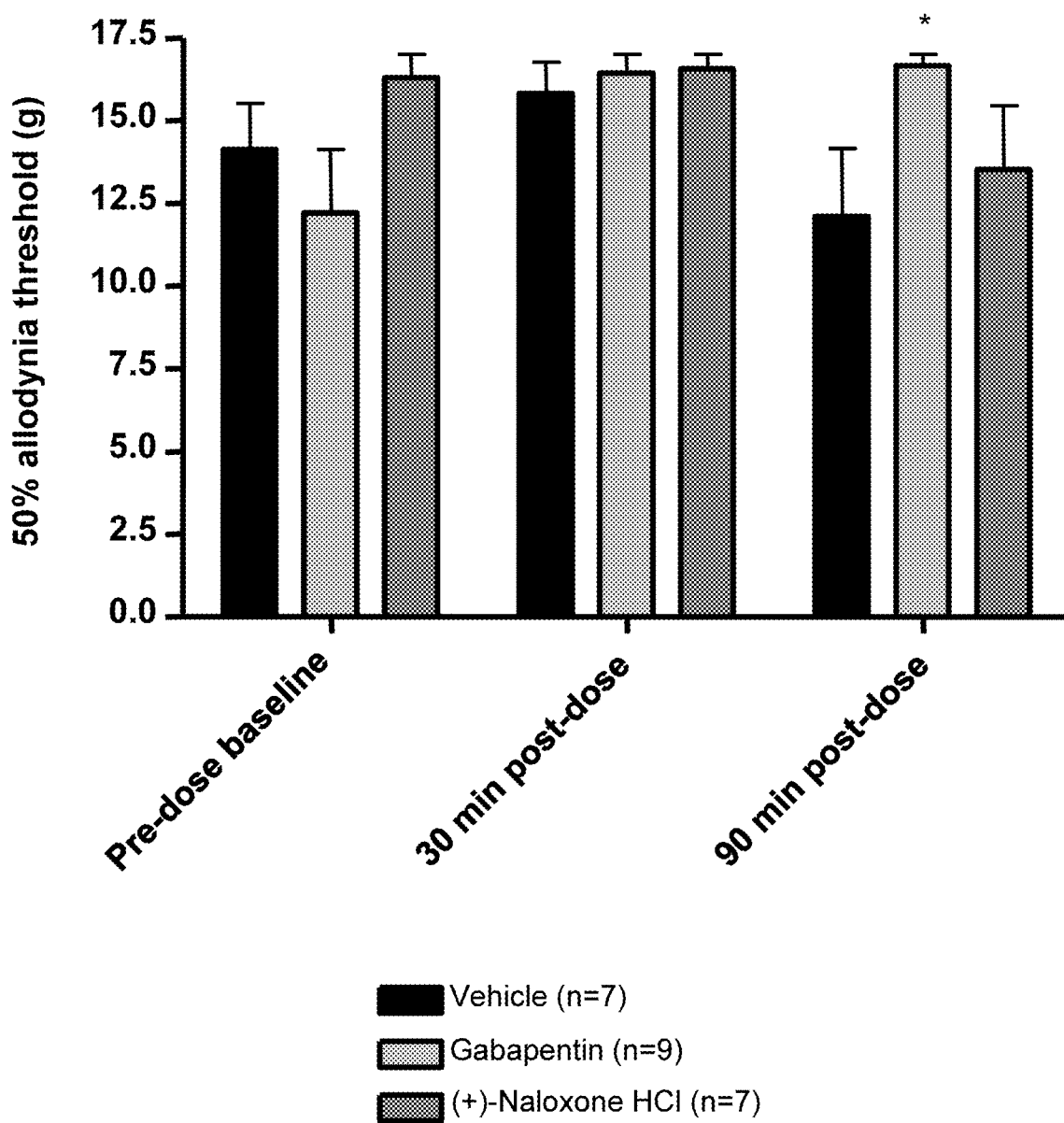

The data in FIG. 2A demonstrate a significant allodynia in the left paw for all three groups in relation to the pre-surgery baseline data (p<0.01 for treatment, p<0.001 for time). After dosing, both Gabapentin and (+)-naloxone were effective at significantly reducing the allodynia at both 30 and 90 min. The right paw data are depicted in FIG. 2B and these data reveal that there was no allodynia in the right paw as expected in this model. There were no significant group differences or differences across time with the exception of the Gabapentin group, which demonstrated a higher threshold for mechanical allodynia testing at the 90 min timepoint than was observed in the vehicle group. This is not surprising, given that Gabapentin was administered peripherally and has a robust analgesic effect bilaterally.

Conclusions. This study examined the efficacy of the test agent, (+)-naloxone, to reduce allodynia in the left paw of animals that achieved neuropathic pain when tested on Day 14 post-surgery. The results showed that significant analgesia was achieved by (+)-naloxone at both timepoints tested, which was similar to the results of the positive control, Gabapentin. Thus, (+)-naloxone•HCl was an effective analgesic for reversing neuropathic pain over a timecourse of 30 and 90 min post-dosing on Day 14 using a dose of 66.7 mg/kg.

Example 4

Evaluation of (+)-Morphinans in Animal Model of Neuropathic Pain

The following example was designed to evaluate the effectiveness of several specific (+)-morphinans to reverse allodynia, as assessed by von Frey testing, in rats subjected to chronic constriction injury (CCI).

Allodynia was induced in a group of (male, Sprague-Dawley) rats essentially as described above in Example 3. Prior to surgery, animals were tested to establish their baseline von Frey scores. Any animal with a Log absolute von Frey score lower than 4.65 on either leg was excluded from the study. CCI surgery was performed on the left sciatic nerve as detailed above. On days 4 and 14 post-surgery, the animals were tested using the von Frey test of mechanical allodynia to ensure that allodynia was established.

Beginning at about day 14 post-surgery, the animals were dosed once a day for 4 days. Compounds II-25, II-93, II-62, and III-2 were tested. Table 5 presents the treatment groups. All drugs were administered intraperitoneally (i.p.). Allodynia was tested prior to and again 3 hrs after each dosing. Drug administration and testing was done blindly. After the 4$^{th}$ day of dosing, the animals were sacrificed, cardiac perfusion was performed, and spinal cords were removed and stored for further analysis.

TABLE 5

| Treatment groups | | |
|---|---|---|
| Condition | Dose | #/group |
| Control - saline | 0 | 46 |
| Gabapentin | 100 mg/kg?? | 24 |
| (+)-naloxone - ultra low | 0.071 mg/kg | 16 |
| (+)-naloxone - low | 0.71 mg/kg | 8 |
| (+)-naloxone - medium | 7.1 mg/kg | 8 |
| (+)-naloxone - high | 71 mg/kg | 8 |
| Cmpd II-25 - ultra low | 0.073 mg/kg | 8 |
| Cmpd II-25 - low | 0.73 mg/kg | 8 |
| Cmpd II-25 - medium | 7.3 mg/kg | 9 |
| Cmpd II-25 - high | 73 mg/kg | 10 |
| Cmpd II-93 - ultra low | 0.079 mg/kg | 8 |
| Cmpd II-93 - low | 0.79 mg/kg | 8 |
| Cmpd II-93 - medium | 7.9 mg/kg | 8 |
| Cmpd II-93 - high | 79 mg/kg | 8 |
| Cmpd II-62 - ultra low | 0.1 mg/kg | 8 |
| Cmpd II-62 - low | 1.0 mg/kg | 8 |
| Cmpd II-62 - medium | 10.1 mg/kg | 8 |
| Cmpd II-62 - high | 101 mg/kg | 7 |
| Cmpd III-2 - ultra low | 0.073 mg/kg | 8 |
| Cmpd III-2 - low | 0.73 mg/kg | 8 |
| Cmpd III-2 - medium | 7.3 mg/kg | 8 |
| Cmpd III-2 - high | 73 mg/kg | 8 |

All data were analyzed using 2-way ANOVA's with Bonferroni's post hoc test compared to saline unless otherwise stated. Area under curve (AUC) was calculated using Graphpad Prism and comparisons were made using 1-way ANOVA with Dunnet's post hoc test.

Figure 3A:
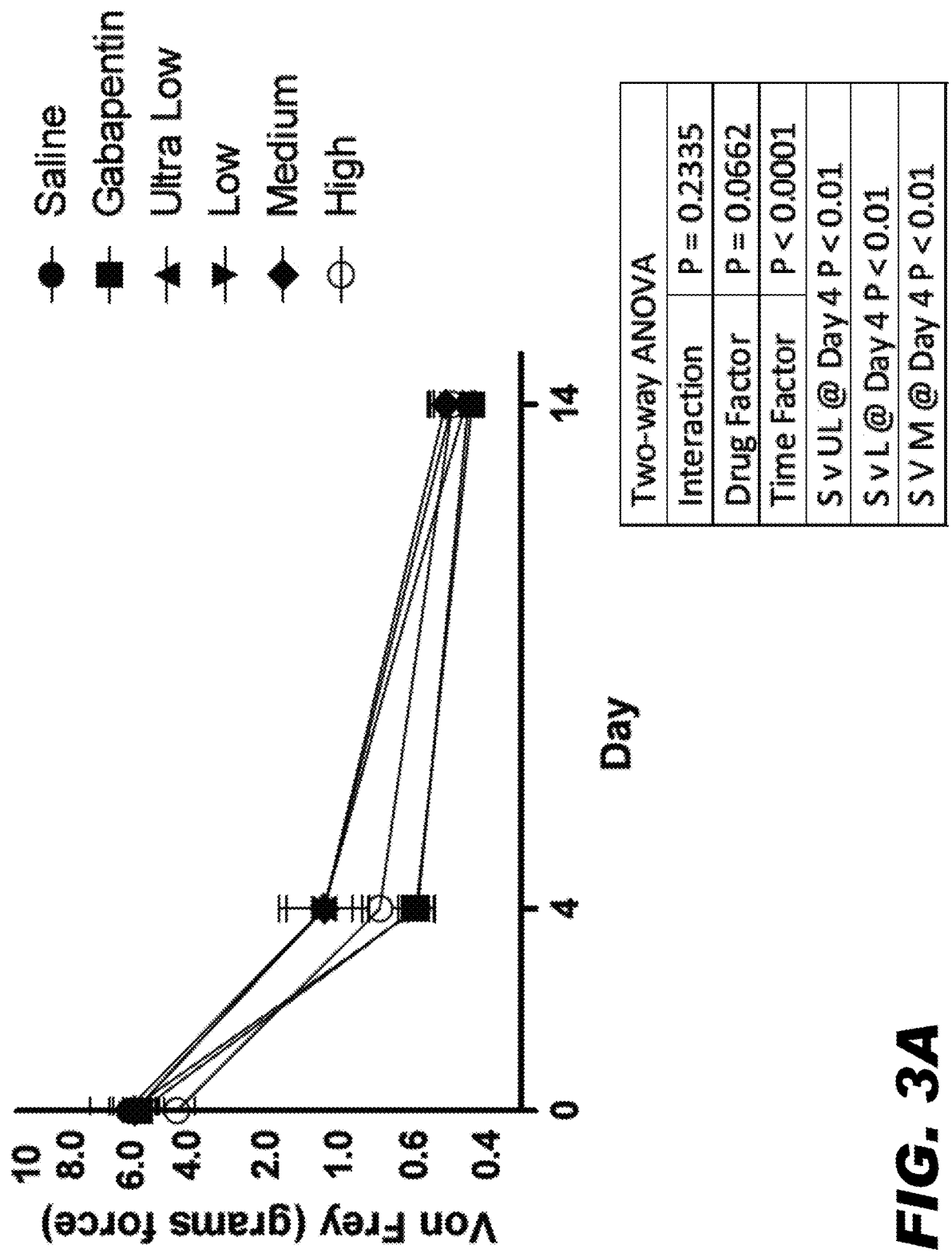
FIGS. 3A-3B depict development of allodynia.
Figure 3B:
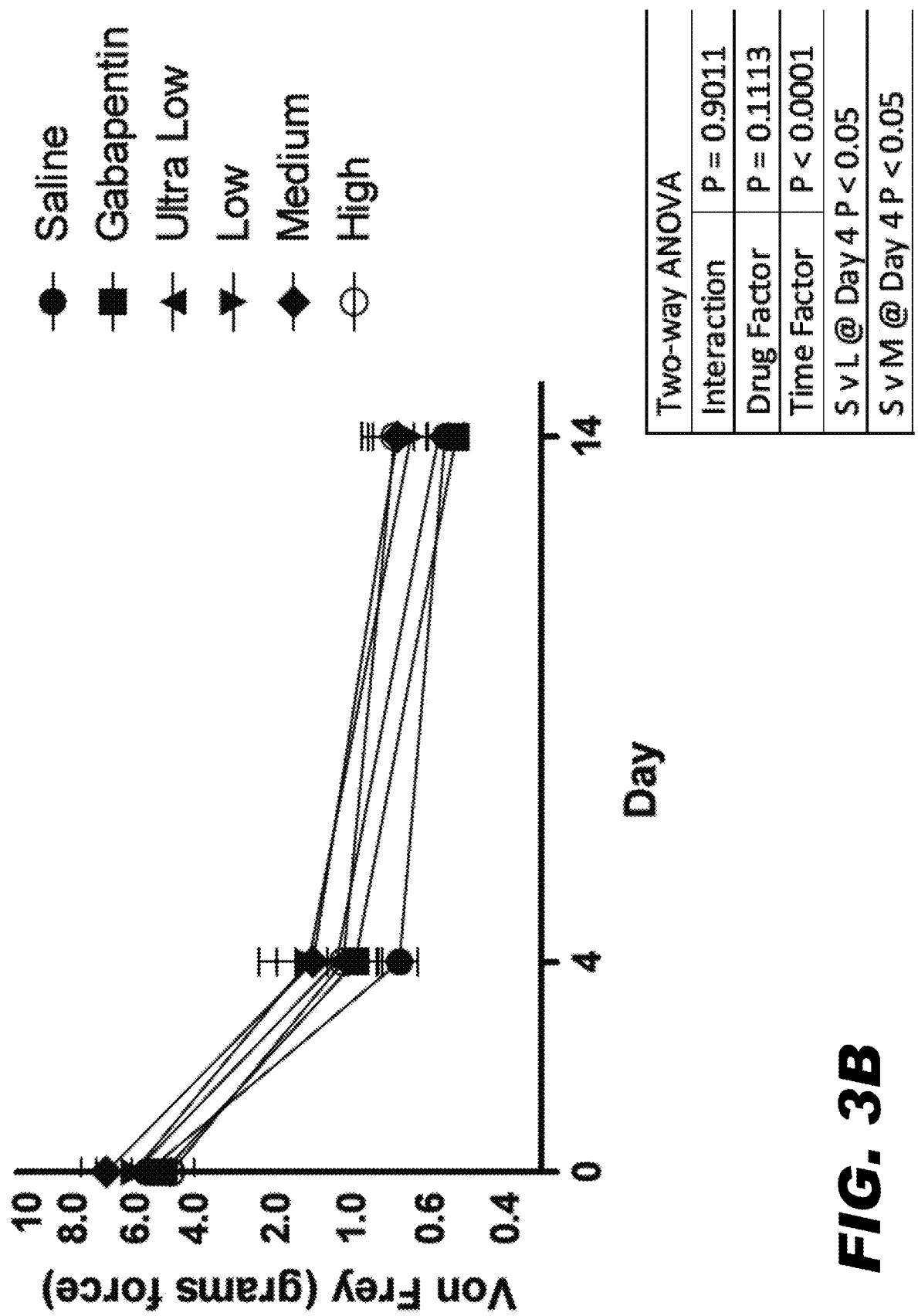
Figure 4A:
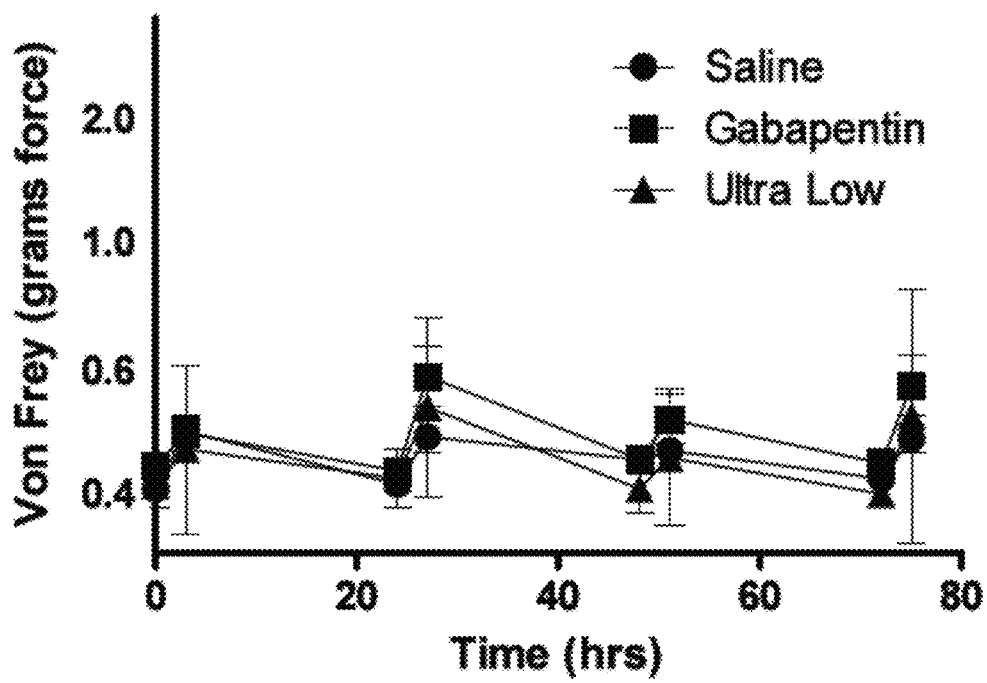
FIGS. 4A-4H present allodynia responses prior to and at several time points up to 3 hrs after treatment with saline, gabapentin, and various doses of compound II-25.
Figure 4B:
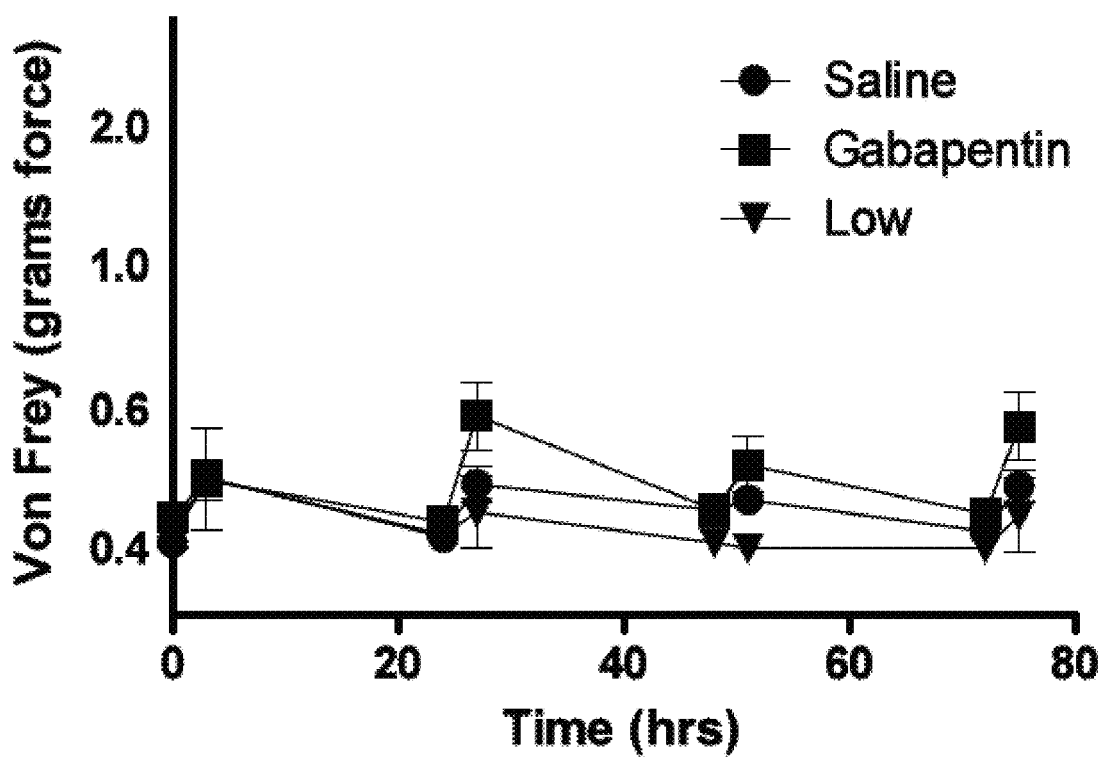
Figure 4C:
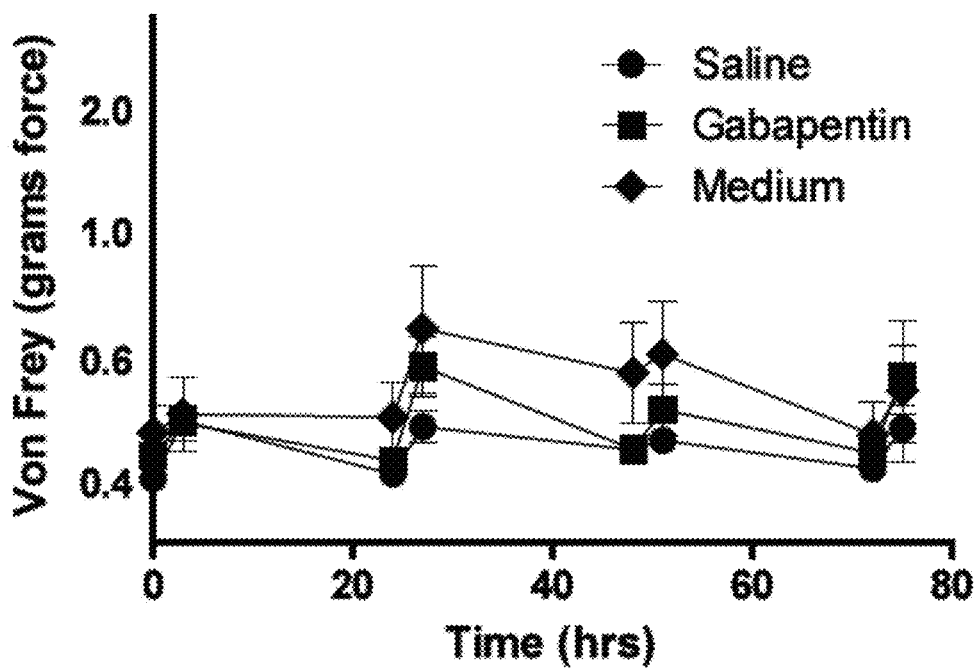
Figure 4D:
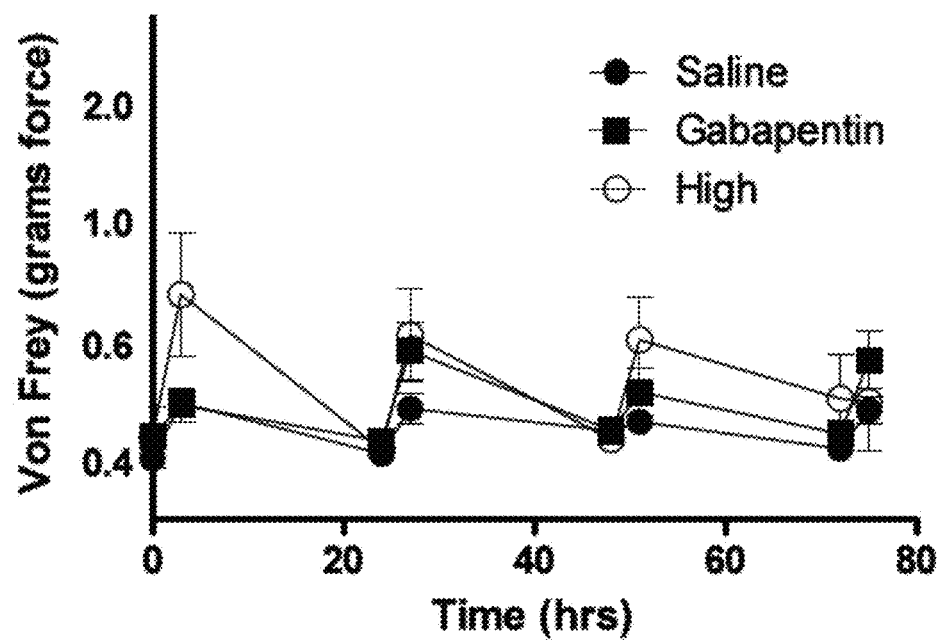
Figure 4E:
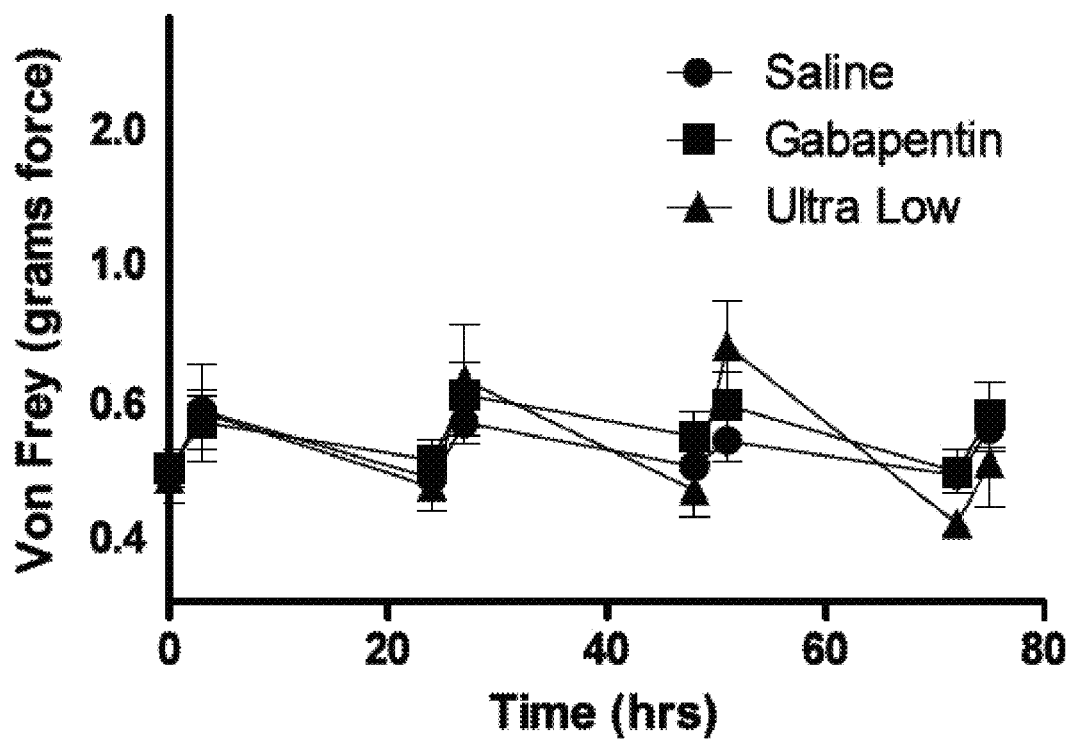
Figure 4F:
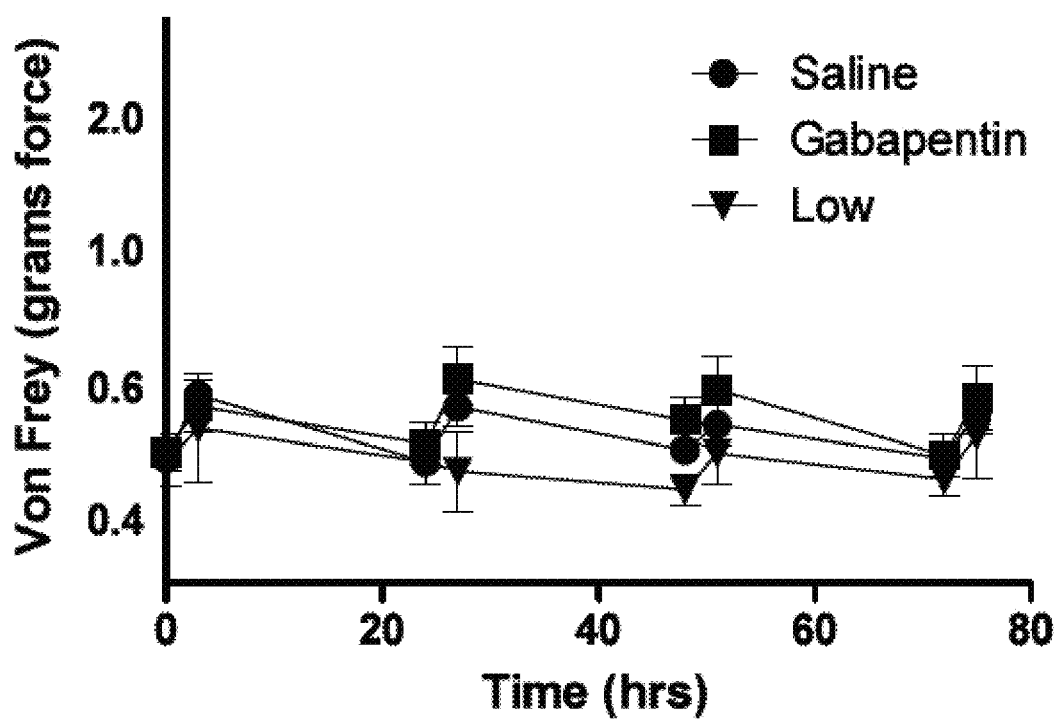
Figure 4G:
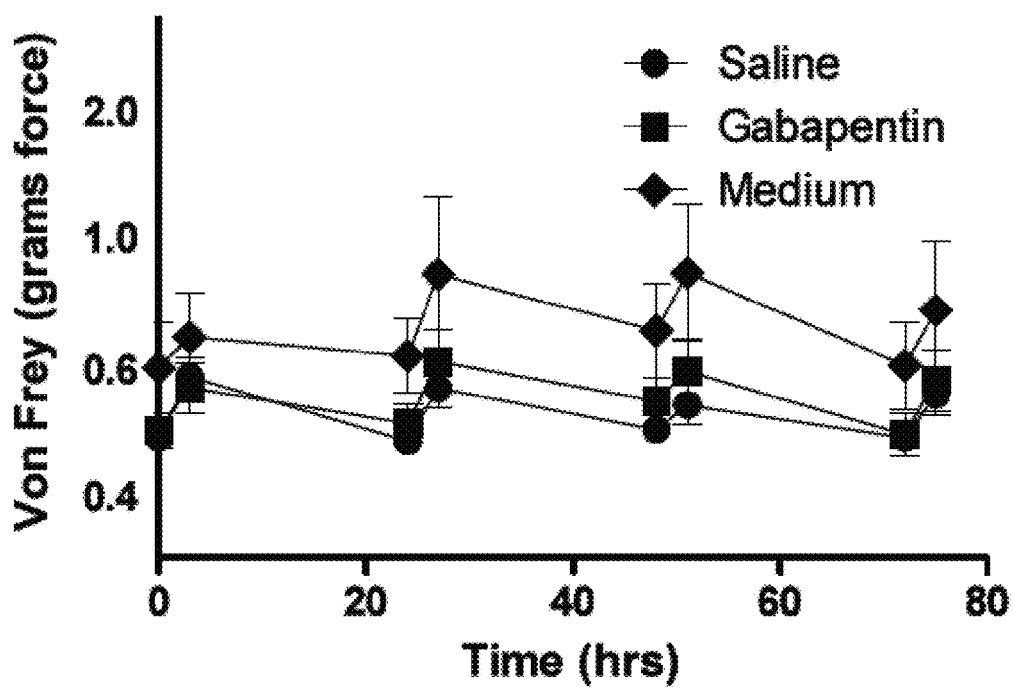
Figure 4H:
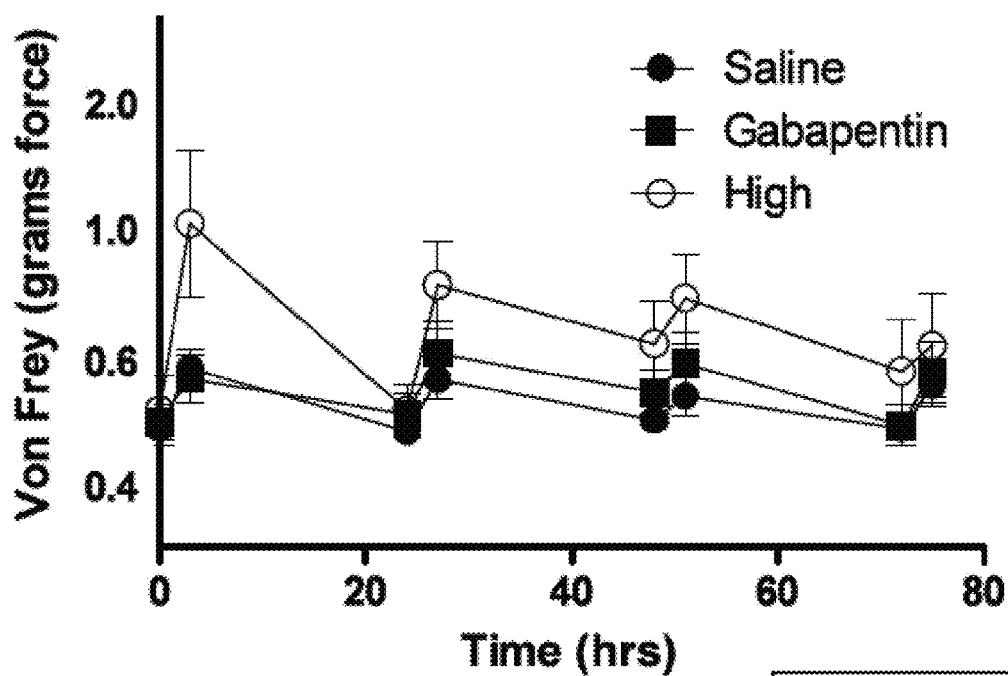

Results. All groups of rats developed allodynia. FIGS. 3A-3B present representative plots of the development of allodynia in which the von Frey scores are plotted at day 0 (prior to surgery) and days 4 and 14 post-surgery in various treatment groups. None of the rats treated with (+)-naloxone displayed any reversal of allodynia at any dose (data not shown). It appears, therefore, that (+)-naloxone is not effective at reversing allodynia 3 hours post dose using the current protocol.

Figure 5A:
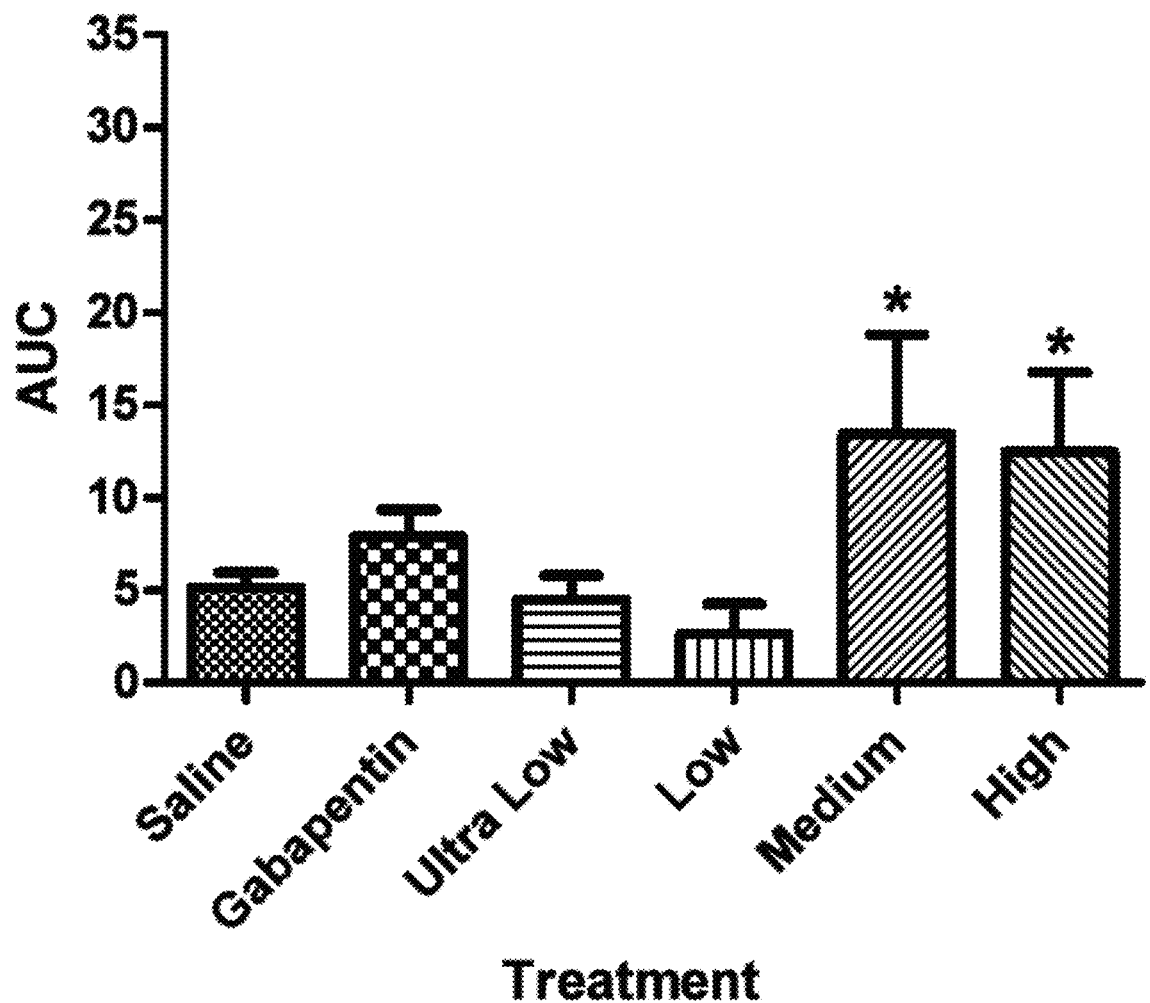
FIGS. 5A-5B present area under the curve (AUC) data for each group treated with compound II-25.
Figure 5B:
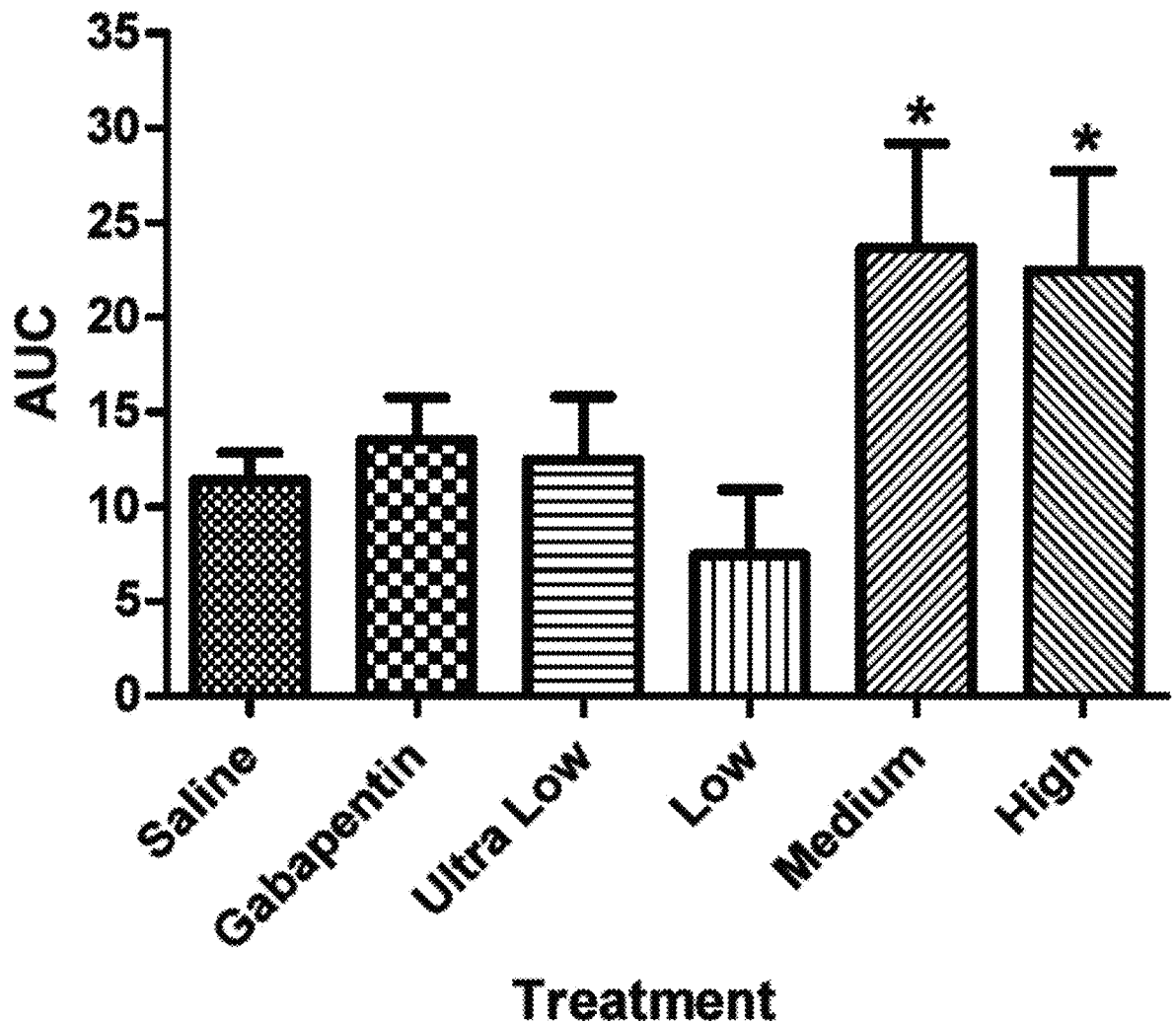
Figure 6A:
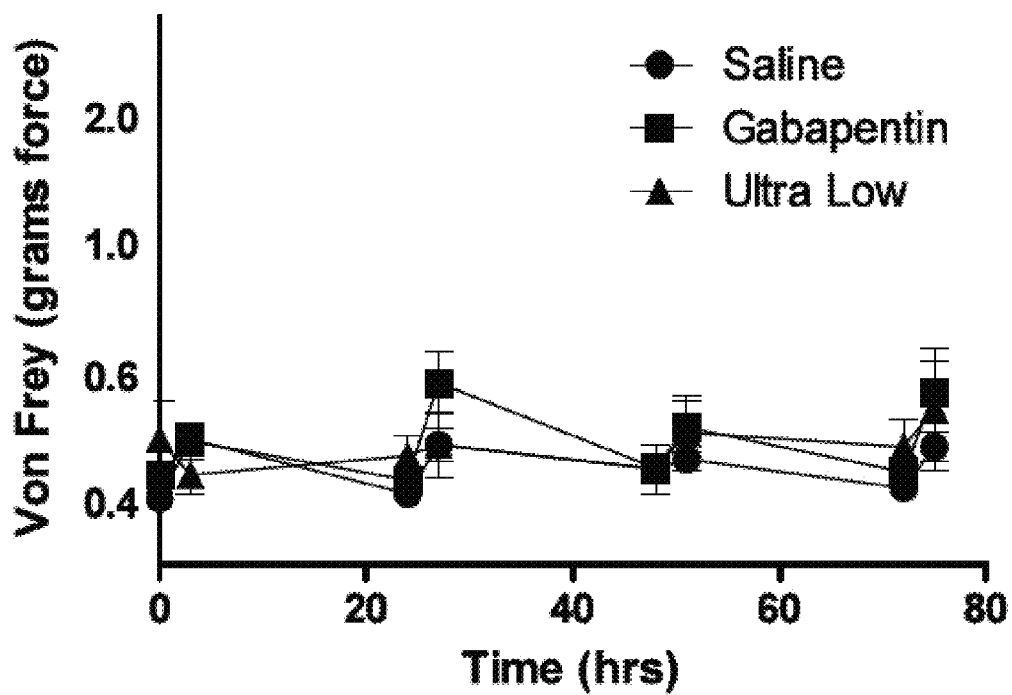
FIGS. 6A-6H depict allodynia responses prior to and at several time points up to 3 hrs after treatment with saline, gabapentin, and various doses of compound II-93.
Figure 6B:
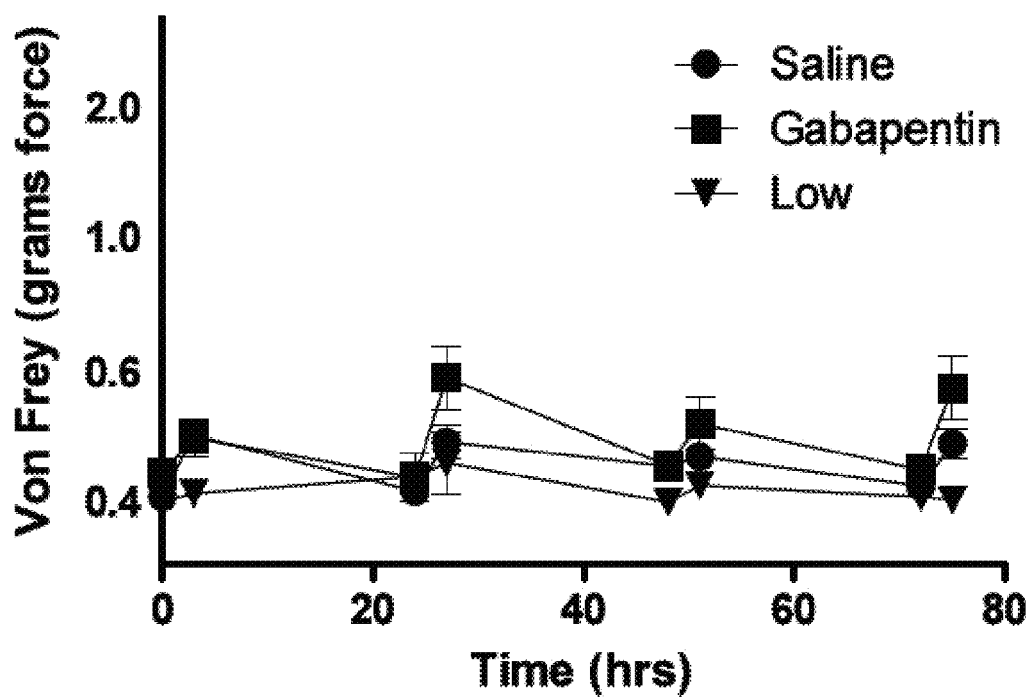
Figure 6C:
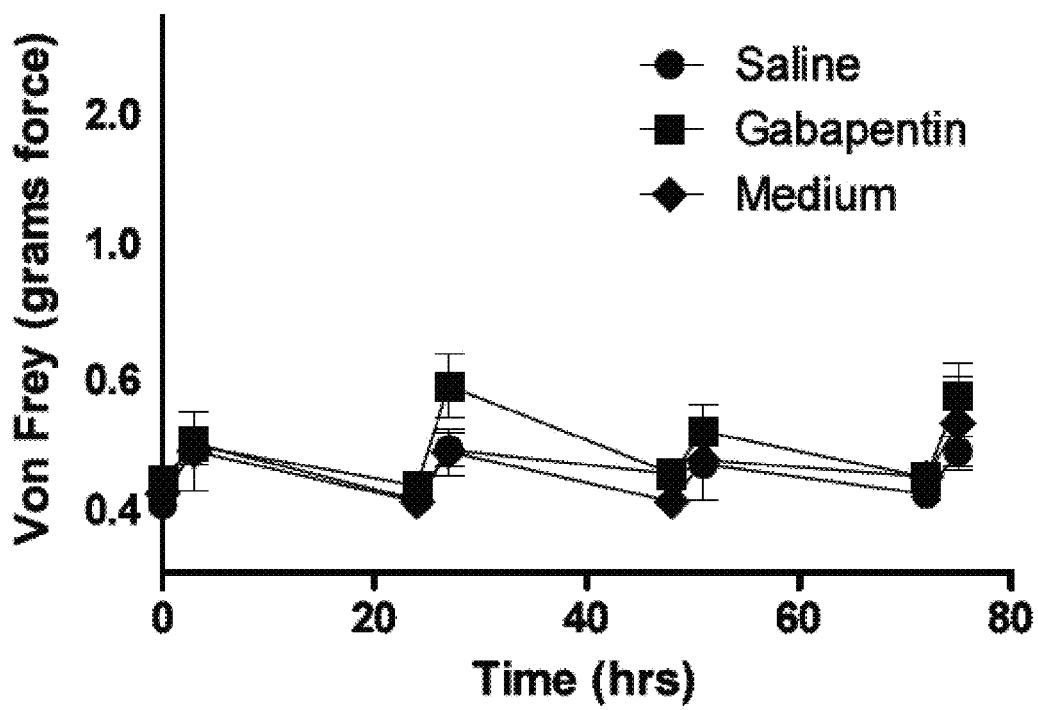
Figure 6D:
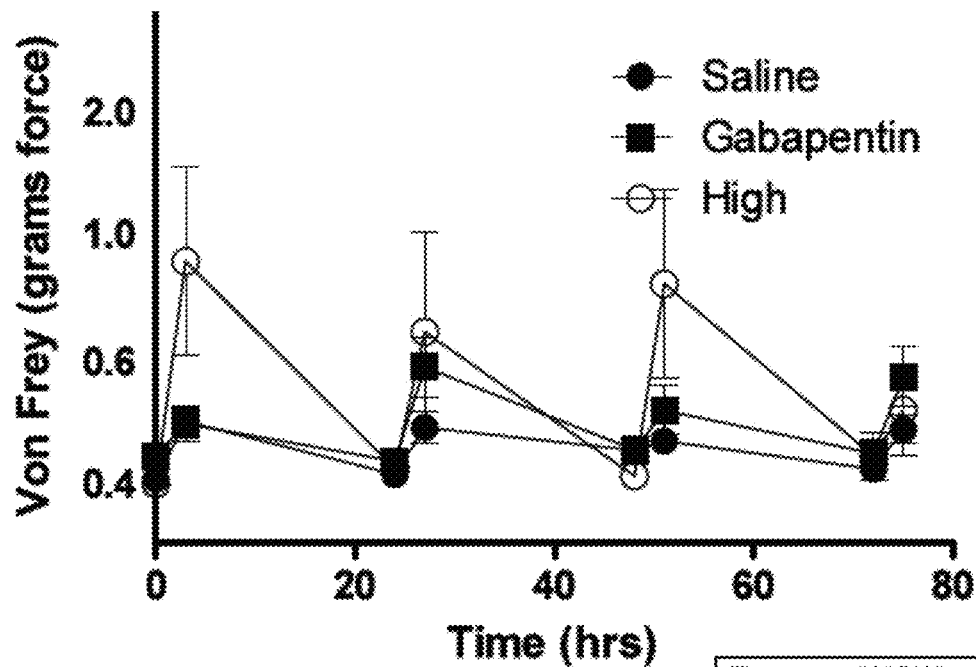
Figure 6E:
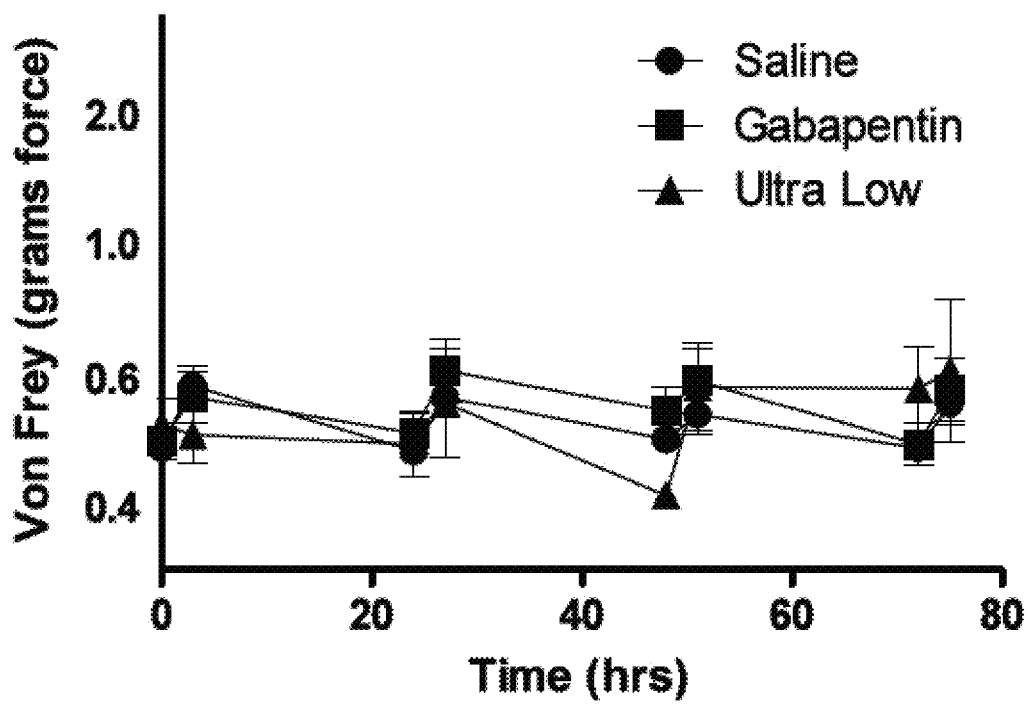
Figure 6F:
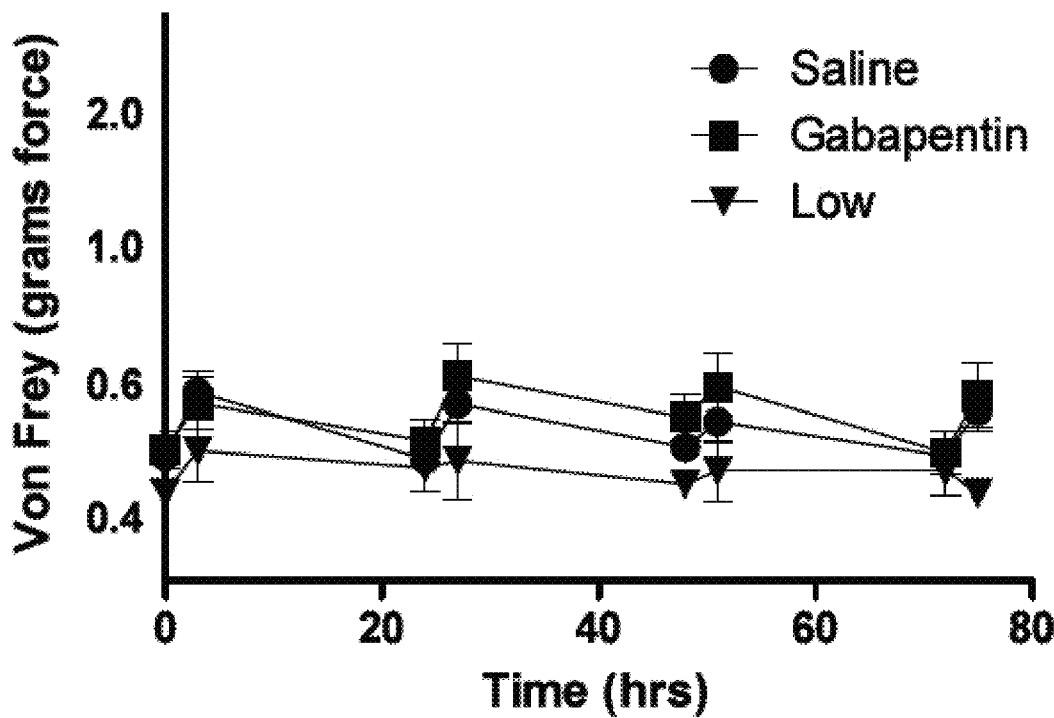
Figure 6G:
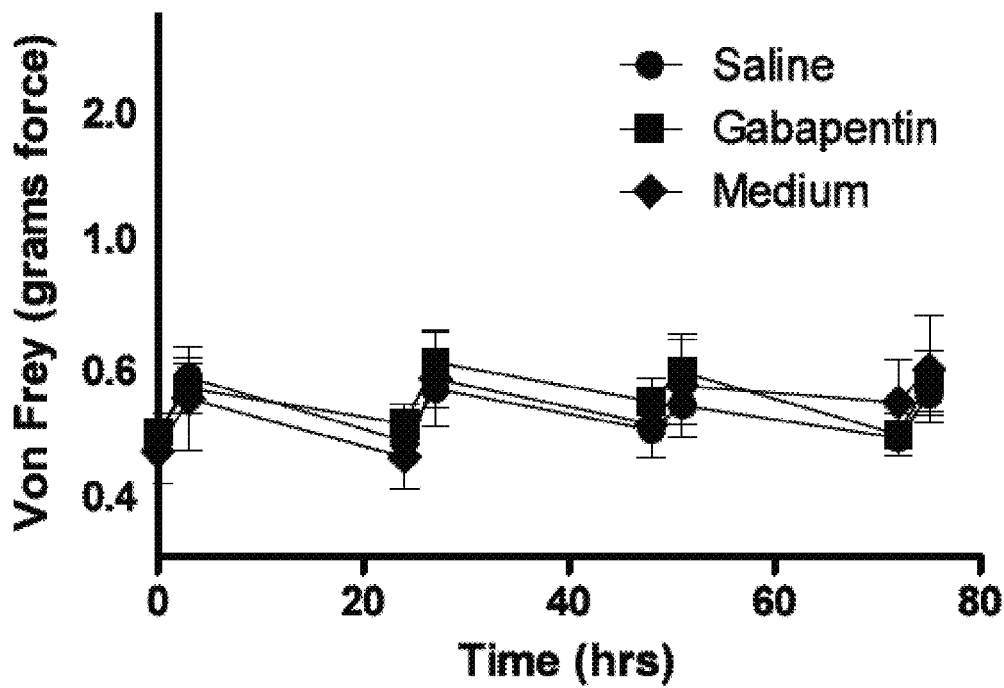
Figure 6H:
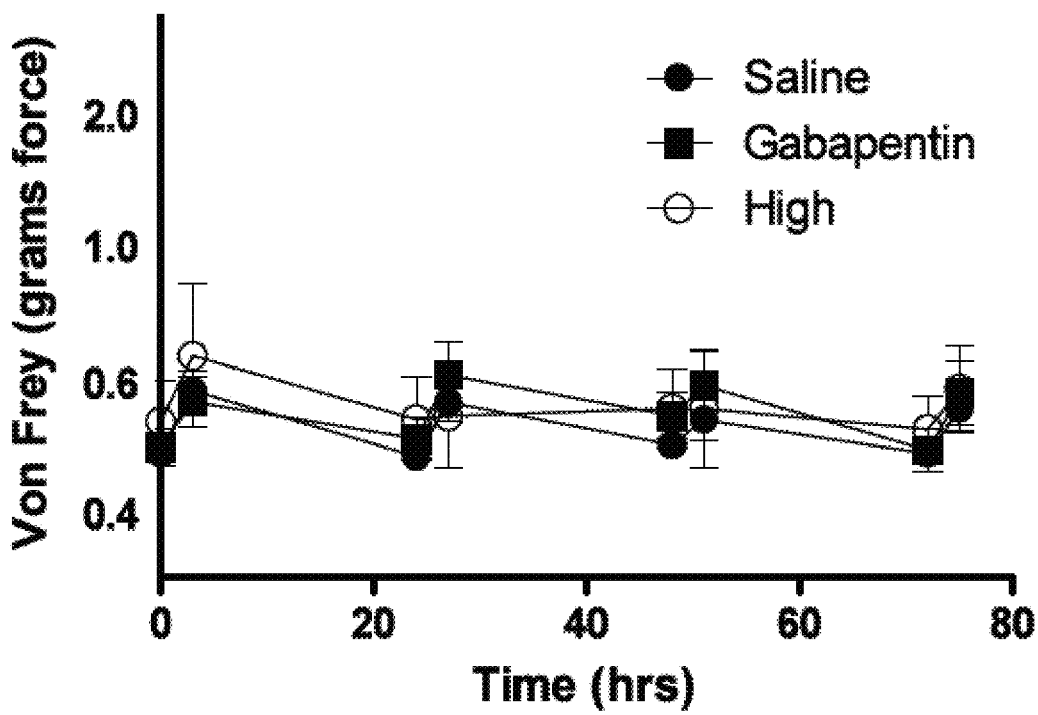
Figure 7A:
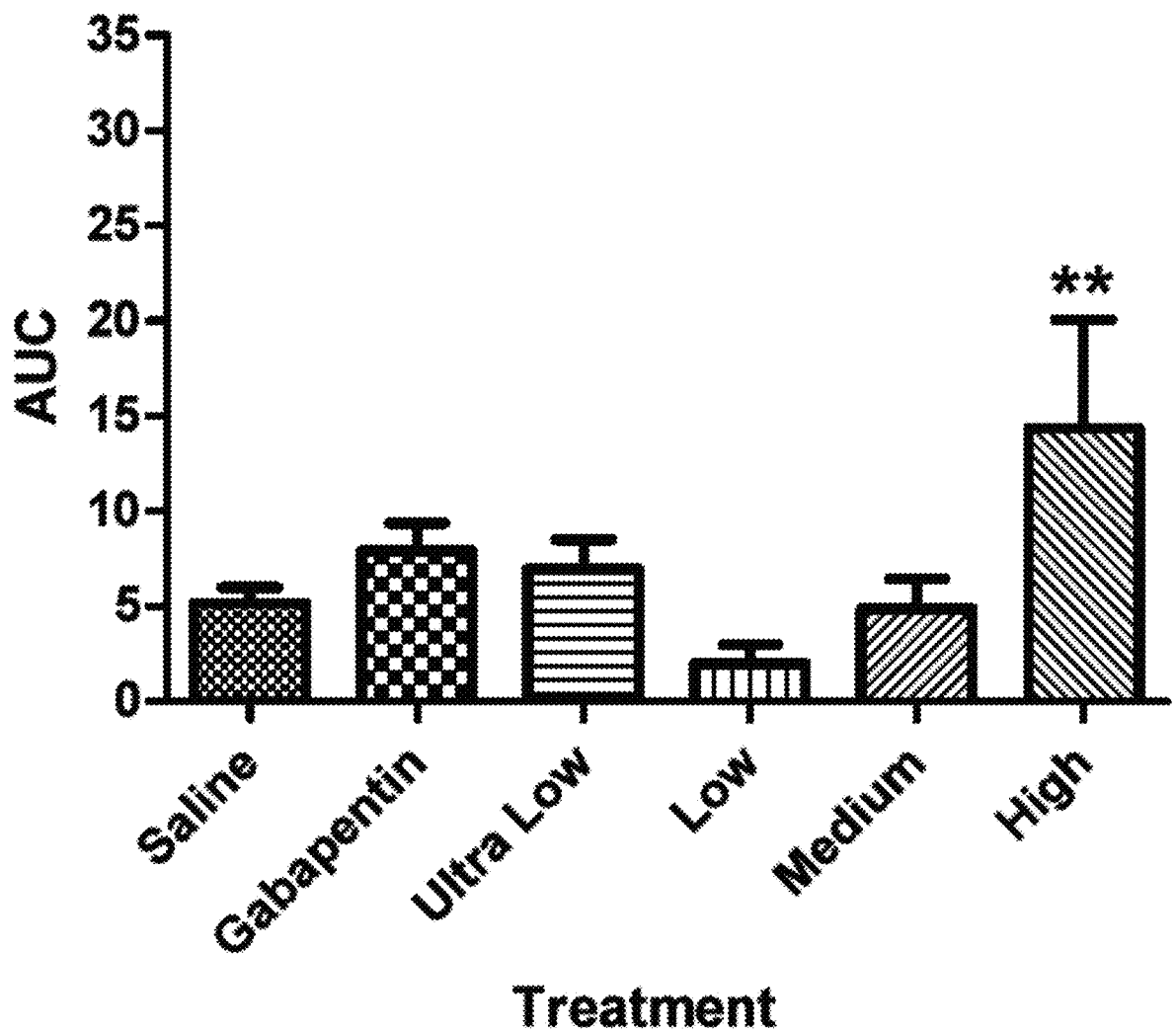
FIGS. 7A-7B present area under the curve (AUC) data for each group treated with compound II-93.
Figure 7B:
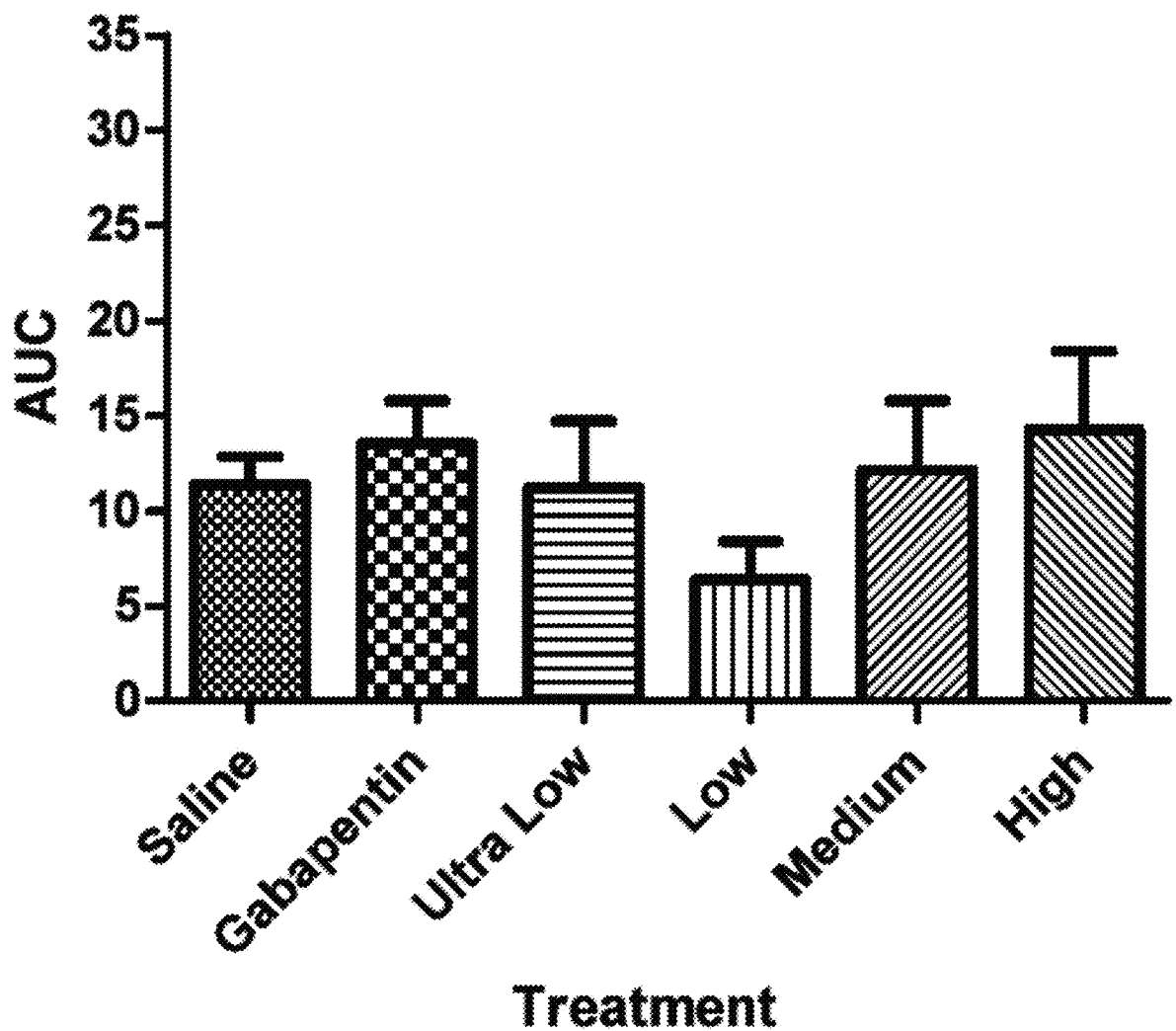

Compound II-25 showed a significant overall effect on the reversal of allodynia bilaterally compared to saline after the medium (P<0.05) or the high (P<0.05) dose. FIGS. 4A-4D presents time courses of the allodynia responses (i.e., pre-dose and post-dose) in the ipsilateral paws and FIGS. 4E-4H presents time courses of the allodynia responses in the contralateral paws for each of the four days of dosing with the different doses of Compound II-25. The effect was most prominent on Day 1 of dosing in rats treated with the high dose (3 hrs P<0.05) and Day 3 of dosing in rats treated with the medium dose (51 hrs P<0.05). The under the curve analysis is presented in FIGS. 5A-5B. From this plot, it is apparent that doses of 7.3 mg/kg and 73 mg/kg significantly reversed allodynia. It was observed that 5-6 of the animals (later revealed as having been treated with the high dose of Compound II- Compound II-93 significantly reversed allodynia in the ipsilateral paw after the high dose only (P<0.01). The effect was most prominent on Days 2 and 3 of dosing (27 hrs P<0.01; 51 hrs P<0.01) (see FIGS. 6A-6D). The under the curve analysis is plotted in FIGS. 7A-7B, in which the significant reversal of allodynia in the ipsilateral paw (see FIG. 7A) was detected after treatment with the high dose (i.e., 79 mg/kg) of Compound II-93. Throughout the testing, many of the rats were observed to be sleepy or sedated, and some rats had some swelling of the ipsilateral paw. After unblinding, it was revealed that 7 of the animals treated with the high dose of compound II-93 displayed sedation on at least one post dosing occasion and had swelling of the ipsilateral paw; and that two rats treated with the medium dose and one rat treated with the low dose showed some sedation.

Compound II-62 did not significantly reverse allodynia at any dose (data not shown). The area under the curve analysis demonstrated that there was no overall effect of any dose of compound II-62 compared to saline, but time course analysis revealed that there was a slight reversal of allodynia on the ipsilateral paw on Day 4 of dosing, however. After unblinding, it was revealed that one rat treated with the low dose, one treated with the medium dose, and two rats treated with the high dose of compound II-62 appeared sleepier than the other rats on at least one post dosing occasion. It was also observed that injection of the high dose of compound II-62 appeared to irritate the rats when it was injected. Some of the rats administered this dose showed swelling around the site of injection the next day.

Compound III-2 had no effect on allodynia at any dose (data not shown). There were no significant effects of this compound compare to saline in any of the statistical tests conducted. Two rats, later revealed to have been treated with the low dose of compound III-2 had increased levels of sleepiness during one of the post dosing testing sessions.

In summary, this study revealed that two of the tested (+)-morphinans, i.e., compounds II-25 and II-93, were effective at reversing mechanical allodynia.

Example 5

Evaluation of (+)-Morphinans to Inhibit/Reduce Acetaminophen-Induced Hepatotoxicity Acetaminophen-induced liver damage is the most common cause of death due to acute liver failure. Treatment with a (+)-morphinan may reduce or prevent acute liver injury induced by acetaminophen (APAP). The effectiveness of some of the (+)-morphinan compounds disclosed herein to reduce liver injury after exposure to a toxic dose of APAP was tested in mouse model of APAP-induced toxicity.

For this, APAP-induced liver toxicity was induced in male C57BL/6 mice aged between 8-10 weeks by a single intraperitoneal (ip) injection of APAP in PBS at a dose of 500 mg/Kg (Imaeda et al. (2009) J. Clin. Invest. 119(2):305-314). The ability of (+)-morphinans to reduce liver toxicity was tested in the following groups:

1) No APAP and PBS
2) APAP and PBS
3) No APAP and (+)-morphinan
4) APAP and (+)-morphinan The (+)-morphinan (or PBS) was either administered as a single subcutaneous (sc) or ip injection concurrent with the APAP injection or one hour prior to the APAP injection. Table 6 presents the (+)-morphinans tested.

TABLE 6

Test compounds and doses.

| Test Agent | Dose | Timing |
|---|---|---|
| (+)-naloxone | 60 mg/kg, ip (PBS) | Concurrent |
| Cmpd II-78 | 30 mg/kg, sc (PBS) | One hr prior |
| Cmpd II-24 | 60 mg/kg, sc (PBS) | One hr prior |
| Cmpd II-93 | 60 mg/kg, sc (PBS) | One hr prior |
| Cmpd III-2 | 30 mg/kg, sc (50% EtOH/NS) | One hr prior |

The mice were sacrificed 12 hours post-APAP treatment. Liver samples were stained with H&E and analyzed for signs of necrosis and hemorrhage. Histology scores were assigned using the standard rating scale. The levels of serum alanine transaminase (ALT) were also measured in each animal using a standard assay.

Figure 8B:
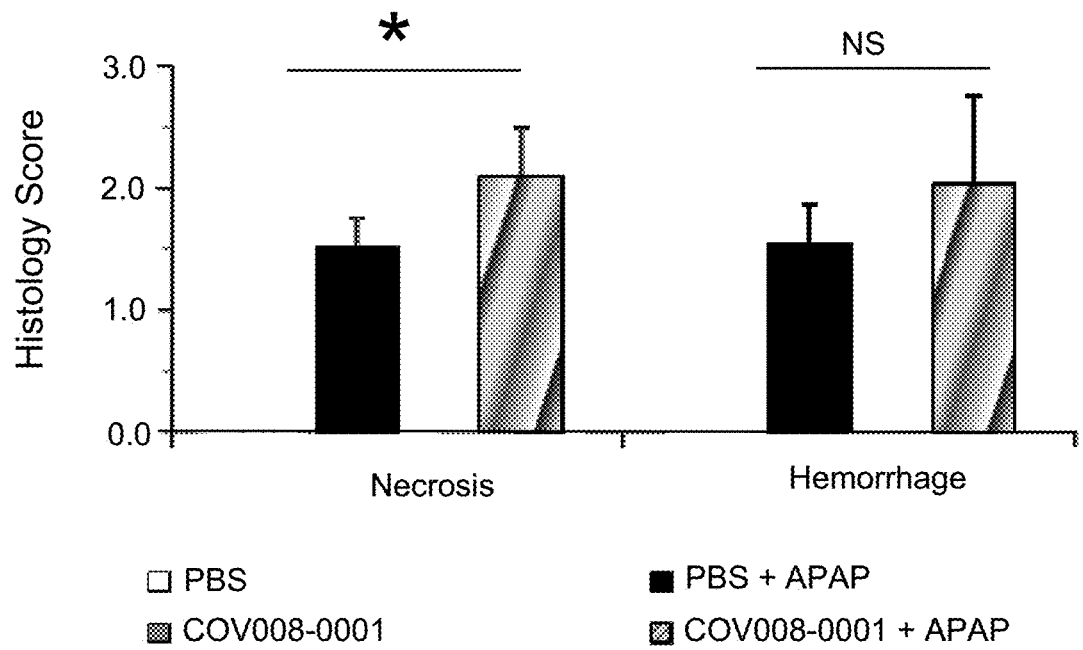
Figure 8B:
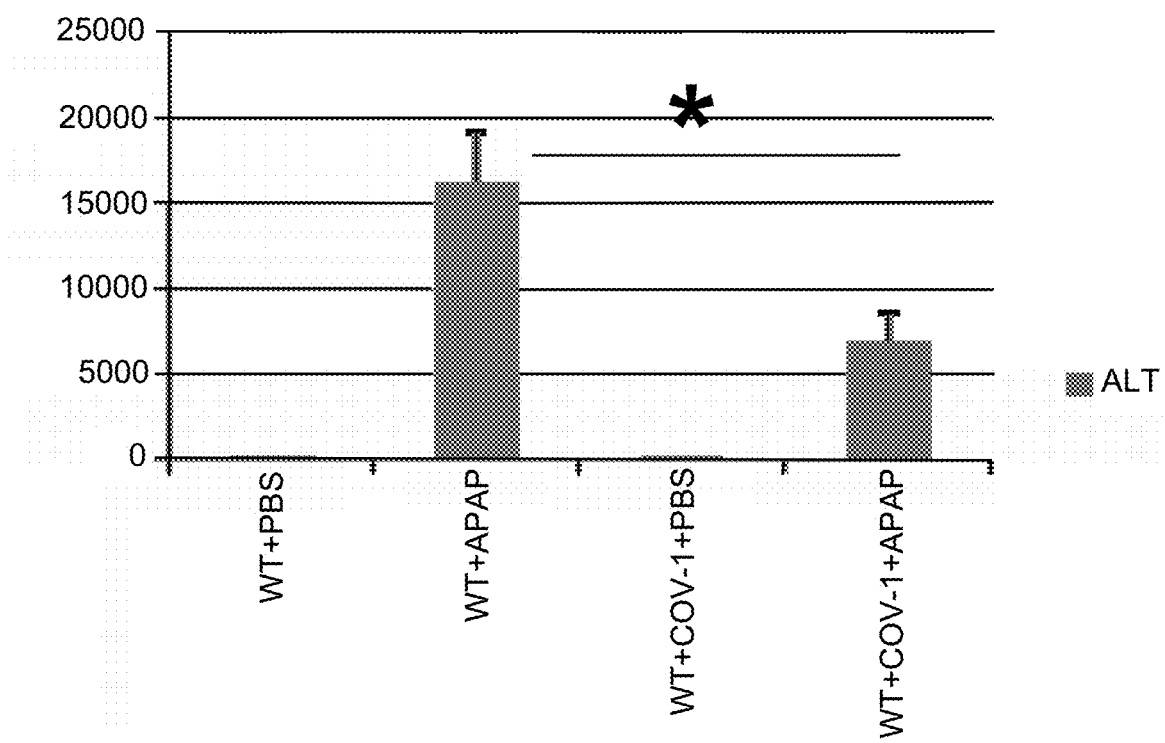

Animals administered APAP alone had significant liver injury as evidenced by increased histology scores and elevated ALT levels. (+)-Naloxone administered at the same time as the toxic dose of APAP provided essentially no protection. As shown in FIGS. 8A-8B, (+)-naloxone reduced the ALT levels, but did not improve the histology scores for necrosis and hemorrhage.

Figure 9A:
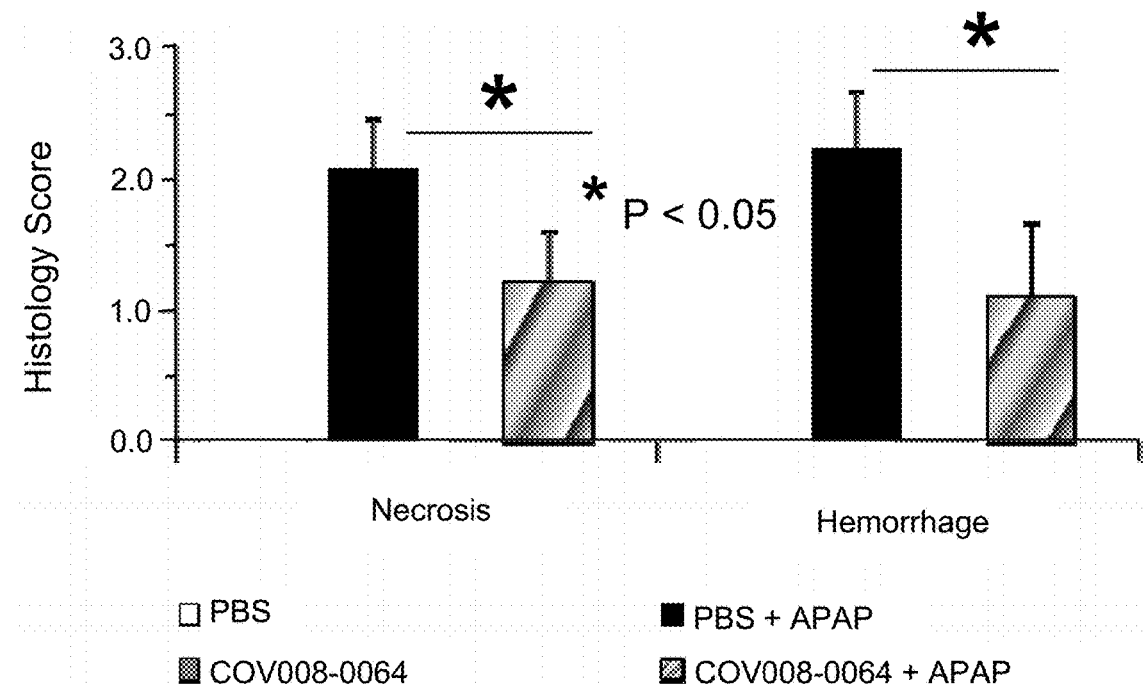
FIGS. 9A-9B illustrate that compound II-78 (i.e., COV008-0064) provided protection for acetaminophen-induced hepatotoxicity.
Figure 9B:
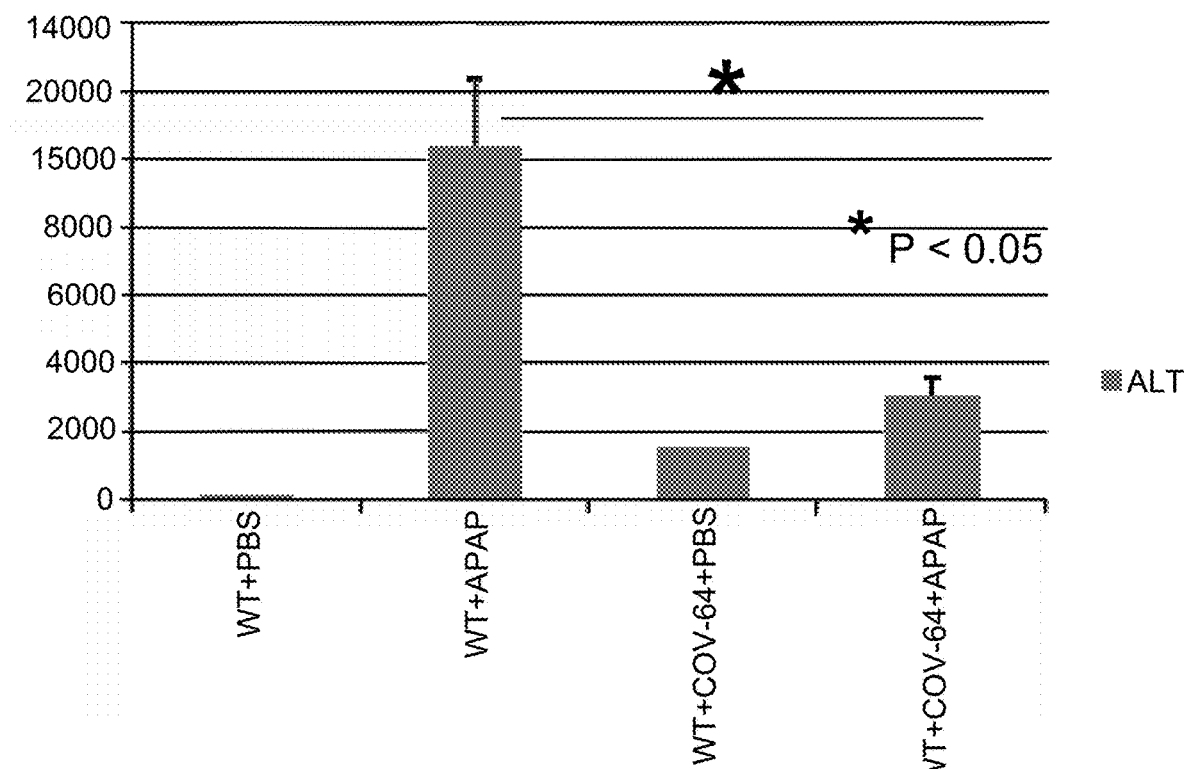

Compound II-78 provided protection from APAP-induced toxicity. Compound II-78 protected the liver from necrosis and hemorrhage($P<0.05$)—the histology scores were reduced to about half of those treated only with APAP (see FIG. 9A). Similarly, ALT levels were reduced significantly ($P<0.05$) by pretreatment with compound II-78 (see FIG. 9B).

None of compounds II-24, II-93, or III-2 provided any protection from APAP-induced toxicity (data not shown). For each compound, the histology scores were about the same as those only exposed to APAP, and ALT levels were similar between the two groups.

Example 6

Evaluation of (+)-Morphinans to Inhibit/Reduce Inflammation Using EAE Model

The effectiveness of (+)-morphinans to reduce inflammation was tested using the EAE (Experimental Autoimmune Encephalomyelitis (EAE) Lewis rat model. For this, six groups of 10 rats/group of female Lewis rats (7 weeks old; ~200 g) were used in the study. The groups included a vehicle (20% 2-hydroxypropyl, β-cyclodextrin, HBC), a positive control (prednisolone), and four test (+)-morphinans. The groups are presented below:

| | | |
|---|---|---|
| 1. | Vehicle: | 2.5 ml/kg of 20% HBC; 80% PBS |
| 2. | Prednisolone: | 4.5 mg/kg (20% HBC; 80% PBS), ip |
| 3. | Cmpd II-24 | 20 mg/kg (sterile, dd $H_2O$), sc |
| 4. | Cmpd II-38 | 20 mg/kg (sterile, dd $H_2O$), sc |
| 5. | Cmpd II-78 | 20 mg/kg (sterile, dd $H_2O$), sc |
| 6. | Cmpd II-98 | 5 mg/kg (sterile, dd $H_2O$), sc |

Each rat was injected with 0.05 ml of an emulsion of *Mycobacterium tuberculosis* H37 and guinea pig spinal cord into each main foot pad of the rear paws using conscious restraint. The compounds (or vehicle) were administered twice daily (bid). The first dose was give prior to EAE induction. Dosing continued for 20 days.

Body weight, paw thickness and clinical signs of EAE were measured for each rat 2 times per week starting the 2nd week of treatment and continued until the end of study. Clinical scoring was conducted according to the table below. Rats in which scores were not clear cut were give half scores, such as 3.5. Statistics were conducted on the clinical scores for the period in which onset of disease was observed until recovery. A Repeated Measures One Way ANOVA followed by a Newman-Keuls posthoc test if significant was conducted (Graphpad Prism 5, La Jolla, Calif.). Data presented as Mean±SEM.

| EAE Score | Symptoms |
|---|---|
| 0 | Normal |
| 1 | Limp tail |
| 2 | Incomplete paralysis of one or both hind limbs (weakness, limping, shaking) |
| 3 | Complete paralysis of one hind limb or both hind limbs can move but do not help in movement of the body |
| 4 | Complete paralysis of both hind limbs (back half or rat is dragged around the cage) |
| 5 | Complete paralysis of hind limbs and weakness of one or both forelimbs or moribund, or death |

Figure 10:
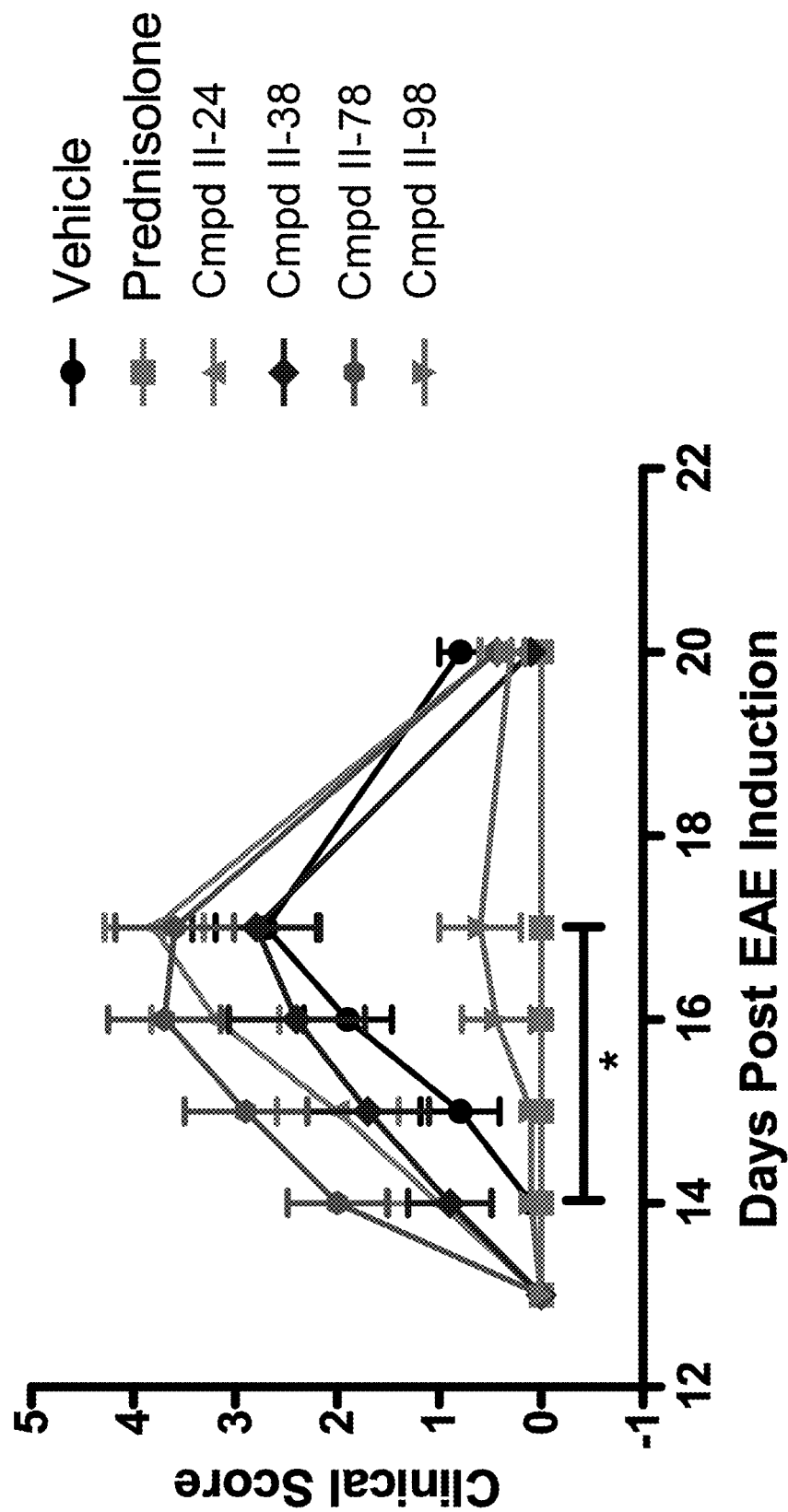
FIG. 10 presents a time course of clinical scores of experimental autoimmune encephalomyelitis following treatment with a variety of (+)-morphinans.

The EAE clinical scores for each group of rats are presented in FIG. 10. Prednisolone (positive control) and Cmpd II-98 (5 mg/kg bid subcutaneous) significantly reduced EAE clinical scores compared to vehicle control (p<0.05). Initially, Cmpd II-98 was dosed at 20 mg/kg bid, however, acute toxicity was observed. Starting on the second day of dosing, Cmpd II-98 was delivered at 5 mg/kg bid subcutaneous.

Compounds Cmpd II-24, Cmpd II-38, and Cmpd II-78 were delivered subcutaneous at 20 mg/kg bid and did not improve EAE compared to vehicle control. However, Cmpd II-38 did not dissolve into a solution and was delivered throughout the study as a suspension. It is not known whether the suspension dissolved adequately in the body to provide sufficient plasma concentration for efficacy.

In summary, Cmpd II-98 had anti-inflammatory effects in the EAE Lewis rat model.

Example 7

Evaluation of (+)-Morphinans to Inhibit/Reduce Tumor Growth and Metastasis

To determine whether (+)-morphinans inhibit pancreatic tumor growth and metastasis, the following example may be performed. Human pancreatic tumor cell line AsPC-1 cells (~1×10$^6$) may be injected into the pancreas of nude mice on Day 0. On Day 10 (when the tumors are about 3-4 mm in diameter), the mice may be divided into at least two treatment groups (~10 mice per group): (1) control—no treatment; and (2) (+)-morphinan treatment. The control group may be administered PBS or vehicle in a manner similar to the (+)-morphinan treatment group(s). The (+)-morphinan may be administered ip daily for 10-15 days, sc daily for 10-15 days, or iv every 4 days for a total of 4 times. On day 24/25, the mice may be sacrificed. To determine whether treatment with the (+)-morphinan reduced tumor growth, the tumors may be weighed and/or the volume of the tumors may be quantified. The occurrence of metastatic loci may be determined in the lungs, liver, and lymph to determine the effect of the (+)-morphinan on metastasis.

A similar analysis may be performed using a (+)-morphinan in combination with another type of chemotherapeutic agent.

Example 8

Evaluation of (+)-Morphinans in Combination with Chemotherapeutic Agent to Treat Xenograft Tumor To determine whether (+)-morphinans increase the efficacy of chemotherapeutic agents, the following trial may be performed. Female nude mice (Hsd:Athymic Nude-Foxn1 nu/nu; 5-6 weeks old) may be injected sc into the right shoulder region with EGFR expressing human tumor cells. The mice may be divided into the following treatment groups (~10 rats/group):
1) Vehicle: saline
2) Cisplatin 6 mg/kg, iv, 3× daily
3) Cisplatin 6 mg/kg iv and (+)-morphinan 20 mg/kg, sc, 3× daily
4) EGFR inhibitor, iv, 3× daily
5) EGFR inhibitor iv and (+)-morphinan 20 mg/kg, sc, 3× daily
6) (+)-morphinan 20 mg/kg, sc, 3× daily Palpation for tumors may begin 7 days post implantation. Tumors may be observed and measured 3 times a week. Caliper measures—in mm width (small measure)×length (large measure). Body weight may be recorded on day 1 of the trial (day of cell implantation) and once weekly until necropsy. NIH euthanasia guidelines for rodent tumors will be followed (e.g., if tumor diameter exceeds 20 mm, if tumor is ulcerated tumor, if tumor severely restricts the animal's ability to eat, drink, eliminate wastes, breathe, or ambulate, or if animal is becoming emaciated and/or loses more than 20% of pre-study weight).

What is claimed is:

1. A method for inhibiting Toll-like Receptor 9 (TLR9) activation, the method comprising contacting a cell expressing TLR9 with at least one (+)-4,5-epoxy morphinan compound chosen from:

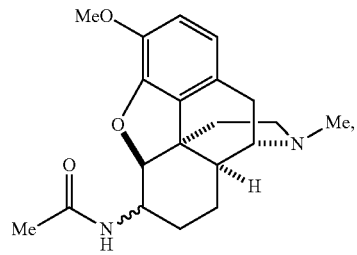

II-9

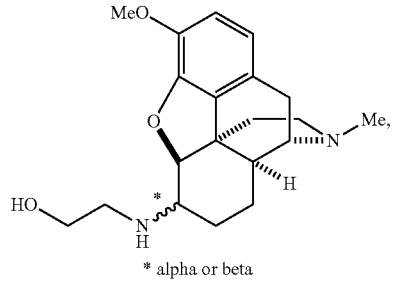

II-10

* alpha or beta

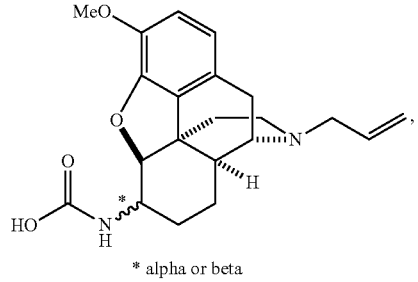

II-20

* alpha or beta

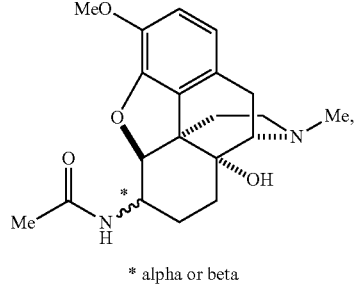

II-42

* alpha or beta

-continued

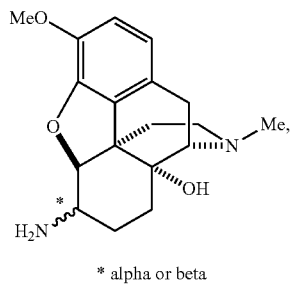

II-43

* alpha or beta

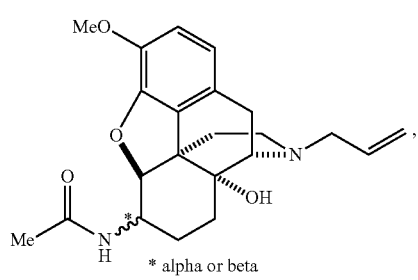

II-49

* alpha or beta

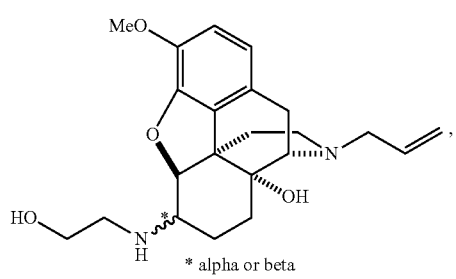

II-50

* alpha or beta

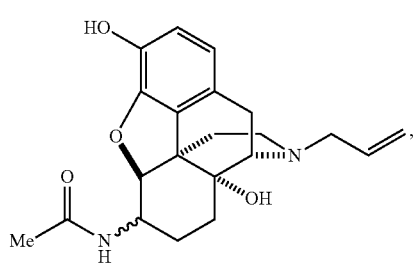

II-66

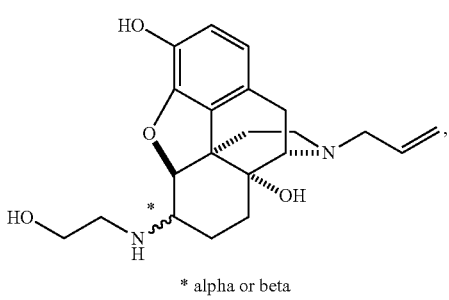

II-67

* alpha or beta

-continued

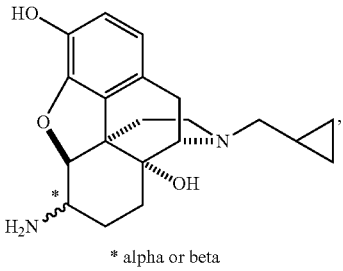

II-71

* alpha or beta

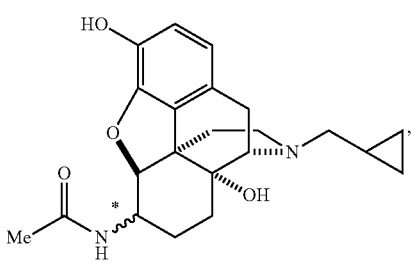

II-75

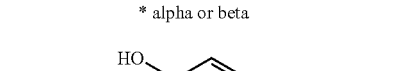

* alpha or beta

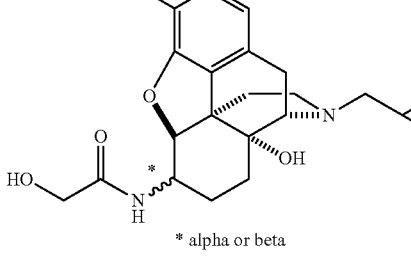

II-76

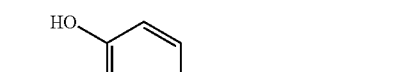

* alpha or beta

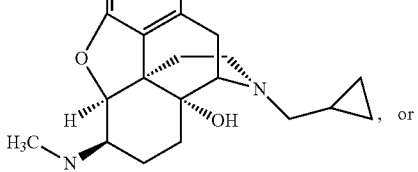

II-78

, or

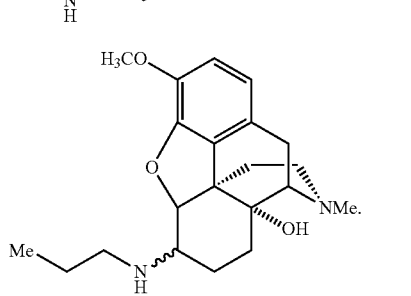

II-91

2. The method of claim 1, wherein the cell is in vitro.

3. The method of claim 1, wherein the cell is disposed in a mammalian subject.

4. The method of claim 1, wherein the cell is a glial cell, a microglial cell, or an astrocyte.

5. A method for treating a pain condition in a subject in need thereof, the method comprising administering to the subject at least one (+)-4,5-epoxy morphinan compound chosen from:

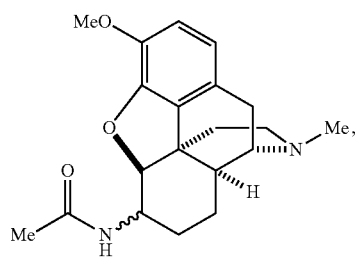 II-9
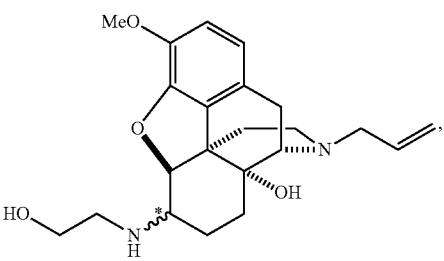 II-50
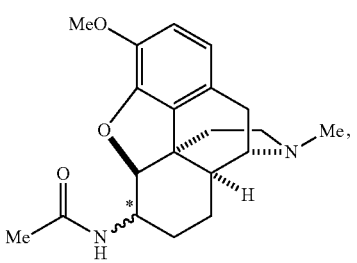 II-10
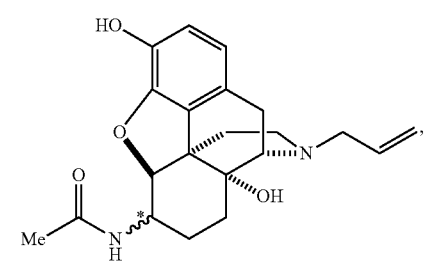 II-66
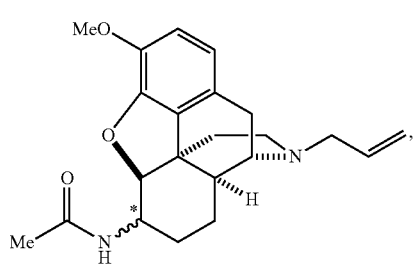 II-20
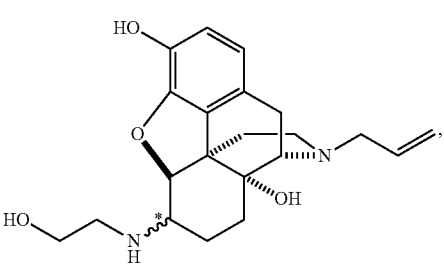 II-67
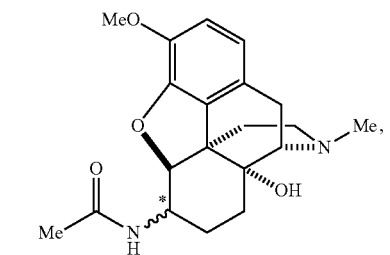 II-42
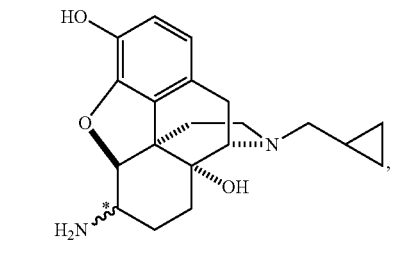 II-71
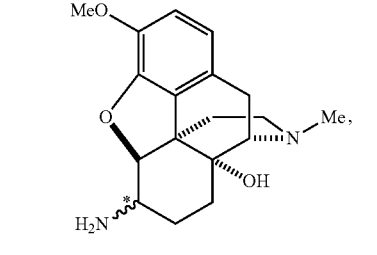 II-43
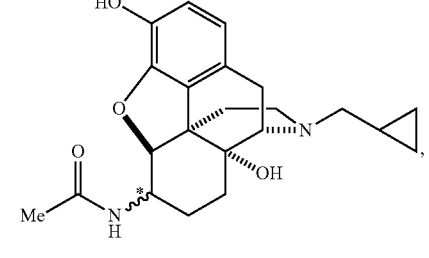 II-75
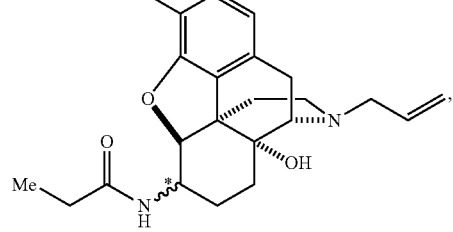 II-49
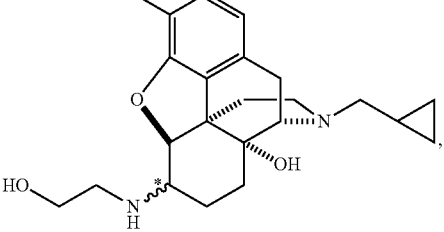 II-76

-continued
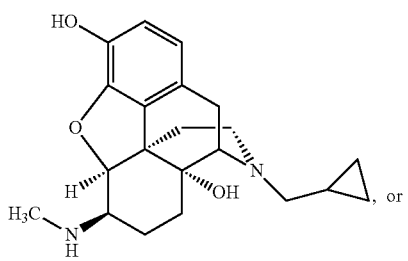
II-78
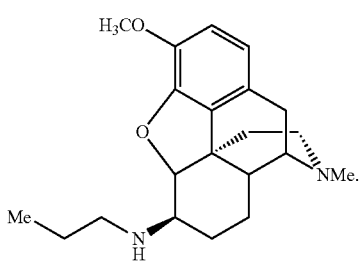
II-91
, or
* alpha or beta
6. The method of claim 5, wherein the subject is human.
7. A method for treating acetaminophen toxicity in a subject in need thereof, the method comprising administering to the subject at least one (+)-4,5-epoxy morphinan compound chosen from:
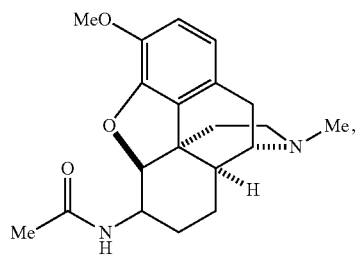
II-9
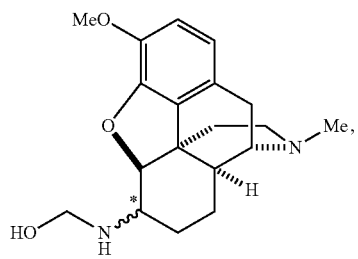
II-10
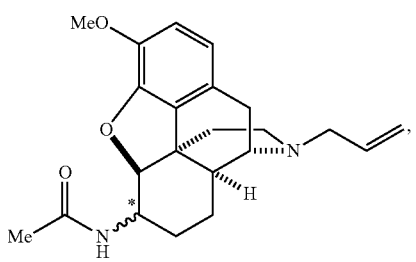
II-20
-continued
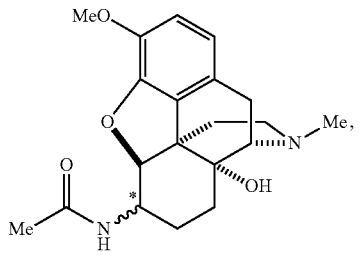
II-42
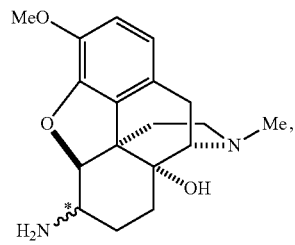
II-43
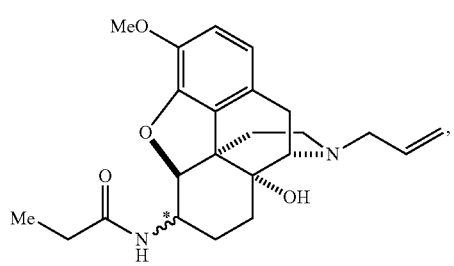
II-49
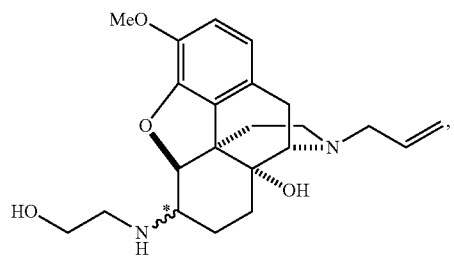
II-50
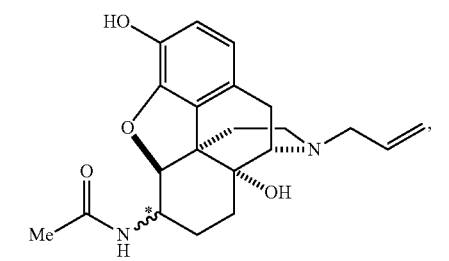
II-66
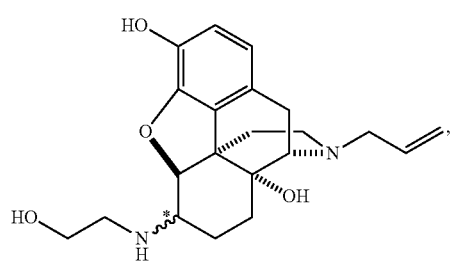
II-67

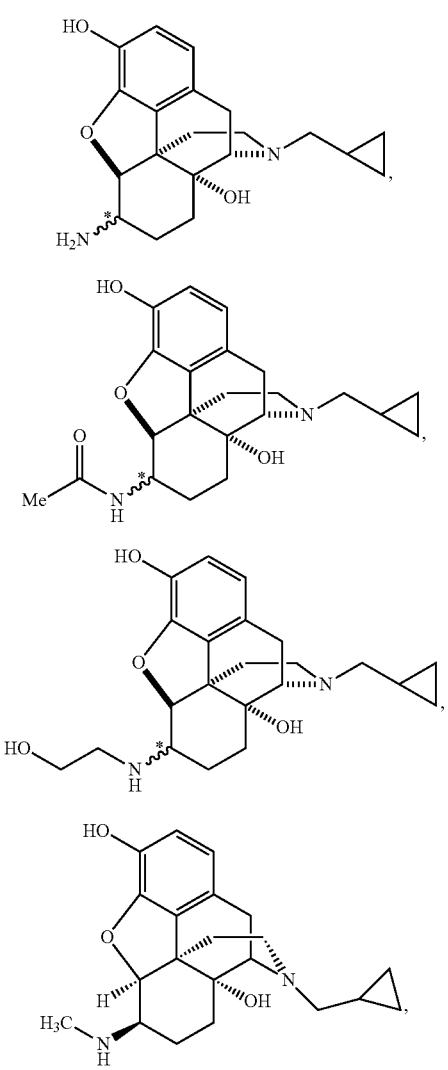
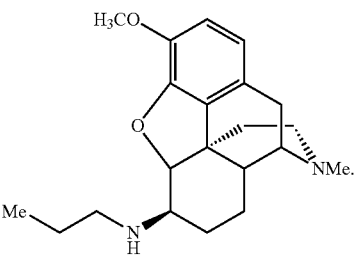
* alpha or beta
8. The method of claim 7, wherein the acetaminophen toxicity is acetaminophen-induced hepatotoxicity or acetaminophen-induced nephrotoxicity.
9. The method of claim 7, wherein the (+)-4,5-epoxy morphinan compound has formula 11-78:
10. The method of claim 7, wherein the subject is human.
* * * * *